(12) United States Patent
Abell et al.

(10) Patent No.: US 8,952,180 B2
(45) Date of Patent: Feb. 10, 2015

(54) PYRROLINONE CARBOXAMIDE COMPOUNDS USEFUL AS ENDOTHELIAL LIPASE INHIBITORS

(71) Applicant: Bristol-Myers Squibb Company, Princeton, NJ (US)

(72) Inventors: Lynn Abell, Washington Crossing, PA (US); Leonard Adam, Doylestown, PA (US); Cullen L. Cavallaro, Robbinsville, NJ (US); Heather Finlay, Skillman, NJ (US); Todd J. Friends, Bordentown, NJ (US); Jon J. Hangeland, Morrisville, PA (US); Ji Jiang, West Windsor, NJ (US); R. Michael Lawrence, Yardley, PA (US); John Lloyd, Yardley, PA (US); Zulan Pi, Pennington, NJ (US); George O. Tora, Langhorne, PA (US); Jennifer X. Qiao, Princeton, NJ (US); Carol Hui Hu, New Hope, PA (US); Tammy C. Wang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/346,745

(22) PCT Filed: Sep. 25, 2012

(86) PCT No.: PCT/US2012/056990
§ 371 (c)(1),
(2) Date: Mar. 24, 2014

(87) PCT Pub. No.: WO2013/048982
PCT Pub. Date: Apr. 4, 2013

(65) Prior Publication Data
US 2014/0221357 A1    Aug. 7, 2014

Related U.S. Application Data

(60) Provisional application No. 61/539,623, filed on Sep. 27, 2011.

(51) Int. Cl.
| | |
|---|---|
| *A61K 31/44* | (2006.01) |
| *A61K 31/40* | (2006.01) |
| *C07D 221/02* | (2006.01) |
| *C07D 205/00* | (2006.01) |
| *C07D 207/38* | (2006.01) |
| *C07D 403/12* | (2006.01) |
| *C07D 401/06* | (2006.01) |

(Continued)

(52) U.S. Cl.
CPC .......... *C07D 207/38* (2013.01); *C07D 403/12* (2013.01); *C07D 401/06* (2013.01); *C07D 401/12* (2013.01); *C07D 403/04* (2013.01);

*C07D 403/06* (2013.01); *C07D 405/06* (2013.01); *C07D 405/12* (2013.01); *C07D 417/04* (2013.01); *C07D 417/06* (2013.01); *C07D 471/04* (2013.01); *C07D 207/28* (2013.01); *C07D 417/12* (2013.01); *C07D 487/04* (2013.01)

USPC ............ 548/540; 546/112; 514/299; 514/423

(58) Field of Classification Search
None
See application file for complete search history.

(56) References Cited

U.S. PATENT DOCUMENTS

| | | |
|---|---|---|
| 6,727,275 B2 | 4/2004 | Zou et al. |
| 6,936,633 B2 | 8/2005 | Zou et al. |

(Continued)

FOREIGN PATENT DOCUMENTS

| | | |
|---|---|---|
| DE | 19535842 A1 | 3/1997 |
| WO | WO99/32611 A1 | 7/1999 |

(Continued)

OTHER PUBLICATIONS

Bevilacqua, M. et al., "Selectins", J. Clinical Invest., vol. 91, pp. 379-387 (1993).

(Continued)

*Primary Examiner* — Heidi Reese
(74) *Attorney, Agent, or Firm* — Jing G. Sun

(57) ABSTRACT

The present invention provides compounds of Formula (I) or Formula (III): [INSERT CHEMICAL STRUCTURE HERE] (I) [INSERT CHEMICAL STRUCTURE HERE] (III) as defined in the specification and compositions comprising any of such novel compounds. These compounds are endothelial lipase inhibitors which may be used as medicaments.

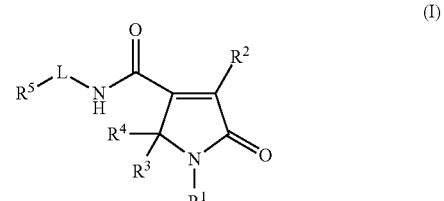

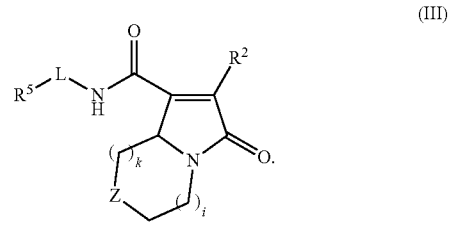

18 Claims, No Drawings

(51) Int. Cl.
*C07D 401/12* (2006.01)
*C07D 403/04* (2006.01)
*C07D 403/06* (2006.01)
*C07D 405/06* (2006.01)
*C07D 405/12* (2006.01)
*C07D 417/04* (2006.01)
*C07D 417/06* (2006.01)
*C07D 471/04* (2006.01)
*C07D 207/28* (2006.01)
*C07D 417/12* (2006.01)
*C07D 487/04* (2006.01)

(56) References Cited

U.S. PATENT DOCUMENTS

| | | |
|---|---|---|
| 7,109,186 B2 | 9/2006 | Walker et al. |
| 7,217,727 B2 | 5/2007 | Eacho et al. |
| 7,595,403 B2 | 9/2009 | Eacho et al. |
| 2004/0229909 A1 | 11/2004 | Kiyama et al. |
| 2005/0004180 A1 | 1/2005 | Zou et al. |
| 2006/0211755 A1 | 9/2006 | Eacho et al. |
| 2006/0281949 A1 | 12/2006 | Weber et al. |
| 2008/0287448 A1 | 11/2008 | Zoller et al. |
| 2009/0054478 A1 | 2/2009 | Zoller et al. |
| 2009/0076068 A1 | 3/2009 | Zoller et al. |
| 2010/0105719 A1 | 4/2010 | Zoller et al. |

FOREIGN PATENT DOCUMENTS

| | | |
|---|---|---|
| WO | WO2004/004657 A2 | 1/2004 |
| WO | WO2004/093872 A1 | 11/2004 |
| WO | WO2004/094393 A1 | 11/2004 |
| WO | WO2004/094394 A1 | 11/2004 |
| WO | WO2007/042178 A1 | 4/2007 |
| WO | WO2007/110215 A1 | 10/2007 |
| WO | WO2007/110216 A1 | 10/2007 |
| WO | WO2009/123164 A1 | 10/2009 |
| WO | WO2009/133834 A1 | 11/2009 |

OTHER PUBLICATIONS deLemos, A. et al., "Identification of Genetic Variants in Endothelial Lipase in Persons With Elevated High-Density Lipoprotein Cholesterol", Circulation, vol. 106, pp. 1321-1326 (2002).
Emerson, D. et al., "Ring Opening Reactions of 6-Oxo-substituted Spiro-pyrrolidinediones: Synthesis of 4-Substituted-1,5-Dihydro-3-Hydroxy-2-oxo-1,5-diphenyl-2H-pyrroles", J. Heterocyclic Chem., vol. 35, pp. 611-617 (1998).
Folkman, J. et al., "Angiogenic Factors", Science, vol. 235, pp. 442-447 (1987).
Folkman, J. et al., "Angiogenesis" *Minireview*. The J. of Biological Chemistry, vol. 267(16) pp. 10931-10934 (1992).
Gein, V.L. et al., "Five-Membered 2, 3-Dioxoheterocycles. XXI.* Synthesis of 1, 5-Diaryl-4-Tert-Butoxycarbonyl-3-Hydroxy-2, 5-Dihydro-2-Pyrrolones and Their Reaction with Arylamines and o-Phenylenediamine", Russian J. of General Chemistry, vol. 62(8) pp. 1722-1729 1992.
Gein, V.L. et al., "Five-Membered 2,3-Dioxo Heterocycles.21.* Reaction of 1,5-Diaryl-4-Ethoxycarbonyl-tetrahydropyrrole-2,3-diones with 2-aminopyridine", Russian J. of General Chemistry, vol. 62(8), pp. 27-30 (1992).
Gein, V.L. et al., "Five-Membered 2,3-Dioxoheterocycles. XXII.* Reactions of 1,5-Diaryl-3-Hydroxy-2-Oxo-3-Pyrroline-4-Carboxylic Acids and their Functional Derivatives with Diphenyldiazomethane and the Thermolysis of Products of the Reactions", Russian J. of General Chemistry, vol. 62(8), pp. 1559-1564 (1992).

Gein, V.L. et al., "Five-Membered 2,3-Dioxoheterocycles XXX. Cyclization of 1,5-Diaryl- and 1-Methyl-5-Phenyl-4-Ethoxalylacetyltetrahydropyrrole-2,3-Diones and Their Arylamino Derivatives", Russian J. of General Chemistry, vol. 62(8), pp. 1710-1715 (1992).
Gein, V.L. et al., "Five-Membered 2,3-Dioxoheterocycles. XXXI.* Reactions of 1,5-Diaryl-3-Hydroxy-4-*tert*-Butoxycarbonyl-3-Pyrrolin-2-ones with Hydrazine Derivatives", Russian J. of General Chemistry, vol. 63(10), pp. 1613-1616 (1993).
Gordon, D.J. et al., "High-Density Lipoprotein-The Clinical Implications of Recent studies", New England J. of Medicine, vol. 321(19), pp. 1311-1316 (1989).
Gordon, D.J. et al., "High-Density Lipoprotein Cholesterol and Cardiovascular Disease", Circulation, vol. 79, pp. 8-15 (1989).
Hirata, K. et al., "Cloning of a Unique Lipase from Endothelial Cells Extends the Lipase Gene Family", The J. of Biological Chemistry, vol. 274(20), pp. 14170-14175 (1999).
Janssens, S.P. et al., "Cloning and Expression of a cDNA Encoding Human Endothelium-derived Relaxing Factor/Nitric Oxide Synthase", The J. of Biological Chemistry, vol. 267(21), pp. 14519-14522 (1992).
Jaye, M. et al., "A novel endothelial-derived lipase that modulates HDL metabolism", Nature Genetics, vol. 21, pp. 424-428 (1999).
Jin, W. et al., "Lipases and HDL metabolism" Trends in Endocrinology& Metabolism, vol. 13(4), pp. 174-178 (2002).
Kadin, Saul B., "Synthesis and Antiinflammatory Properties of N-Substituted 4,5-Dioxopyrrolidine-3-carboxanilides", J. of Medicinal Chemistry, vol. 19 (1), pp. 172-173 (1976).
Lamas, S. et al., "Endothelial nitric oxide synthase: Molecular cloning and characterization of a distinct constitutive enzyme isoform", PNAS, vol. 89, pp. 6348-6352 (1992).
Lüscher, T.F. et al., "Endothelium-Derived Contracting Factors", Hypertension, vol. 19, pp. 117-130 (1992).
McCoy, M.G. et al., "Characterization of the lipolytic activity of endothelial lipase", Journal of Lipid Research, vol. 43, pp. 921-929 (2002).
Pace, P. et al., "4-Hydroxy-5-pyrrolinone-3-carboxamide HIV-1 integrase inhibitors", Bioorganic & Medicinal Chemistry Letters, vol. 18, pp. 3865-3869 (2008).
Ross, R., "The pathogenesis of atherosclerosis: a perspective for the 1990s" Nature, vol. 362(80), pp. 801-809 (1993).
Saalfrank, R. W. et al., "Synthesis and Reactions of 4-Acyl/Carbamoyl-N-aryl-3-chloro-pyrrol-2,5-diones: Crystal Structure of a Supramolecular Ribbon Based on Hydrogen Bonds [1]", Z. Naturforsch, vol. 51, pp. 1084-1098 (1996).
Southwick, P.L. et al., "1-Carbamoyl- and 1-Aminomethyl-1, 4-dihydropyrrolo[3,4-b]indole Derivatives. Indole Formation by Fragmentation of Strain-Barrier Stabilized 2-Aminoindoline Derivatives", J. of Organic Chemistry, vol. 33(5), pp. 2051-2056 (1968).
Strauss, J.G. et al., "Endothelial cell-derived lipase mediates uptake and binding of high-density lipoprotein (HDL) particles and the selective uptake of HDL-associated cholesterol esters independent of its enzymic activity", Biochem. J., vol. 368, pp. 69-79 (2002).
Sugden, J.K. et al., "Antiinflammatory activity of some N-substituted-3-carboxamido-4-hydroxy-5-oxo-3-pyrrolines", Eur. J. Med. Chem-Chimica Therapeutica, vol. 14(2), pp. 189-190 (1979).
Wei, Han-Xun et al., "Experimental Support for Planar Pseudopericyclic Transition States in Thermal Cheletropic Decarbonylations", Organic Letters, vol. 6(23), pp. 4289-4292 (2004).
Williams, T.J. et al., "Adhesion Molecules Involved in the Microvascular Inflammatory Response", Am Rev. Respir. Disease, vol. 146, pp. S45-S50 (1992).
Wong, H. et al., "The lipase gene family", Journal of Lipid Research, vol. 43, pp. 993-999 (2002).
Vaughan, W. et al., "1,5-Diaryl-2,3-pyrrolidinediones. XII. Enamines and the Pseudo-pyrrolidinediones", J. of the American Chemical Society, vol. 82 (16), pp. 4370-4076 (1960).
Yanagisawa, M. et al., "A novel potent vasoconstrictor peptide produced by vascular endothelial cells", Nature, vol. 332, pp. 411-415 (1988).

PYRROLINONE CARBOXAMIDE COMPOUNDS USEFUL AS ENDOTHELIAL LIPASE INHIBITORS

CROSS-REFERENCE TO RELATED APPLICATIONS

The present application is a 371 application of PCT/US2012/056990 filed Sep. 25, 2012, which claims priority benefit of U.S. provisional application Ser. No. 61/539,623, filed Sep. 27, 2011; each of which is fully incorporated by reference herein.

FIELD OF THE INVENTION

The present invention provides novel pyrrolinone carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, *Nature*, 362(80):1-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon et al., *N Engl. J. Med.*, 321:1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin et al., *Trends Endocrinol. Metab.*, 13:174-178 (2002); Wong et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata et al., *J. Biol. Chem.*, 274:14170-14175 (1999); Jaye et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

The novel compounds in the present disclosure are to fill the foregoing need. The pyrrolinone carboxamide compounds of similar structures are known, for example, from WO 2004/004657 by the present Applicant, which is herein incorporated by reference in its entirety, and from Pace et al., *Bioorg. Med. Chem. Leu.*, 18:3865-3869 (2008), but these compounds were only known as HIV integrase inhibitors. The present inventors have surprisingly discovered that these compounds are useful endothelial lipase inhibitors. This discovery will help advance the research in this important field and can potentially provide effective treatments for diseases or disorders associated with the activities of endothelial lipase, including, but not limited to, atherosclerosis.

SUMMARY OF THE INVENTION

The present disclosure provides novel pyrrolinone carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, other agent(s).

Other features and advantages of the invention will be apparent from the following detailed description and claims.

DETAILED DESCRIPTION OF THE INVENTION

I. Compounds of the Invention

In a first aspect, the present disclosure provides, inter alia, a compound of Formula (I):

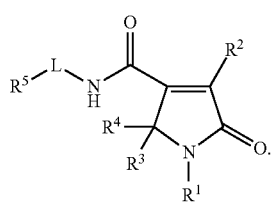

In a first embodiment of the first aspect, the present disclosure provides a compound of Formula (I), or a stereoisomer, a tautomer, a pharmaceutically acceptable salt, or a solvate thereof, wherein:

$R^1$ is independently selected from the group consisting of: H, $-((CH_2)_sO)_r(C_{1-4}$ alkyl substituted with 0-1 $R^a$), $C_{1-6}$ alkyl substituted with 0-3 $R^a$, $C_{2-6}$ alkenyl substituted with 0-3 $R^a$, $-SO_2$(phenyl), $-(CH_2)_n-(C_{3-6}$ cycloalkyl substituted with 0-3 $R^c$), $-(CH_2)_n(CHR^f)(CH_2)_m$-phenyl, $-(CH_2)_n$-(phenyl substituted with 0-3 $R^b$), and $-(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^2$ is independently selected from the group consisting of: $OR^6$, CN, and $NR^7R^8$;

$R^3$ is independently selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, $-CO_2(C_{1-4}$ alkyl), $-SO_2$(phenyl), $-(CH_2)_n-(C_{3-6}$ cycloalkyl substituted with 0-3 $R^c$), $-(CH_2)_n$-(phenyl substituted with 0-3 $R^b$), $-(CH_2)_n$-(naphthyl substituted with 0-3 $R^b$), and $-(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;

$R^4$ is independently selected from the group consisting of: H and $C_{1-4}$ alkyl;

$R^5$ is independently selected from the group consisting of: $C_{3-6}$ cycloalkyl, phenyl, naphthyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^6$ is $C_{1-6}$ alkyl substituted with 0-1 $CO_2H$;

$R^7$ is independently selected from the group consisting of: H, $C_{1-6}$ alkyl substituted with 0-1 $R^a$, $-(CH_2)_n$-(phenyl substituted with 0-3 $R^b$), and $-(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: H and $C_{1-6}$ alkyl;

alternatively, $NR^7R^8$ is a 5- to 6-membered heterocycle comprising: carbon atoms and 1-4 heteroatoms selected from N, $NR^e$, O, and $S(O)_p$;

L is independently a hydrocarbon or hydrocarbon-heteroatom linker optionally substituted with 0-2 $R^g$; wherein said hydrocarbon linker has one to eight carbon atoms and may be straight or branched, saturated or unsaturated; and said hydrocarbon-heteroatom linker may be saturated or unsaturated and has one to seven carbon atoms and one group selected from O, $-CO-$, S, $-SO-$, $-SO_2-$, NH, and $N(C_{1-4}$ alkyl);

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)$CO(C_{1-4}$ alkyl), $NHCO_2(C_{1-4}$ alkyl), $CONHSO_2(C_{1-4}$ alkyl), $SO_2(C_{1-4}$ alkyl), $CONH_2$, $CONH(C_{1-4}$ alkyl), $NHSO_2(C_{1-4}$ alkyl), $N(C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2(C_{1-4}$ alkyl), $NHSO_2(C_{1-4}$ alkyl), $N(C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: $=O$ and $R^b$;

$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2(C_{1-4}$ alkyl), $NHSO_2(C_{1-4}$ alkyl), $SO_2(C_{1-4}$ alkyl), and $SO_2NH_2$;

$R^e$ is, independently at each occurrence, selected from the group consisting of: H, $C_{1-4}$ alkyl, $CO(C_{1-4}$ alkyl), $CO_2(C_{1-4}$ alkyl), $CO_2$(benzyl), and $-(CH_2)_n$-(phenyl optionally substituted with 0-2 halogens);

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

m, at each occurrence, is selected from 0, 1, and 2;

n, at each occurrence, is selected from 0, 1, 2, 3, and 4;

p, at each occurrence, is selected from 0, 1, and 2; and s and r are, independently at each occurrence, selected from 1, 2, 3, and 4.

In a second embodiment of the first aspect, the present disclosure provides a compound of Formula (I), wherein $R^2$ is $-NHR^8$ and $R^4$ is hydrogen, further characterized by Formula (Ia):

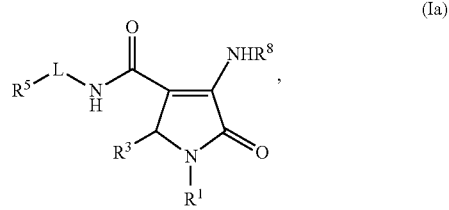

or a stereoisomer, a tautomer, a pharmaceutically acceptable salt, or a solvate thereof, within the scope of the first aspect wherein:

$R^1$ is $C_{1-4}$ alkyl substituted with 0-2 $R^a$;

$R^3$ is independently H or $C_{1-4}$ alkyl;

$R^5$ is phenyl substituted with 0-3 $R^d$;

$R^8$ is independently selected from the group consisting of: H, $C_{1-4}$ alkyl substituted with 0-2 $R^a$, $C_{3-6}$ cycloalkyl, —(CH₂)ₙ-(phenyl substituted with 0-2 Rᵃ), and —(CH₂)ₙ-(heterocycle substituted with 0-2 Rᶜ); wherein said heterocycle is selected from tetrahydrofuranyl, pyrrolidinyl, piperidinyl and pyridyl; and L is C₁₋₅ alkylene, wherein said alkylene may be straight or branched chain.

In a third embodiment of the first aspect, the present disclosure provides a compound of Formula (Ia), or a stereoisomer, a tautomer, a pharmaceutically acceptable salt, or a solvate thereof, wherein:
R¹ is C₁₋₄ alkyl;
R³ is H;
R⁵ is phenyl optionally substituted with one, two, or three halogen atoms;
R⁸ is selected from the group consisting of: H, C₁₋₄ alkyl substituted with 0-1 Rᵃ, cyclopropyl, phenyl, benzyl, (3,4-diCl-phenyl)-(CH₂)₃—, (tetrahydrofuran-2-yl)-CH₂—, (1-Me-pyrrolidin-2-yl)-(CH₂)₂—, (piperidin-1-yl)-(CH₂)₃—, and (pyrid-4-yl)-(CH₂)₂—; and
L is —(CH₂)₃— or —(CH₂)₄—.

In a fourth embodiment of the first aspect, the present disclosure provides compound of Formula (Ia), or a stereoisomer, a tautomer, a pharmaceutically acceptable salt, or a solvate thereof, wherein:
R¹ is ethyl;
R³ is H;
R⁵ is 3,4-diCl-phenyl;
R⁸ is H, methyl, —CH₂CF₃, —(CH₂)₂OCH₂CH₃, —(CH₂)₂OCH(CH₃)₂, cyclopropyl, phenyl, benzyl, (3,4-diCl-phenyl)-(CH₂)₃—, (tetrahydrofuran-2-yl)-CH₂—, (1-Me-pyrrolidin-2-yl)-(CH₂)₂—, (piperidin-1-yl)-(CH₂)₃—, and (pyrid-4-yl)-(CH₂)₂—; and
L is —(CH₂)₃—.

In a second aspect, the present disclosure provides compounds of Formula (II):

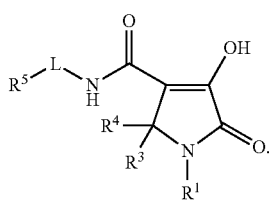

(II)

In a first embodiment of the second aspect, the present disclosure provides a compound of Formula (II), or a stereoisomer, a tautomer, a pharmaceutically acceptable salt, or a solvate thereof, wherein:
R¹ is independently selected from the group consisting of: H, C₁₋₆ alkyl substituted with 0-3 Rᵃ, C₂₋₆ alkenyl substituted with 0-3 Rᵃ, —SO₂(phenyl), —(CH₂)ₙ—(C₃₋₆ cycloalkyl substituted with 0-3 Rᶜ), —(CH₂)ₙ(CHRᶠ)(CH₂)ₘ-phenyl, —(CH₂)ₙ-(phenyl substituted with 0-3 Rᵇ), and —(CH₂)ₙ-(5- to 6-membered heterocycle comprising: carbon atoms and 1-4 heteroatoms selected from N, NRᵉ, O, and S(O)ₚ); and wherein said heterocycle is substituted with 0-3 Rᵉ;
R³ is independently selected from the group consisting of: H, halogen, CF₃, OCF₃, C₁₋₆ alkyl substituted with 0-3 Rᵃ, C₂₋₆ alkenyl substituted with 0-3 Rᵃ, —CO₂(C₁₋₄ alkyl), —SO₂(phenyl), —(CH₂)ₙ—(C₃₋₆ cycloalkyl substituted with 0-3 Rᶜ), —(CH₂)ₙ-(phenyl substituted with 0-3 Rᵇ), —(CH₂)ₙ-(naphthyl substituted with 0-3 Rᵇ), and —(CH₂)ₙ-(5- to 10 membered heterocycle comprising: carbon atoms and 1-4 heteroatoms selected from N, NRᵉ, O, and S(O)ₚ), wherein said heterocycle is substituted with 0-3 Rᶜ;
R⁴ is independently selected from the group consisting of: H and C₁₋₄ alkyl;
R⁵ is independently selected from the group consisting of: C₃₋₆ cycloalkyl, benzothiazolyl, indazolyl, chromanyl, and quinolinyl; and wherein each moiety is substituted with 0-3 Rᵈ;
alternatively, R⁵ is phenyl substituted with OCF₃ or SO₂NH₂;
L is independently a hydrocarbon or hydrocarbon-heteroatom linker; wherein said hydrocarbon linker is saturated and has one to eight carbon atoms; and said hydrocarbon-heteroatom linker is saturated and has one to seven carbon atoms and one O;
Rᵃ is, independently at each occurrence, selected from the group consisting of: halogen, OH, C₁₋₄ alkyl, C₁₋₄ alkoxy, C₁₋₄ haloalkyl, C₁₋₄ haloalkoxy, CF₃, OCF₃, CN, NH₂, NO₂, NH(C₁₋₄ alkyl), N(C₁₋₄ alkyl)₂, CO₂H, CO₂(C₁₋₄ alkyl), NHCO(C₁₋₄ alkyl substituted with 0-1 NH₂), N(C₁₋₄ alkyl) CO(C₁₋₄ alkyl), NHCO₂(C₁₋₄ alkyl), CONHSO₂(C₁₋₄ alkyl), SO₂(C₁₋₄ alkyl), CONH₂, CONH(C₁₋₄ alkyl), NHSO₂(C₁₋₄ alkyl), N(C₁₋₄ alkyl)SO₂(C₁₋₄ alkyl), and phenoxy;
Rᵇ is, independently at each occurrence, selected from the group consisting of: halogen, OH, C₁₋₄ alkyl, C₁₋₄ alkoxy, C₁₋₄ haloalkyl, C₁₋₄ haloalkoxy, CF₃, OCF₃, OCF₂CHF₂, OCH₂CF₃, CN, NH₂, NO₂, NH(C₁₋₄ alkyl), N(C₁₋₄ alkyl)₂, CO₂H, CO₂(C₁₋₄ alkyl), CONH₂, CONH(C₁₋₄ alkyl), CON(C₁₋₄ alkyl)₂, NHCO₂(C₁₋₄ alkyl), NHSO₂(C₁₋₄ alkyl), N(C₁₋₄ alkyl)SO₂(C₁₋₄ alkyl), SO₂(C₁₋₄ alkyl), SO₂NH₂, phenyl, benzyl, and phenoxy;
Rᶜ is, independently at each occurrence, selected from the group consisting of: =O and Rᵇ;
Rᵈ is, independently at each occurrence, selected from the group consisting of: halogen, OH, C₁₋₆ alkyl, C₁₋₄ alkoxy, C₁₋₄ haloalkyl, C₁₋₄ haloalkoxy, CF₃, OCF₃, CN, NH₂, NO₂, NH(C₁₋₄ alkyl), N(C₁₋₄ alkyl)₂, CO₂H, CO₂(C₁₋₄ alkyl), CONH₂, CONH(C₁₋₄ alkyl), CON(C₁₋₄ alkyl)₂, NHCO₂(C₁₋₄ alkyl), NHSO₂(C₁₋₄ alkyl), SO₂(C₁₋₄ alkyl), and SO₂NH₂;
Rᵉ is, independently at each occurrence, selected from the group consisting of: H, C₁₋₄ alkyl, CO(C₁₋₄ alkyl), CO₂(C₁₋₄ alkyl), CO₂(benzyl), and —(CH₂)ₙ-(phenyl optionally substituted with 0-2 halogens);
Rᶠ is, independently at each occurrence, selected from the group consisting of: C₁₋₄ alkyl, C₂₋₄ alkenyl, CO₂(C₁₋₄ alkyl), C₃₋₆ cycloalkyl, phenyl, and benzyl;
m, at each occurrence, is selected from 0, 1, and 2;
n, at each occurrence, is selected from 0, 1, 2, 3, and 4;
p, at each occurrence, is selected from 0, 1, and 2; and
s, at each occurrence, is selected from 1, 2, 3, and 4.

In a second embodiment of the second aspect, the present disclosure provides a compound of Formula (II), or a stereoisomer, a tautomer, a pharmaceutically acceptable salt, or a solvate thereof, wherein:
R¹ is C₁₋₄ alkyl;
R⁵ is independently selected from the group consisting of: cyclohexyl, indazolyl, chromanyl, and quinolinyl; and wherein each moiety is substituted with 0-2 Rᵈ;
alternatively, R⁵ is phenyl substituted with OCF₃ or SO₂NH₂; and
L is independently —(CH₂)₃—, or —(CH₂)₄—.

In a third embodiment of the second aspect, the present disclosure provides a compound of Formula (II), or a stereoisomer, a tautomer, a pharmaceutically acceptable salt, or a solvate thereof, wherein:
R¹ is independently selected from the group consisting of: H, C₁₋₆ alkyl substituted with 0-3 Rᵃ, C₂₋₆ alkenyl substituted with 0-3 $R^a$, —SO$_2$(phenyl), —(CH$_2$)$_n$—(C$_{3-6}$ cycloalkyl substituted with 0-3 $R^c$), —(CH$_2$)$_n$(CHR$^f$)(CH$_2$)$_m$-phenyl, —(CH$_2$)$_n$-(phenyl substituted with 0-3 $R^b$), and —(CH$_2$)$_n$-(5- to 6-membered heterocycle comprising: carbon atoms and 1-4 heteroatoms selected from N, NR$^e$, O, and S(O)$_p$); and wherein said heterocycle is substituted with 0-3 $R^c$;

$R^3$ is independently selected from the group consisting of: H, halogen, CF$_3$, OCF$_3$, C$_{1-6}$ alkyl substituted with 0-3 $R^a$, C$_{2-6}$ alkenyl substituted with 0-3 $R^a$, —CO$_2$(C$_{1-4}$ alkyl), —SO$_2$(phenyl), —(CH$_2$)$_n$—(C$_{3-6}$ cycloalkyl substituted with 0-3 $R^c$), —(CH$_2$)$_n$-(phenyl substituted with 0-3 $R^b$), —(CH$_2$)$_n$-(naphthyl substituted with 0-3 $R^b$), and —(CH$_2$)$_n$-(5- to 10 membered heterocycle comprising: carbon atoms and 1-4 heteroatoms selected from N, NR$^e$, O, and S(O)$_p$); wherein said heterocycle is substituted with 0-3 $R^c$;

$R^4$ is independently selected from the group consisting of: H and C$_{1-4}$ alkyl;

$R^5$ is independently selected from the group consisting of: C$_{3-6}$ cycloalkyl, phenyl, naphthyl, and a 5- to 10-membered heterocycle comprising: carbon atoms and 1-4 heteroatoms selected from N, NR$^e$, O, and S(O)$_p$; and wherein each moiety is substituted with 0-3 $R^d$;

L is independently a hydrocarbon or hydrocarbon-heteroatom linker optionally substituted with 0-2 $R^g$; wherein said hydrocarbon linker is unsaturated and has one to eight carbon atoms; and said hydrocarbon-heteroatom linker may be saturated or unsaturated and has one to seven carbon atoms and one group selected from —CO—, S, —SO—, —SO$_2$—, NH, and N(C$_{1-4}$ alkyl);

$R^a$ is, independently at each occurrence, selected from the group consisting of: halogen, OH, C$_{1-4}$ alkyl, C$_{1-4}$ alkoxy, C$_{1-4}$ haloalkyl, C$_{1-4}$ haloalkoxy, CF$_3$, OCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), NHCO(C$_{1-4}$ alkyl substituted with 0-1 NH$_2$), N(C$_{1-4}$ alkyl) CO(C$_{1-4}$ alkyl), NHCO$_2$(C$_{1-4}$ alkyl), CONHSO$_2$(C$_{1-4}$ alkyl), SO$_2$(C$_{1-4}$ alkyl), CONH$_2$, CONH(C$_{1-4}$ alkyl), NHSO$_2$(C$_{1-4}$ alkyl), N(C$_{1-4}$ alkyl)SO$_2$(C$_{1-4}$ alkyl), and phenoxy;

$R^b$ is, independently at each occurrence, selected from the group consisting of: halogen, OH, C$_{1-4}$ alkyl, C$_{1-4}$ alkoxy, C$_{1-4}$ haloalkyl, C$_{1-4}$ haloalkoxy, CF$_3$, OCF$_3$, OCF$_2$CHF$_2$, OCH$_2$CF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl), NHSO$_2$(C$_{1-4}$ alkyl), N(C$_{1-4}$ alkyl)SO$_2$(C$_{1-4}$ alkyl), SO$_2$(C$_{1-4}$ alkyl), SO$_2$NH$_2$, phenyl, benzyl, and phenoxy;

$R^c$ is, independently at each occurrence, selected from the group consisting of: =O and $R^b$;

$R^d$ is, independently at each occurrence, selected from the group consisting of: halogen, OH, C$_{1-6}$ alkyl, C$_{1-4}$ alkoxy, C$_{1-4}$ haloalkyl, C$_{1-4}$ haloalkoxy, CF$_3$, OCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl), NHSO$_2$(C$_{1-4}$ alkyl), SO$_2$(C$_{1-4}$ alkyl), and SO$_2$NH$_2$;

$R^e$ is, independently at each occurrence, selected from the group consisting of: H, C$_{1-4}$ alkyl, CO(C$_{1-4}$ alkyl), CO$_2$(C$_{1-4}$ alkyl), CO$_2$(benzyl), and —(CH$_2$)$_n$-(phenyl optionally substituted with 0-2 halogens);

$R^f$ is, independently at each occurrence, selected from the group consisting of: C$_{1-4}$ alkyl, C$_{2-4}$ alkenyl, CO$_2$(C$_{1-4}$ alkyl), CONH$_2$, C$_{3-6}$ cycloalkyl, phenyl, and benzyl;

$R^g$ is, independently at each occurrence, selected from the group consisting of: halogen, OH, C$_{1-4}$ alkyl, C$_{2-4}$ alkenyl, C$_{1-4}$ haloalkyl, C$_{1-4}$ alkyoxy, CO$_2$(C$_{1-4}$ alkyl), C$_{3-6}$ cycloalkyl, and phenyl;

m is, independently at each occurrence, selected from 0, 1, and 2;

n is, independently at each occurrence, selected from 0, 1, 2, 3, and 4;

p is, independently at each occurrence, selected from 0, 1, and 2; and s is, independently at each occurrence, selected from 1, 2, 3, and 4.

In a fourth embodiment of the second aspect, the present disclosure provides a compound of Formula (II), or a stereoisomer, a tautomer, a pharmaceutically acceptable salt, or a solvate thereof, wherein:

$R^1$ is C$_{1-4}$ alkyl;

$R^5$ is independently selected from the group consisting of: phenyl, indazolyl, and quinolinyl; and wherein each moiety is substituted with 0-2 $R^d$; and L is independently —C≡CH$_2$—, —(CH$_2$)$_2$—CH(CH=CH$_2$)—, —(CH$_2$)$_2$—CH(cyclopropyl), —(CH$_2$)$_3$—CH(CO$_2$Me), —S—(CH$_2$)$_2$— or —N(Me)(CH$_2$)$_3$—.

In a fifth embodiment of the second aspect, the present disclosure provides a compound of Formula (II), or a stereoisomer, a tautomer, a pharmaceutically acceptable salt, or a solvate thereof, wherein:

$R^1$ is independently selected from the group consisting of: —((CH$_2$)$_s$O)$_n$(C$_{1-4}$ alkyl), —((CH$_2$)$_s$O)$_n$(CH$_2$)$_s$NH$_2$, —((CH$_2$)$_s$O)$_n$(CH$_2$)$_s$CH(C$_{1-4}$ alkyl)(CH$_2$)$_s$(C$_{1-4}$ alkyl), —((CH$_2$)$_s$O)$_n$(CH$_2$)$_s$NHCO(CH$_2$)$_s$NH$_2$, —((CH$_2$)$_s$O)$_n$(CH$_2$)$_s$NHCO$_2$(t-Bu), —((CH$_2$)$_s$O)$_n$(CH$_2$)$_s$NHCO(CH$_2$)$_s$NHCO$_2$(C$_{1-4}$ alkyl), —(CH$_2$)$_s$CONHSO$_2$(C$_{1-4}$ alkyl), C$_{1-6}$ alkyl substituted with 1-3 $R^a$, C$_{1-6}$ alkyl substituted with N$_3$ or SO$_2$OH, —(CH$_2$)$_s$—C$_{3-6}$ cycloalkyl, —(CH$_2$)$_n$—(C$_{3-6}$ cycloalkyl substituted with 1-3 $R^c$), —(CH$_2$)$_n$-(phenyl substituted with SO$_2$NH$_2$ or OCF$_3$), W-(phenyl substituted with 0-3 $R^b$), —W-(pyridyl substituted with 0-3 $R^b$),

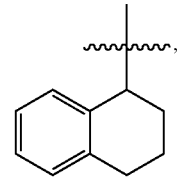 [SMILES: *C1CCCc2ccccc21]

and —(CH$_2$)$_n$-(heterocycle substituted with 0-3 $R^c$); wherein said heterocycle is selected from a group consisting of: tetrahydrofurranyl, pyrazolyl, tetrazolyl, oxadiazolyl, pyrazinyl, benzothiazolyl,

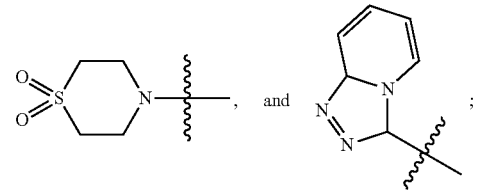 [SMILES: *N1CCS(=O)(=O)CC1 ; *C1N=NC2C=CC=CN12]

alternatively, $R^1$ is —(CH$_2$)$_n$-heterocycle; and wherein said heterocycle is substituted with 1-3 $R^c$ and is selected from a group consisting of: pyrrolidinyl, imidazolyl, and thiazolyl;

W is independently selected from the group consisting of: —(CH$_2$)$_n$(CHR$^f$)(CH$_2$)$_m$—, —(CH$_2$)$_n$CH=CH(CH$_2$)$_m$—, —(CH$_2$)$_s$O(CH$_2$)$_m$—, —(CH$_2$)$_s$NH(CH$_2$)$_m$—, —(CH$_2$)$_s$N(C$_{1-4}$ alkyl)(CH$_2$)$_m$—, —(CH$_2$)$_s$CONH(CH$_2$)$_m$—, —(CH$_2$)$_s$NHCO(CH$_2$)$_m$—, —(CH$_2$)$_s$N(C$_{1-4}$ alkyl)CO(CH$_2$)$_m$—, —(CH$_2$)$_s$NHCONH(CH$_2$)$_m$—, —(CH$_2$)$_s$N(C$_{1-4}$ alkyl)CONH(CH$_2$)$_m$—, and —(CH$_2$)$_s$CONHSO$_2$(CH$_2$)$_m$—;

R$^3$ is independently selected from the group consisting of: H, halogen, C$_{1-6}$ alkyl, and —(CH$_2$)$_n$-phenyl substituted with 0-3 R$^b$;

R$^4$ is H;

R$^5$ is independently selected from the group consisting of: phenyl and naphthyl; wherein each moiety is substituted with 0-3 R$^d$;

L is independently a hydrocarbon or hydrocarbon-heteroatom linker; wherein said hydrocarbon linker is saturated, has one to eight carbon atoms and may be straight or branched; and said hydrocarbon-heteroatom linker is saturated and has one to seven carbon atoms and one O;

R$^a$ is, independently at each occurrence, selected from the group consisting of: halogen, OH, C$_{1-4}$ alkyl, C$_{1-4}$ alkoxy, C$_{1-4}$ haloalkyl, C$_{1-4}$ haloalkoxy, CF$_3$, OCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), NHCO(C$_{1-4}$ alkyl substituted with 0-1 NH$_2$), N(C$_{1-4}$ alkyl)CO(C$_{1-4}$ alkyl), NHCO$_2$(C$_{1-4}$ alkyl), CONHSO$_2$(C$_{1-4}$ alkyl), SO$_2$(C$_{1-4}$ alkyl), CONH$_2$, CONH(C$_{1-4}$ alkyl), NHSO$_2$(C$_{1-4}$ alkyl), N(C$_{1-4}$ alkyl)SO$_2$(C$_{1-4}$ alkyl), and phenoxy;

R$^b$ is, independently at each occurrence, selected from the group consisting of: halogen, OH, C$_{1-4}$ alkyl, C$_{1-4}$ alkoxy, C$_{1-4}$ haloalkyl, C$_{1-4}$ haloalkoxy, CF$_3$, OCF$_3$, OCF$_2$CHF$_2$, OCH$_2$CF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl),
NHSO$_2$(C$_{1-4}$ alkyl), N(C$_{1-4}$ alkyl)SO$_2$(C$_{1-4}$ alkyl), SO$_2$(C$_{1-4}$ alkyl), SO$_2$NH$_2$, phenyl, benzyl, and phenoxy;

R$^c$ is, independently at each occurrence, selected from the group consisting of: =O and R$^b$;

R$^d$ is, independently at each occurrence, selected from the group consisting of: halogen, OH, C$_{1-6}$ alkyl, C$_{1-4}$ alkoxy, C$_{1-4}$ haloalkyl, C$_{1-4}$ haloalkoxy, CF$_3$, OCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl), NHSO$_2$(C$_{1-4}$ alkyl), SO$_2$(C$_{1-4}$ alkyl), and SO$_2$NH$_2$;

R$^f$ is, independently at each occurrence, selected from the group consisting of: C$_{1-4}$ alkyl, C$_{2-4}$ alkenyl, CO$_2$(C$_{1-4}$ alkyl), CONH$_2$, C$_{3-6}$ cycloalkyl, phenyl, and benzyl;

m is, independently at each occurrence, selected from 0, 1, and 2;

n is, independently at each occurrence, selected from 1, 2, 3, and 4; and s is, independently at each occurrence, selected from 1, 2, 3, and 4.

In a sixth embodiment of the second aspect, the present disclosure provides a compound of Formula (II), or a stereoisomer, a tautomer, a pharmaceutically acceptable salt, or a solvate thereof, wherein:

R$^1$ is independently selected from the group consisting of: —CH$_2$CF$_3$, —(CH$_2$)$_2$CF$_3$, —(CH$_2$)$_3$CF$_3$, —(CH$_2$)$_2$CO$_2$H, —CH$_2$CH(CF$_3$)CO$_2$H, —CH$_2$CH(CO$_2$H)CF$_3$, —CH$_2$C(Me)F$_2$, —(CH$_2$)$_2$N$_3$, —(CH$_2$)$_3$O(CH$_2$)$_2$OMe, —(CH$_2$)$_2$O(CH$_2$)$_2$O(CH$_2$)$_2$NH$_2$, —(CH$_2$)$_3$OCH$_2$CH(Et)(CH$_2$)$_3$Me, —(CH$_2$)$_2$O(CH$_2$)$_2$O(CH$_2$)$_2$NHCO(CH$_2$)$_2$NH$_2$, —CH$_2$CONHSO$_2$Me, —(CH$_2$)$_2$SO$_2$OH, —(CH$_2$)$_2$NHCO(i-Bu), —(CH$_2$)$_2$NHCOMe, —(CH$_2$)$_2$NMeCOMe, —(CH$_2$)$_2$NHCO$_2$(t-Bu), —((CH$_2$)$_2$O)$_2$(CH$_2$)$_2$NHCO$_2$(t-Bu), —((CH$_2$)$_2$O)$_3$(CH$_2$)$_2$NHCO$_2$(t-Bu), —((CH$_2$)$_2$O)$_2$(CH$_2$)$_2$NHCO(CH$_2$)$_2$NHCO$_2$(t-Bu), —(CH$_2$)$_2$OPh, —(CH$_2$)$_3$OPh, —(CH$_2$)$_2$NHPh, —(CH$_2$)$_3$N(Me)Ph, cyclopropylmethyl, cyclohexylmethyl, 4-(t-Bu)-cyclohexyl, 4-N(Me)$_2$-cyclohexyl, (tetrahydrofurran-2-yl)methyl, 2-(1-Me-pyrrolidin-2-yl)ethyl, (1-Bn-pyrrolidin-3-yl), (1-Me-pyrazol-3-yl)methyl, 1-Et-pyrazol-5-yl, 1-Me-imidazol-4-yl, (2-Me-imidazol-1-yl)methyl, (4-Ph-thiazol-2-yl)methyl, (5-Ph-1,3,4-oxadiazol-2-yl)methyl, (1H-1,2,3-triazol-4-yl)methyl, (1H-tetrazol-5-yl)methyl-,

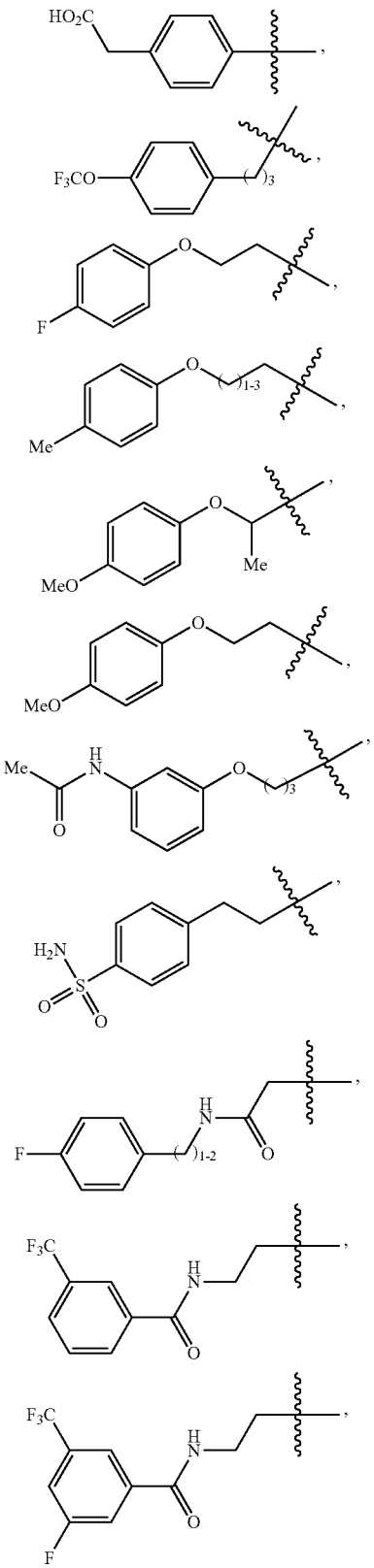

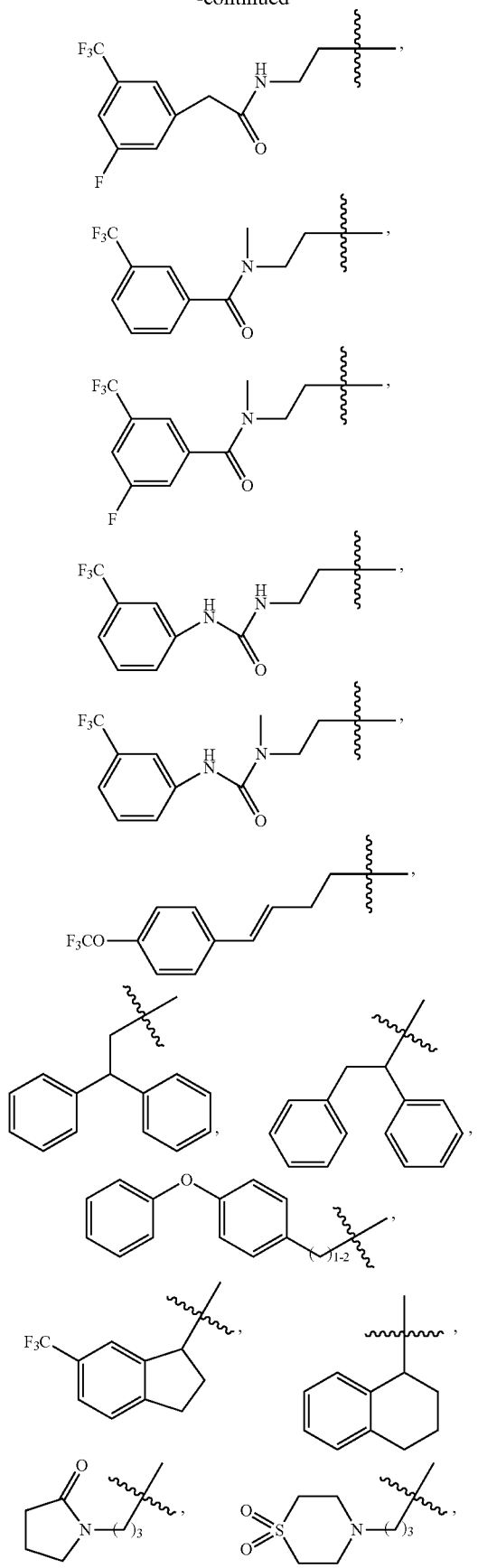
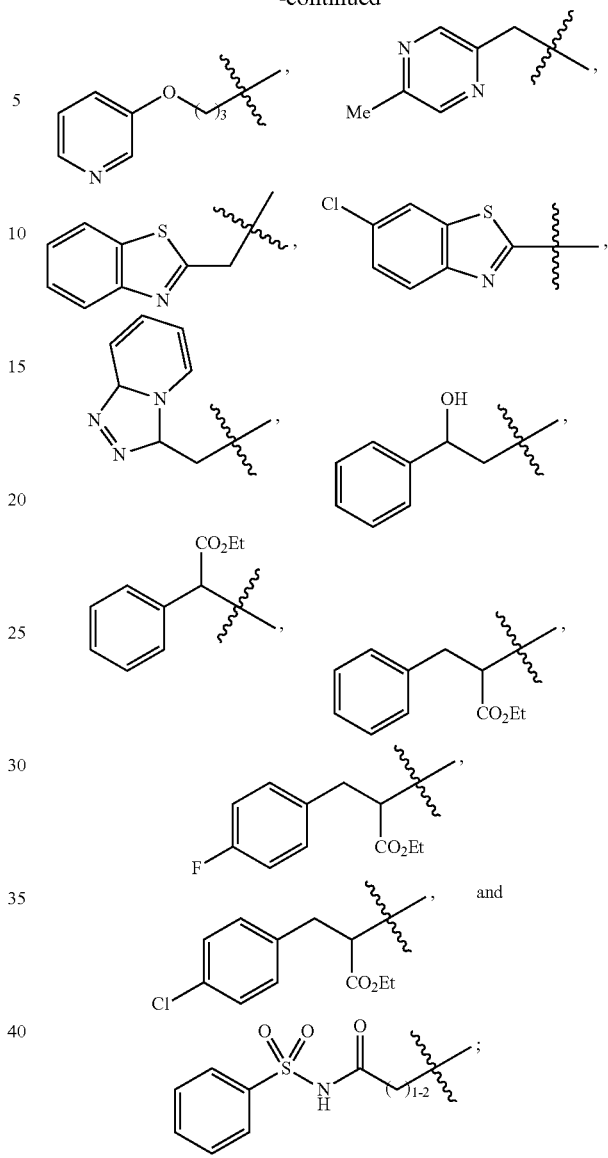

R³ is independently H, methyl or 4-F-phenyl;
R⁴ is H;
R⁵ is independently 2,6-diCl-phenyl or 3,4-diCl-phenyl; and
L is independently —(CH₂)₂—, —(CH₂)₃— or —(CH₂)₂CHMe-.

In a seventh embodiment of the second aspect, the present disclosure provides a compound of Formula (II), or a stereoisomer, a tautomer, a pharmaceutically acceptable salt, or a solvate thereof, wherein:

$R^1$ is independently selected from the group consisting of: H, $C_{1-6}$ alkyl substituted with 0-3 $R^a$, and —$(CH_2)_n$-(phenyl substituted with 0-3 $R^b$);

$R^3$ is independently selected from the group consisting of: —$CO_2(C_{1-4}$ alkyl), —$(CH_2)_n$-(thiadiazolyl substituted with 0-1 $R^b$), and —$(CH_2)_n$—$(N—C_{1-4}$ alkyl-imidazolyl);

$R^4$ is H;

$R^5$ is independently selected from the group consisting of: phenyl and naphthyl; wherein each moiety is substituted with 0-3 $R^d$;

L is independently a hydrocarbon or hydrocarbon-heteroatom linker; wherein said hydrocarbon linker is saturated, has one to eight carbon atoms and may be straight or branched; and said hydrocarbon-heteroatom linker is saturated and has one to seven carbon atoms and one O;

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $SO_2(C_{1-4}$ alkyl), phenyl, benzyl, and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO(C_{1-4}$ alkyl), $NHSO_2(C_{1-4}$ alkyl), $SO_2(C_{1-4}$ alkyl), $SO_2NH_2$, phenyl, benzyl, and phenoxy;

$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, and $CO_2(C_{1-4}$ alkyl); and n, at each occurrence, is selected from 1, 2, 3, and 4.

In an eighth embodiment of the second aspect, the present disclosure provides a compound of Formula (II), or a stereoisomer, a tautomer, a pharmaceutically acceptable salt, or a solvate thereof, wherein:

$R^1$ is independently selected from the group consisting of: methyl and phenyl;

$R^3$ is independently selected from the group consisting of: —$CO_2Me$, 1,2,3-thiadiazol-4-yl, and N-methyl-imidazol-4-yl;

$R^4$ is H;

$R^5$ is 3,4-diCl-phenyl; and

L is —$(CH_2)_3$—.

In a third aspect, the present disclosure provides compounds of Formula (III):

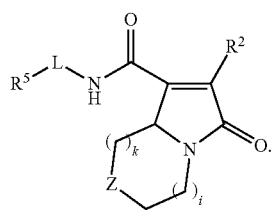

(III)

In a first embodiment of the third aspect, the present disclosure provides a compound of Formula (III), or a stereoisomer, a tautomer, a pharmaceutically acceptable salt, or a solvate thereof, wherein:

$R^2$ is independently selected from the group consisting of: $OR^6$, CN, and $NR^7R^8$;

$R^5$ is independently selected from the group consisting of: $C_{3-6}$ cycloalkyl, phenyl, naphthyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

$R^6$ is independently selected from the group consisting of: H and $C_{1-6}$ alkyl substituted with 0-1 $CO_2H$;

$R^7$ is independently selected from the group consisting of: H, $C_{1-6}$ alkyl substituted with 0-1 $R^a$, —$(CH_2)_n$-(phenyl substituted with 0-3 $R^b$), and —$(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: H and $C_{1-6}$ alkyl;

alternatively, $NR^7R^8$ is a 5- to 6-membered heterocycle comprising: carbon atoms and 1-4 heteroatoms selected from N, $NR^e$, O, and $S(O)_p$;

L is independently a hydrocarbon or hydrocarbon-heteroatom linker optionally substituted with 0-2 $R^g$; wherein said hydrocarbon linker has one to eight carbon atoms and may be straight or branched, saturated or unsaturated; and said hydrocarbon-heteroatom linker has one to seven carbon atoms and one group selected from O, —CO—, S, —SO—, —$SO_2$—, NH, and $N(C_{1-4}$ alkyl);

Z is independently selected from the group consisting of: $CH_2$, $CH(C_{1-4}$ alkyl), $C(C_{1-4}$ alkyl)$_2$, O, CO, S, SO, $SO_2$, NH, $N(C_{1-4}$ alkyl), NHCO, CONH, $SO_2NH$, and $NHSO_2$;

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)$CO(C_{1-4}$ alkyl), $NHCO_2(C_{1-4}$ alkyl), $CONHSO_2(C_{1-4}$ alkyl), $SO_2(C_{1-4}$ alkyl), $CONH_2$, $CONH(C_{1-4}$ alkyl), $NHSO_2(C_{1-4}$ alkyl), $N(C_{1-4}$ alkyl)$SO_2(C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2(C_{1-4}$ alkyl), $NHSO_2(C_{1-4}$ alkyl), $N(C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2(C_{1-4}$ alkyl), $NHSO_2(C_{1-4}$ alkyl), $SO_2(C_{1-4}$ alkyl), and $SO_2NH_2$;

$R^e$ is, independently at each occurrence, selected from the group consisting of: H, $C_{1-4}$ alkyl, $CO(C_{1-4}$ alkyl), $CO_2(C_{1-4}$ alkyl), $CO_2$(benzyl), and —$(CH_2)_n$-(phenyl optionally substituted with 0-2 halogens);

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

k is 1 or 2;

i is 0, 1, or 2;

n, at each occurrence, is selected from 0, 1, 2, 3, and 4; and p, at each occurrence, is selected from 0, 1, and 2.

In a second embodiment of the third aspect, the present disclosure provides a compound of Formula (III), or a stereoisomer, a tautomer, a pharmaceutically acceptable salt, or a solvate thereof, wherein:

$R^2$ is OH;

$R^5$ is 3,4-diCl-phenyl;

L is —$(CH_2)_3$— or —$(CH_2)_2CH(Me)$—;

Z is selected from the group consisting of: $CH_2$ and NHCO;

k is 1; and i is 1 or 2.

In another aspect, the present invention provides a compound selected from the exemplified examples or a stereoisomer, a tautomer, a pharmaceutically acceptable salt, or a solvate thereof, within the scope of the first, second or third aspect.

In another aspect, the present invention provides a compound selected from any subset list of the exemplified examples or any one of the exemplified examples or a stereoisomer, a tautomer, a pharmaceutically acceptable salt, or a solvate thereof, within the scope of the first, second or third aspect.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]

bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl," "$C_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH), as shown in the following equation:

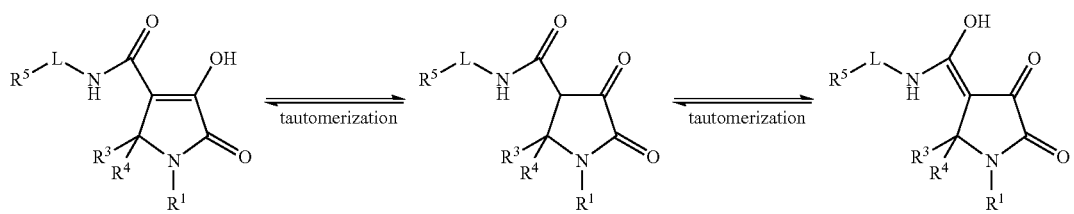

Likewise, an imine (—CH—C=NHR) group in a molecule may tautomerize to its enamine form (—C=C—NHR), as shown in the following equation:

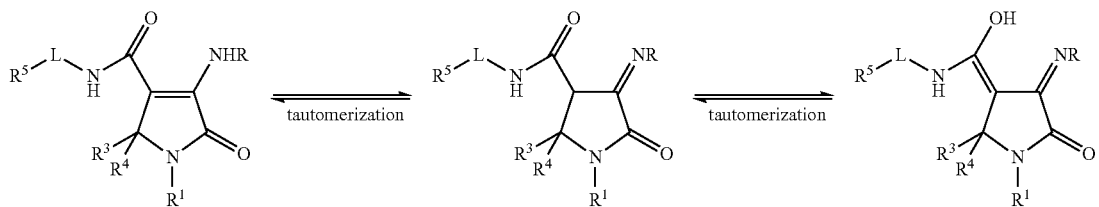

Thus, this disclosure is intended to cover all possible tautomers even when a structure depicts only one of them.

As a person of ordinary skill in the art would be able to understand, when $R^3$ and $R^4$ are different in a compound of Formula (I) or Formula (II), the carbon atom to which both $R^3$ and $R^4$ are attached would be a stereogenic center. The same principle applies to Formula (III) when $R^3$ is not hydrogen. Absent other stereogenic centers on other R groups, the compound would have two enantiomers. For example, when $R^3$ is methyl and $R^4$ is hydrogen, the two enantiomers can be represented by the following (R—) and (S—) configurations:

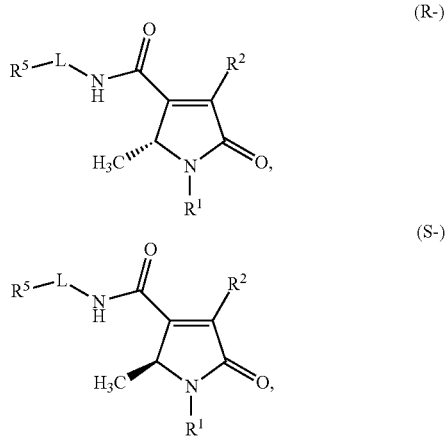

Likewise, a compound of Formula (IV) may exist in the following two different configurations with respect to the stereogenic center indicated:

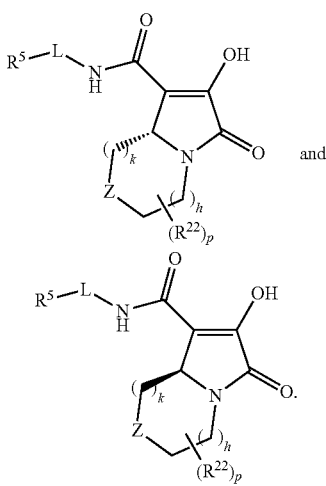

The same principle also applies to the stereogenic centers that may exist in the R groups of the compounds. When two or more stereogenic centers exist in a compound, the compound may exist as enantiomers or diastereomers. Thus, this disclosure is intended to cover all possible stereoisomers even when a single stereoisomer, or no stereochemistry, is described in a structure.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I), Formula (II), Formula (III), or Formula (IV) may have prodrug forms. Any compound that will be converted in vivo to provide the bioactive agent (i.e., a compound of Formula (I), Formula (II), Formula (III), or Formula (IV)) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," A *Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988); and
e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mw" for microwave, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$AlCl_3$ aluminum chloride
$BBr_3$ boron tribromide
$BCl_3$ boron trichloride
BOP reagent benzotriazol-1-yloxytris(dimethylamino)phosphonium hexafluorophosphate
Cbz carbobenzyloxy
$CH_2Cl_2$ dichloromethane
$CH_3CN$ or ACN acetonitrile
$CDCl_3$ deutero-chloroform
$CDCl_3$ chloroform
mCPBA or m-CPBA meta-chloroperbenzoic acid
$Cs_2CO_3$ cesium carbonate
$Cu(OAc)_2$ copper (II) acetate
DCE 1,2 dichloroethane
DCM dichloromethane
DEA diethylamine
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane EDC N-(3-dimthylaminopropyl)-N'-ethylcarbodiimide
EDTA ethylenediaminetetraacetic acid
$Et_3N$ or TEA triethylamine
EtOAc ethyl acetate
$Et_2O$ diethyl ether
EtOH ethanol
HCl hydrochloric acid
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
NIS N-iodosuccinimide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
$PS-Pd(Ph_3)_4$ tetrakis(triphenylphosphine)palladium (0) on polystyrene support
i-PrOH or IPA isopropanol
PS polystyrene
PyBOP (benzotriazol-1-yloxy)tripyrrolidinophosphonium hexafluorophosphate
$SiO_2$ silica oxide
$SnCl_2$ tin(II) chloride
TBAF tetra-n-butylammonium fluoride
TBAI tetra-n-butylammonium iodide
TEA triethylamine
TFA trifluoroacetic acid
THF tetrahydrofuran
$TMSCHN_2$ trimethylsilyldiazomethane
Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The Compounds of the present invention may be prepared by the exemplary processes described in the following schemes and working examples, as well as relevant published literature procedures that are used by one skilled in the art. Exemplary reagents and procedures for these reactions appear hereinafter and in the working examples. Protection and de-protection of functional groups in the processes below may be carried out by procedures generally known in the art (see, for example, Greene, T. W. et al., *Protecting Groups in Organic Synthesis*, 3rd Edition, John Wiley & Sons, Inc., New York (1999)). General methods of organic synthesis and functional group transformations are found in: *Comprehensive Organic Synthesis: Selectivity, Strategy & Efficiency in Modern Organic Chemistry*, B. M. Trost et al., eds., Pergamon Press, New York, N.Y. (1991); March, J., *Advanced Organic Chemistry: Reactions, Mechanisms, and Structure*, 4th Edition, Wiley & Sons, New York, N.Y. (1992); *Comprehensive Organic Functional Groups Transformations*, $1^{st}$ Edition, A. R. Katritzky et al., eds. Elsevier Science Inc. Tarrytown, N.Y. (1995); Larock, R. C., *Comprehensive Organic Transformations*, VCH Publishers, Inc., New York, N.Y. (1989); and references therein.

Solvents, temperatures, pressures, and other reaction conditions may readily be selected by one of ordinary skill in the art. Starting materials are commercially available or can be readily prepared by one of ordinary skill in the art using known methods. For all of the schemes and compounds described below the variables are as described above, unless otherwise indicated. The following are the definitions of symbols used throughout Schemes 1 through 6:

PG: suitable nitrogen protecting group, exemplified by benzyl-(Bn), tert-butoxycarbonyl-(Boc), phthalimide (Phth), tert-butyldimethylsilyl-(TBDMS).

LG: leaving group exemplified by halogen (Cl, Br, I) and sulfonates (—$OS(O)_2$-aryl (e.g., —$OS(O)_2$Ph or —$OS(O)_2C_6H_4CH_3$-p), or —$OS(O)_2$-alkyl (e.g., —$OS(O)_2CH_3$ or —$OS(O)_2CF_3$)).

Scheme 1

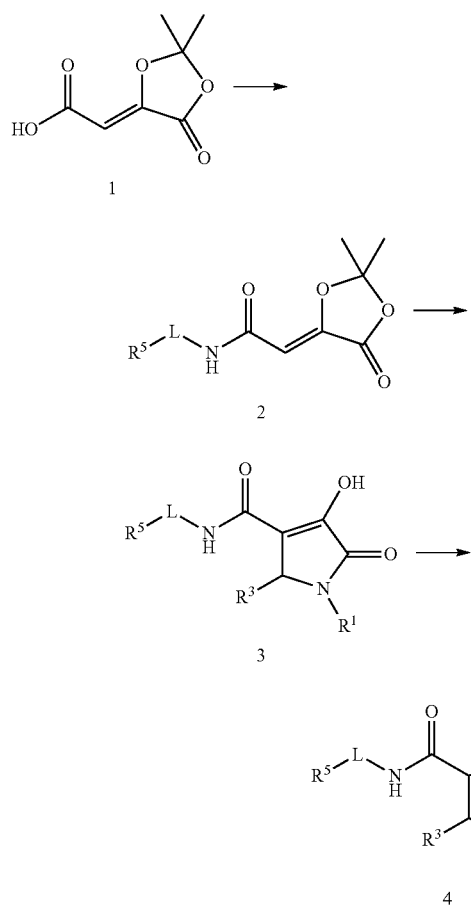

Scheme 2

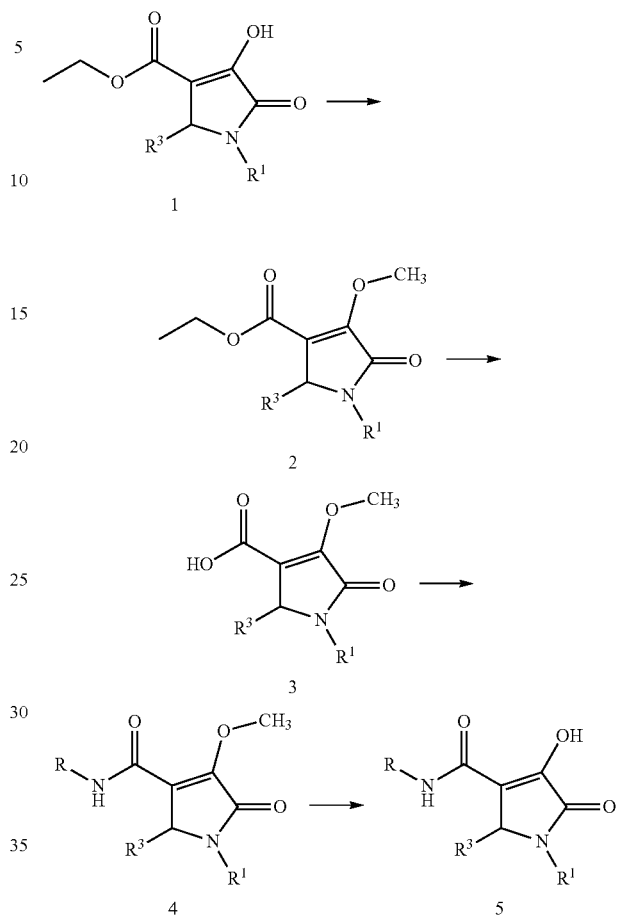

Compounds of formula 4 and of formula 3 may be synthesized according to Scheme 1. (Z)-2-(2,2-dimethyl-5-oxo-1,3-dioxolan-4-ylidene)acetic acid (1), which is synthesized according to methods described in WO 2004/004657, is condensed with an amine, $R^5$-L-$NH_2$, using standard peptide coupling protocols. The protocols include, but are not limited to, formation of the acid chloride of 1 using oxalyl chloride and catalytic DMF in the presence of a suitable solvent such as methylene chloride, followed by addition of $R^5$-L-$NH_2$ in the presence of a base such as TEA, DIPEA or N-methylmorpholine or formation of the active ester of 1 using EDC, HOBt and a base, such as TEA, DIPEA or N-methylmorpholine, in the presence of $R^5$-L-$NH_2$. The amides thus formed are combined with the Schiff base formed by the combination of an amine ($R^1NH_2$) and an aldehyde ($R^3CHO$) in a suitable solvent such as methanol, and heated to effect condensation of the Schiff base with intermediates of formula 2 to form compounds of formula 3. Typically, the reactions are heated to 100° C. using microwave irradiation. Compounds of formula 4 may be synthesized by heating compounds of formula 3 with an amine $NHR^7R^8$ and an acid, such as HOAc, in a suitable solvent such as EtOH to 140° C. using microwave irradiation. Other temperatures and methods of heating may be employed.

Compounds of formula 5 may also be synthesized according to Scheme 2. Thus, compounds of formula 2 may be accessed by O-alkylation of compounds of formula 1 using, for example, trimethylsilyldiazomethane in a suitable solvent such as acetonitrile at room temperature. Hydrolysis of the ester moiety of compounds of formula 2 using, for example, sodium hydroxide or lithium hydroxide in a suitable solvent such as methanol or THF containing water at room temperature provides carboxylic acids of formula 3, which can be condensed with amines to form amides of formula 4 using standard amide coupling conditions (e.g., EDC, HOBt and a base such as TEA, DIPEA or N-methylmorpholine in, for example, DMF or DCM). Demethylation of the methoxy group of compounds of formula 4 provides compounds of formula 5 may be achieved using, for example, boron tribromide or boron trichloride in a suitable solvent such as dichloromethane at room temperature.

Scheme 3

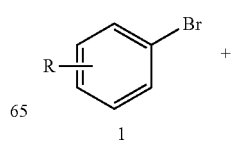

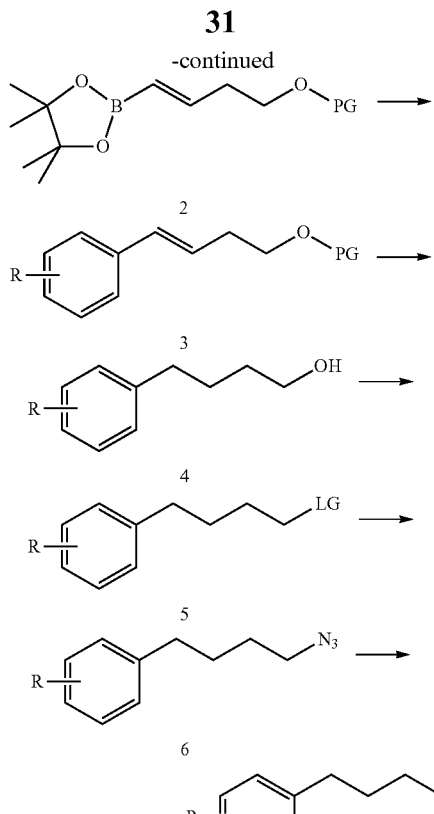

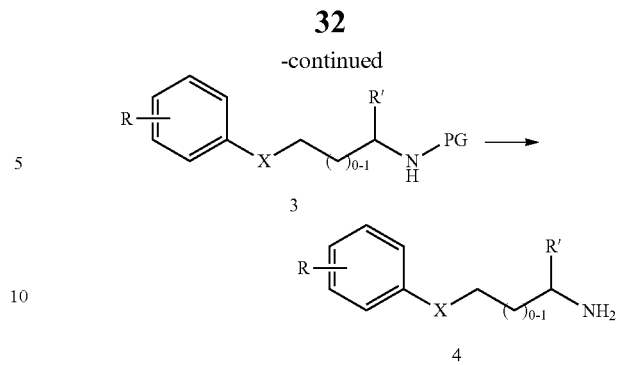

Amines of formula 7 which are not commercially available can be synthesized according to Scheme 3. Compounds of formula 1 can be cross coupled with compounds of formula 2 using, for example, palladium(II) acetate, 2-(di-tert-butylphosphino)biphenyl and potassium fluoride in THF at room temperature. Removal of the protecting group from compounds of formula 3 to give compounds of formula 4 can be carried out using, for example, TBAF when the protecting group is TBDMS. Other suitable protection groups for the alcohol may be employed as described in Greene, T. W. et al., *Protecting Groups in Organic Synthesis*, 3$^{rd}$ Edition, John Wiley & Sons, Inc., New York (1999). The alcohol contained in compounds of formula 4 is activated through conversion to a leaving group. For example, the alcohol may be treated with methanesulfonyl chloride and a base, such as TEA, in a suitable solvent such as $CH_2Cl_2$. Displacement of the leaving group of compounds of formula 5 with, for example, sodium azide in a suitable solvent such as DMF gives compounds of formula 6, which are reduced with, for example, platinum (IV) oxide and hydrogen gas in a suitable solvent such as EtOAc to give amines of formula 7. Other reducing conditions which are known to those skilled in the art may be applied.

Scheme 4

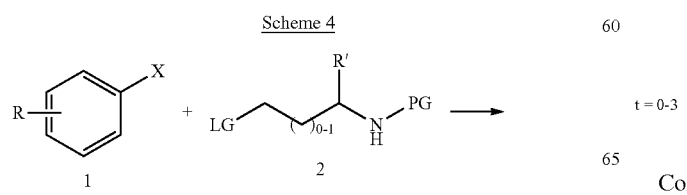

Amines of formula 4 may be synthesized according to Scheme 4. Phenols (X=OH) or thiols (X=SH) of formula 1 may be coupled to amines of formula 2, wherein R'=H or Me, suitably protected with, for example, phthalimide or Boc, and containing a leaving group such as bromide. The reaction takes place in the presence of a base such as $Cs_2CO_3$ in a suitable solvent such as DMF. Removal of the protecting group from compounds of formula 3 provides amines of formula 4. When the protecting group is a phthalimide, the typical deprotection procedure employs hydrazine monohydrate in a suitable solvent such as EtOH. When a Boc group is employed as the protecting group, it is typically removed using, for example, 10% TFA in a suitable solvent such as DCM.

Scheme 5

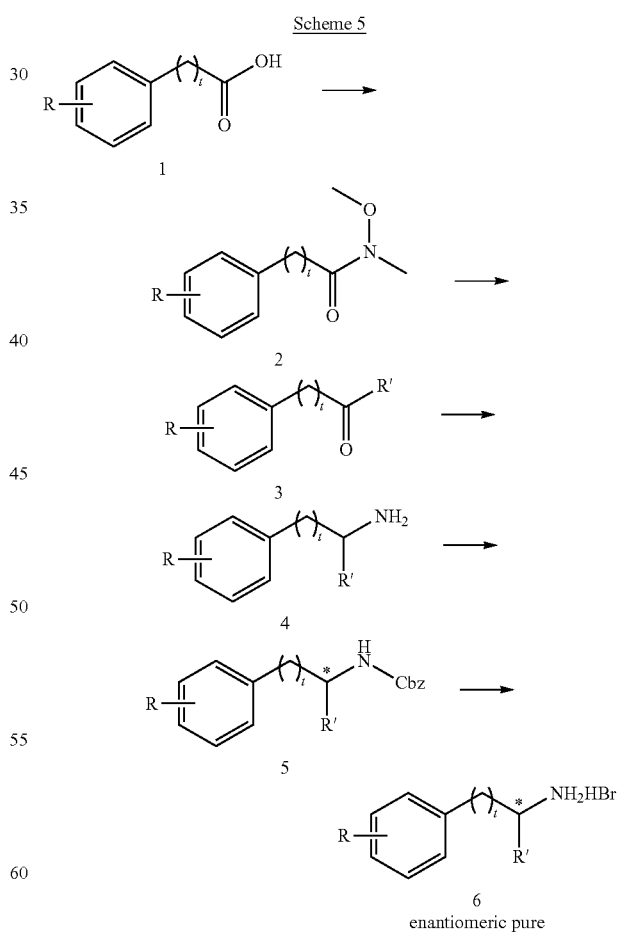

t = 0-3

Compounds of formula 1 in Scheme 5, which can be either commercially available or synthesized according to methods known in the art of organic synthesis, can be coupled with Weinreb amines using standard peptide coupling methods to give compounds of formula 2. The Weinreb amides can then be converted to ketones of formula 3 by treatment with Grignard reagents, where R' can be any alkyl, aryl or heteroaryl groups and R' can be optionally substituted. Reductive amination by treatment with reagents such as ammonium acetate and sodium cyanoborohydride can afford α-substituted amines of formula 4. The racemic amines can be protected with Cbz group and at this stage, two enantiomers can be separated via preparative chiral HPLC separation (formula 5). Deprotection using hydrobromic acid can provide enantiomeric pure amine HBr salts of formula 6.

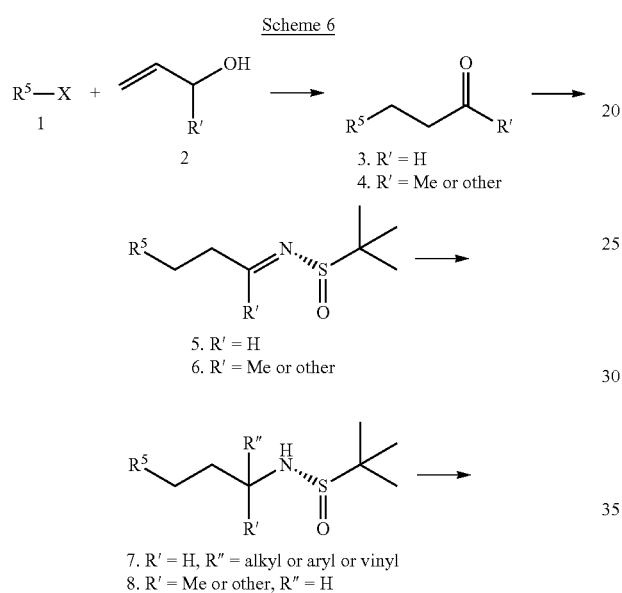

Scheme 6

7. R' = H, R" = alkyl or aryl or vinyl
8. R' = Me or other, R" = H

9. R' = H, R" = alkyl or aryl or vinyl
10. R' = Me or other, R" = H

Scheme 6 exemplifies an alternative route of synthesis of alpha-substituted alkyl amines of formula 9 and 10. Compounds of formula 3 and 4 are either commercially available or can be readily prepared from commercially available materials by methods described in Scheme 6. For example, Heck reaction of the corresponding aryl halides (bromide or iodide) of formula 1 with the alcohols of formula 2 can give the corresponding aldehydes of formula 3 or ketones of formula 4. Subsequent reaction with enantiomerically pure 2-methylpropane-2-sulfinamide can form imines of formula 5 and 6. When R'=H, compounds of formula 5 can be converted to enantiopure sulfonamide of formula 7 with a high stereoselectivity via treatment with Grignard Reagents. When R' is substituent other than H, compounds of formula 6 can be reduced to enantiopure sulfinamides of formula 8 using NaBH₄ or L-selectride. Subsequent cleavage of sulfinyl moiety can afford corresponding enantiomerically pure α-substituted amines of formula 9 and 10.

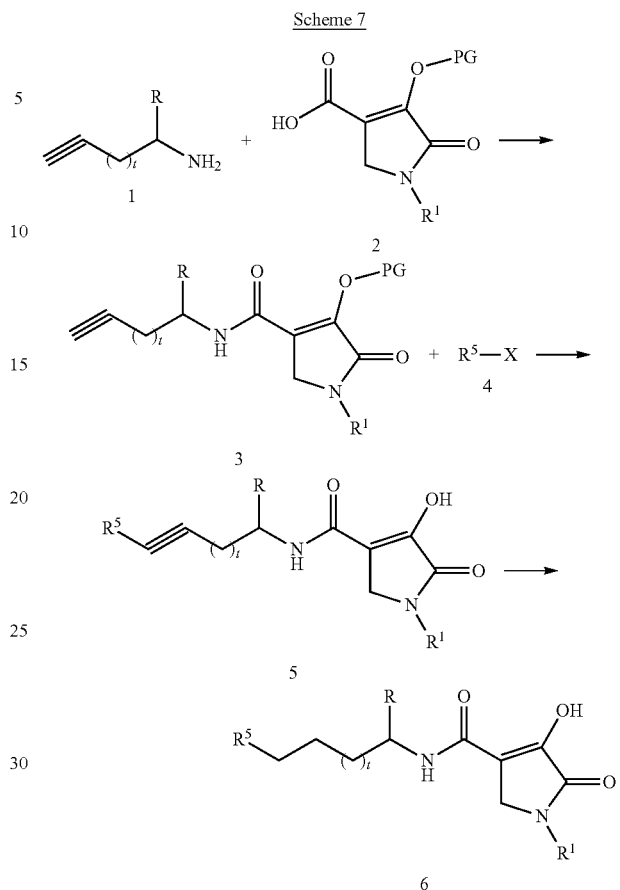

Scheme 7

Compounds of formula 6 can be synthesized as illustrated in Scheme 7 where t can be 0-3. The starting materials of formula 2 can be readily synthesized by method described in Philip Southwick et al, *Journal of Org. Chem.*, 1087-1095 (1956) and by the method described in Intermediate 9, or alternatively, it can be synthesized by protocol described in Scheme 9. Through standard peptide coupling method, amines of formula 1 and acids of formula 2 can be converted to amides of formula 3. These compounds, together with other starting material halides (formula 4) can undergo Sonagoshira reaction to afford compounds of formula 5. Hydrogenation of the acetylene using palladium on carbon can then give desired compounds of formula 6.

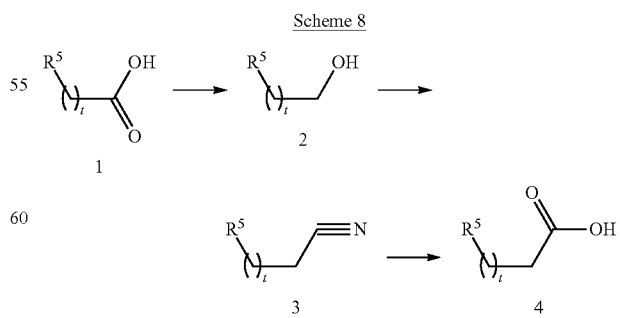

Scheme 8

Scheme 8 illustrated the synthesis of compounds of formula 4, where t can be 0-6. Acids of formula 1 can be reduced to alcohols using conventional method known in the art of organic synthesis. Then mesylation of alcohol and displacement with nitrile group can give compounds of formula 3. Then compounds of formula 3 can undergo hydrolysis using basic aqueous condition to give desired homologated acids of formula 4.

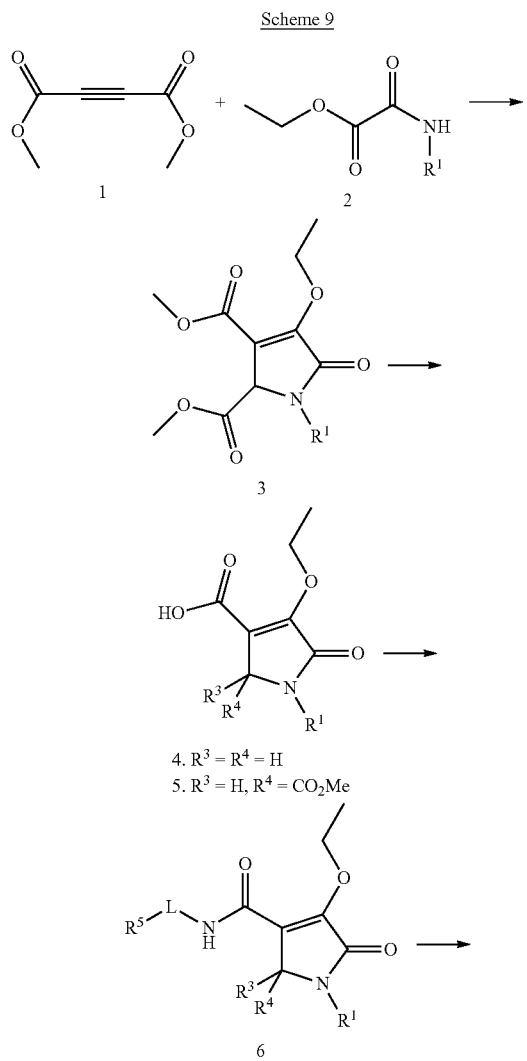

methylene chloride, 1,2-dichloroethane, ethyl acetate, DMSO, etc., at 0-80° C. Saponification and decarboxylation of compounds of formula 3 by heating with aqueous LiOH or NaOH in MeOH and/or THF can give compounds of formula 4 (where $R^3=R^4=H$), or compounds of formula 5 (where $R^3=H$, $R^4=CO_2Me$). The monoacids of formula 4 or 5 can be condensed with an amine, using standard peptide protocols, to afford amides of formula 6. Removal of ethoxy group by standard deprotection procedures known to those skilled in the art gives the compounds of formula 7.

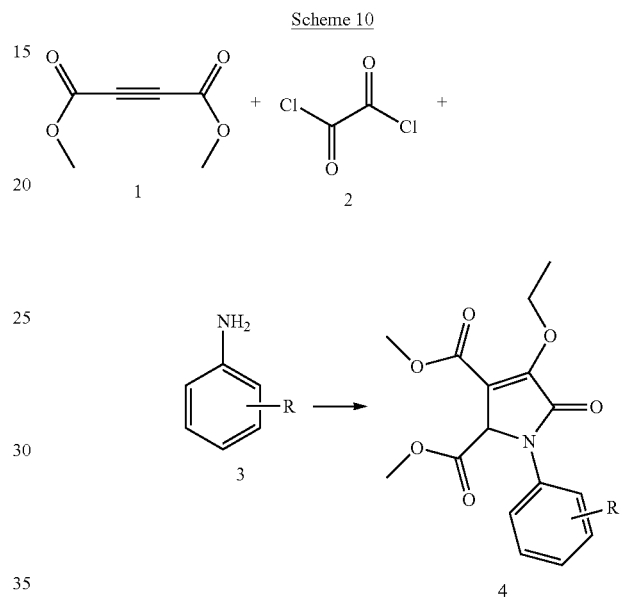

Alternatively to Scheme 9, compounds of formula 4 may also be synthesized according to Scheme 10, using the modified protocols described in Anary-Abbasinejad, M. et al, *Journal of Chemical research,* 574-576 (2007), from commercially available triphenylphosphine, dimethyl but-2-ynedioate, oxalyl dichloride, and anilines, where R could be any substitution, in a suitable solvent, such as DCM.

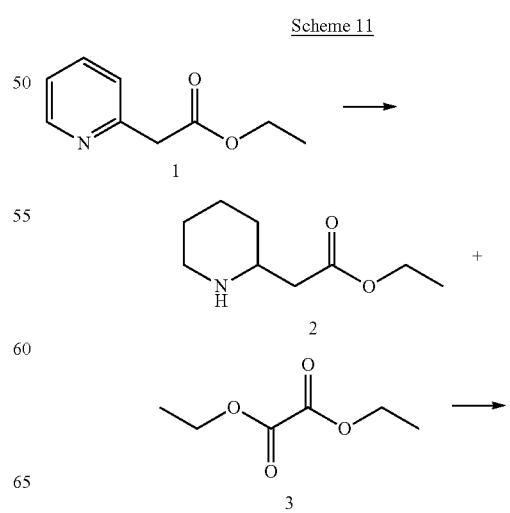

Compounds of formula 7 may be synthesized according to Scheme 9. Compounds of formula 2, where $R^1$=alkyl or aryl or heteroaryl, can be synthesized from ethyl oxalylchloride and aliphatic or aromatic amines by using methods generally known in the art. Compounds of formula 3, which can be synthesized according to modified methods described in Yavari, Issa et al, *Synthetic Communications,* 2527-2534 (2002), from triphenylphosphine, dimethyl but-2-ynedioate, and compounds of formula 2 in a variety of solvents, such as

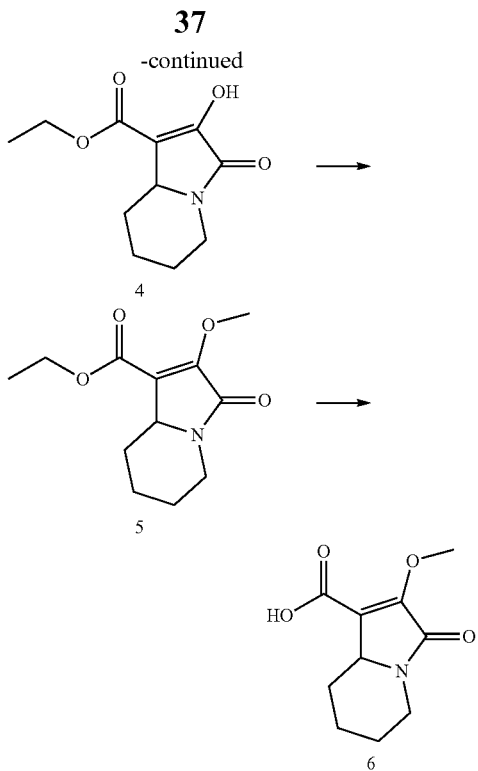

Compounds of formula 1 in Scheme 11, which can either be commercially available or synthesized according to methods known in the art of organic synthesis, can be hydrogenated over either rhodium on alumina catalyst or platinum (IV) oxide to afford the amino ester 2. Compound 2 can be combined with diethyl oxalate, compound 3, to afford the monocycle 4, which is methylated using conditions generally known in the art. Saponification of the ethyl ester using known methods can afford acid of formula 6.

General Methods

The following methods were used in the exemplified Examples, except where noted otherwise.

Analytical HPLC and LC/MS Methods Employed in Characterization of Examples

Reverse phase analytical HPLC/MS was performed on Shimadzu LC10AS systems coupled with Waters ZMD Mass Spectrometers (Methods A-C, E and F) or Waters Aquity system coupled with a Waters Micromass ZQ Mass Spectrometer (Method D). Chiral analytical LC was performed on a Berger Analytical SFC instrument (Method G).

Method A: Linear gradient of 0 to 100% B over 4 min, with 1 min hold at 100% B;
 UV visualization at 220 nm
 Column: Phenomenex Luna C18 4.6×50 mm
 Flow rate: 4 mL/min
Solvent A: 0.1% trifluoroacetic acid, 90% water, 10% acetonitrile
Solvent B: 0.1% trifluoroacetic acid, 90% acetonitrile, 10% water.
Method B: Linear gradient of 0 to 100% B over 4 min, with 1 min hold at 100% B;
 UV visualization at 220 nm
 Column: Phenomenex Luna C18 4.6×50 mm
 Flow rate: 4 mL/min
Solvent A: 10 mM ammonium acetate, 90% water, 10% acetonitrile
Solvent B: 10 mM ammonium acetate, 90% acetonitrile, 10% water.
Method C. Linear gradient of 0 to 100% B over 4 min, with 1 min hold at 100% B;
 UV visualization at 220 nm;
 Column: PHENOMENEX® Luna C18 4.6×50 mm;
 Flow rate: 4 mL/min;
Solvent A: 10 mM ammonium acetate, 90% water, 10% methanol;
Solvent B: 10 mM ammonium acetate, 90% methanol, 10% water.
Method D. Linear gradient of 2 to 98% B over 1 min, with 0.5 min hold time at 98% B;
 UV visualization at 220 nm;
 Column: Waters BEH C18 2.1×50 mm;
 Flow rate: 0.8 mL/min;
Solvent A: 0.05% TFA, 100% water;
Solvent B: 0.05% TFA, 100% ACN.
Method E. Linear gradient of 0 to 100% B over 4 min, with 1 min hold time at 100% B;
 UV visualization at 220 nm;
 Column: Ascentis Express 4.6×50 C18 at 45° C.;
 Flow rate: 4 mL/min;
Solvent A: 10 mM ammonium acetate, 5% ACN, 95% water;
Solvent B: 10 mM ammonium acetate, 95% ACN, 5% water.
Method F. Linear gradient of 0 to 100% B over 8 min, with 1 min hold at 100% B;
 UV visualization at 220 nm;
 Column: PHENOMENEX® Luna C18 4.6×75 mm;
 Flow rate: 2.5 mL/min;
Solvent A: 10 mM ammonium acetate, 90% water, 10% methanol;
Solvent B: 10 mM ammonium acetate, 90% methanol, 10% water.
Method G. Isocratic 80/20 $CO_2$/MeOH containing 0.1% DEA;
 UV visualization at 220 nm;
 Column: CHIRALPAK® AC, 250×4.6 mm, 10 µM;
 Flow rate: 3.0 mL/min.

Preparative HPLC Methods Employed in the Purification of Products

Method H. Linear gradient of 0 to 100% B over 10 min, with 5 min hold time at 100% B; Shimadzu LC-8A binary pumps; Waters ZQ mass spectrometer using Waters Masslynx 4.0 SP4 MS software;
 UV visualization at 220 nm;
 Column: Waters SunFire 19×100 mm 5 µm C18;
 Flow rate: 20 mL/min;
 Peak collection triggered by mass spectrometry;
Solvent A: 0.1% TFA, 10% ACN, 90% water;
Solvent B: 0.1% TFA, 90% ACN, 10% water.
Method I. Linear gradient of 20 to 100% B over 10 min, with 5 min hold time at 100% B; Shimadzu LC-8A binary pumps; Shimadzu SPD-20A UV detector;
 UV visualization at 220 nm;
 Column: PHENOMENEX® Luna AXIA 21.1×100 mm 5 µm C18;
 Flow rate: 20 mL/min;
 Peak collection triggered by UV absorbance;
Solvent A: 0.1% TFA, 10% MeOH, 90% water;
Solvent B: 0.1% TFA, 90% MeOH, 10% water.
Method J. Linear gradient of 20 to 100% B over 10 min, with 2 min hold time at 100% B; Shimadzu LC-8A binary pumps; Shimadzu SPD-10A UV detector;

UV visualization at 220 nm;
Column: PHENOMENEX® Luna AXIA 21.1×100 mm 5 μm C18;
  Flow rate: 20 mL/min;
  Peak collection triggered by UV absorbance;
  Solvent A: 0.1% TFA, 10% ACN, 90% water;
  Solvent B: 0.1% TFA, 90% ACN, 10% water.
Method K. Isocratic 80/20 $CO_2/CH_3OH$ containing 0.1% DEA; Berger Multigram II SFC instrument;
  UV visualization at 220 nm;
  Column: CHIRALPAK® AD-H, 250×21 cm ID, 5 μm;
  Flow rate: 65 mL/min;
  Peak collection triggered by UV absorbance.
LCMS Analytical Method
Method L. Linear gradient of 0 to 100% B over 2 min, with 1 min hold at 100% B;
  UV visualization at 220 nm
  Column: Phenomenex Luna C18 2.0×30 mm
  Flow rate: 1 mL/min
Solvent A: 0.1% trifluoroacetic acid, 90% water, 10% methanol
Solvent B: 0.1% trifluoroacetic acid, 90% methanol, 10% water.
Method M. Linear gradient of 0 to 100% B over 2 min, with 1 min hold at 100% B;
  UV visualization at 220 nm
  Column: Phenomenex Luna C18 2.0×30 mm
  Flow rate: 1 mL/min
Solvent A: 0.1% trifluoroacetic acid, 90% water, 10% acetonitrile
Solvent B: 0.1% trifluoroacetic acid, 90% acetonitrile, 10% water.
Method N. Linear gradient of 0 to 100% B over 4 min, with 1 min hold at 100% B;
  UV visualization at 220 nm;
  Column: PHENOMENEX® Luna C18 4.6×50 mm;
  20 Flow rate: 4 mL/min;
Solvent A: 0.1% trifluoroacetic acid, 90% water, 10% MeOH;
Solvent B: 0.1% trifluoroacetic acid, 90% MeOH, 10% water.
Method O. Linear gradient of 0 to 100% B over 2 min, with 1 min hold at 100% B;
  UV visualization at 220 nm
  Column: Phenomenex Luna C18 2.0×30 mm
  Flow rate: 1 mL/min
Solvent A: 0.1% formic acid, 90% water, 10% methanol
Solvent B: 0.1% formic acid, 90% methanol, 10% water.
Method P. Linear gradient of 0 to 100% B over 4 min, with 1 min hold at 100% B;
  UV visualization at 220 nm
  Column: Mac-Mod Halo C18, 4.6×50 mm
  Flow rate: 4 ml/min
Solvent A: 10 mM ammonium acetate, 95% water, 5% ACN
Solvent B: 10 mM ammonium acetate, 95% ACN, 5% water
  Method Q. Linear gradient of 0 to 100% B over 4 min, with 1 min hold at 100% B;
  UV visualization at 220 nm;
  Column: Waters XBridge C18, 4.6×50 mm, 5 μm;
  20 Flow rate: 4 mL/min;
Solvent A: 0.05% trifluoroacetic acid, 95% water, 5% MeOH;
Solvent B: 0.05% trifluoroacetic acid, 95% MeOH, 5% water.
Method R. Linear gradient of 0 to 100% B over 2 min, with 1 min hold at 100% B;
  UV visualization at 220 nm;
  Column: PHENOMENEX® Luna C18 4.6×50 mm;
  Flow rate: 5 mL/min;
Solvent A: 10 mM ammonium acetate, 90% water, 10% methanol;
Solvent B: 10 mM ammonium acetate, 90% methanol, 10% water.
PrepHPLC Method
Method S. Linear gradient of 20 to 100% B over 20 min;
  UV visualization at 220 nm;
  Column: Axia Luna 5u C18 30×100 mm;
  Flow rate: 40 mL/min;
Solvent A: 0.1% TFA, 10% ACN, 90% water;
Solvent B: 0.1% TFA, 90% ACN, 10% water.
Method T. Linear gradient of 20 to 100% B over 10 min, with 2 min hold time at 100% B;
  UV visualization at 220 nm;
  Column: YMC Sunfire, 5 μm, C18 column, 30×100 mm;
  Flow rate: 40 mL/min;
Solvent A: 0.1% TFA, 10% MeOH, 90% water;
Solvent B: 0.1% TFA, 90% MeOH, 10% water.
Method U. Linear gradient of 20 to 100% B over 10 min;
  UV visualization at 220 nm;
  Column: Axia Luna 5u C18 30×100 mm;
  Flow rate: 40 ml/min;
Solvent A: 0.1% TFA, 10% ACN, 90% water;
Solvent B: 0.1% TFA, 90% ACN, 10% water.
NMR Employed in Characterization of Examples $^1$H NMR spectra were obtained with Bruker or JEOL fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman et al., *Science*, 235:442-447 (1987); Yanagisawa et al., *Nature*, 332:411-415 (1988); Folkman et al., *J. Biol. Chem.*, 267:10931-10934 (1992); Janssens et al., *J. Biol. Chem.*, 267:14519-14522 (1992); Lamas et al., *Proc. Natl. Acad. Sci. U.S.A.*, 89:6348-6352 (1992); Luscher et al., *Hypertension*, 19:117-130 (1992); Williams et al., *Am. Rev. Respir. Dis.*, 146:S45-S50 (1992); and Bevilacqua et al., *J. Clin. Invest.*, 91:379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation,* 79:8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos et al., *Circulation,* 106:1321-1326 (2002)). Notably, the endothelial lipase-mediated binding and uptake of HDL particles and the selective uptake of HDL-derived cholesterol esters have been reported to be independent of its enzymatic lipolytic activity (Strauss et al., *Biochem. J.,* 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 uL of 1 mM DMPG in a 1:1 mixture of MeOH and $CHCl_3$ with 15 uL of 1 mM A10070 in a 1:1 mixture of MeOH and $CHCl_3$. The mixture was dried under nitrogen and resuspended in 150 uL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 uL of assay buffer (50 mM HEPES pH 8.0, 50 mM NaCl and 1 mM $CaCl_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 uL of a 1:4 dilution of vesicles. The final total reaction volume was 100 uL. The reaction rates were measured on a Gemini plate reader with an excitation wavelength of 488 nm and a emission of 530 nm. Readings were taken every 20 seconds for 10 min with agitation between each reading. The slope of the linear portion of the readout was used to calculate the rate of the reaction.

The exemplified examples disclosed in the present invention were tested in the EL assay described above and found having EL inhibitory activity. The EL IC$_{50}$ values measured for the following examples are listed in Table 1.

TABLE 1

| Ex. No. | HLE_EL_CRC IC$_{50}$ (nM) |
|---|---|
| 48 | 5.729 |
| 61 | 5.439 |
| 138 | 526.1 |
| 179 | 545.8 |
| 181 | 580.9 |
| 182 | 3645 |
| 194 | 466 |
| 232 | 5456.00 |
| 233 | 6281.00 |
| 236 | 492.70 |
| 247 | 8383.00 |
| 248 | 4662.00 |
| 272 | 3444.00 |
| 273 | 2675.00 |
| 280 | 7302.00 |
| 297 | 6519.00 |
| 299 | 2744.00 |
| 300 | 3814.00 |
| 344 | 575.40 |
| 347 | 499.80 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acytransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1.
3-(3,4-dichlorophenyl)propan-1-amine

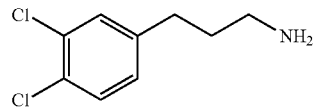 [SMILES: NCCCc1ccc(Cl)c(Cl)c1]

Intermediate 1A.
3-(3,4-dichlorophenyl)propanamide

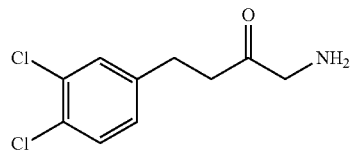 [SMILES: NCC(=O)CCc1ccc(Cl)c(Cl)c1]

To a cold (0° C.) solution of 3-(3,4-dichlorophenyl)propanoic acid (5.00 g, 22.8 mmol) in $CH_2Cl_2$ (100 mL) was added oxalyl chloride (13 mL, 25 mmol) dropwise, followed by 8 drops of DMF. The mixture was stirred at 0° C. for 20 min, then warmed to rt and stirred for an additional 2.5 h. The reaction mixture was concentrated to dryness. The residue was dissolved in $Et_2O$. The ethereal solution was slowly added to 150 mL of 28-30% solution of aqueous ammonium hydroxide cooled to 0° C. The reaction mixture was stirred at rt for 16 h. The layers were separated and the aqueous layer was extracted with ethyl acetate. The combined organic extracts were dried over sodium sulfate and concentrated in vacuo to give 4.63 g (93%) of Intermediate 1A. HPLC/MS (Method D) RT=0.82 min, $[M+H]^+$ 218.1.

Intermediate 1

To a suspension of 1.0 M lithium aluminum hydride in THF (14 mL, 14 mmol) stirring under argon in a 3-necked round bottomed flask was added a solution of Intermediate 1A (1.00 g, 4.59 mmol) dissolved in anhydrous THF (30 mL). The suspension was heated to 60° C. for 1.5 h. The reaction mixture was cooled to 0° C. and quenched by slow addition of 1N NaOH (15 mL), followed by addition of 25% aqueous solution of Na/K tartrates (15 mL). The mixture was stirred for 10 min, then ethyl acetate (100 mL) was added. After stirring an additional 1 h, the organic and aqueous phases were separated. The aqueous layer was extracted with 100 mL of EtOAc. The combined organic layers were dried over anhyd $Na_2SO_4$, filtered and evaporated in vacuo to give 869 mg (92%) of Intermediate 1. HPLC/MS (Method D) RT=0.71 min, $[M+1]^+$ 204.1; $^1$H NMR (400 MHz, chloroform-d) (δ ppm): 1.26-1.52 (m, 2H), 1.68-1.78 (m, 2H), 2.61 (t, J=7.53 Hz, 2H), 2.71 (t, J=7.03 Hz, 2H), 7.01 (dd, J=8.16, 1.88 Hz, 1H), 7.26 (d, J=1.76 Hz, 1H), 7.32 (d, J=8.28 Hz, 1H).

Intermediate 2. 4-(3,4-dichlorophenyl)butan-1-amine

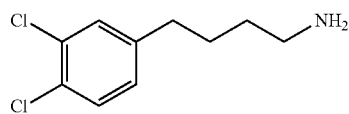 [SMILES: NCCCCc1ccc(Cl)c(Cl)c1]

Intermediate 2A. (E)-tert-butyl(4-(3,4-dichlorophenyl)but-3-enyloxy)dimethylsilane

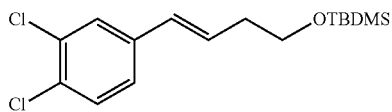 [SMILES: CC(C)(C)[Si](C)(C)OCC/C=C/c1ccc(Cl)c(Cl)c1]

4-Bromo-1,2-dichlorobenzene (0.9 mL, 7 mmol), (E)-tert-butyldimethyl(4-(4,4,5,5-tetramethyl-1,3,2-dioxaborolan-2-yl)but-3-enyloxy)silane (3.0 mL, 8.3 mmol), KF (1.2 g, 21 mmol), $Pd(OAc)_2$ (0.16 g, 0.70 mmol), and 2-(di-tert-butylphosphino)biphenyl (0.41 g, 1.4 mmol) were combined in a 20 mL microwave tube and the tube was sealed, evacuated and backfilled with argon. Degassed THF (20 mL) and $H_2O$ (0.25 mL, 14 mmol) were added under argon, and the mixture was heated to 150° C. for 60 min using microwave irradiation. The reaction mixture was cooled to rt and stirred for 3 days. The reaction mixture was diluted with ethyl acetate (200 mL). The organic layer was washed with water (200 mL) and brine (100 ml), dried over $Na_2SO_4$ and concentrated to give a black oil that was stored overnight at −20° C. The crude product was dissolved in hexanes/DCM and purified by silica gel chromatography (100% hexanes for 10 min, 0-3% ethyl acetate in hexanes over 20 min) to obtain 2.0 g (67% yield) of Intermediate 2A. HPLC/MS (Method C) RT=4.80 min, $[M-C_6H_{16}OSi]^+$ 199.1.

Intermediate 2B. (E)-4-(3,4-dichlorophenyl)but-3-en-1-ol

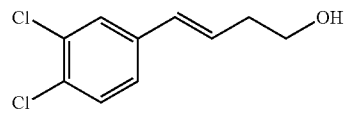 [SMILES: OCC/C=C/c1ccc(Cl)c(Cl)c1]

To solution of Intermediate 2A (2.2 g, 5.2 mmol) in THF (50 mL) cooled to 0° C. was added TBAF (6.3 mL, 6.3 mmol) via dropwise addition. The reaction mixture was stirred at 0° C. for 1 h, then diluted with ethyl acetate (200 mL). The organic layer was washed with water (2×100 mL), dried over $Na_2SO_4$ and dried in vacuo. The product was purified by silica gel chromatography (80 g silica gel; linear gradient 0-25% ethyl acetate for 30 min) to obtain 917 mg (97% yield) of Intermediate 2B. HPLC/MS (Method D) RT=1.00 min, $[M-H_2O+1]^+$ 199.1.

Intermediate 2C. (E)-4-(3,4-dichlorophenyl)but-3-enyl methanesulfonate

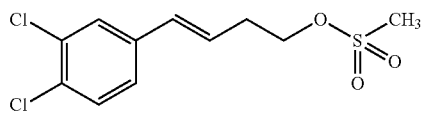 [SMILES: CS(=O)(=O)OCC/C=C/c1ccc(Cl)c(Cl)c1]

To a solution of Intermediate 2B (986 mg, 4.54 mmol) in $CH_2Cl_2$ (20 mL) was added TEA (1.899 mL, 13.63 mmol). The mixture was cooled to 0° C. and methanesulfonyl chloride (0.531 mL, 6.81 mmol) was added dropwise. The reaction was stirred for 45 min at 0° C. then warmed to rt and diluted with water (20 ml) and $CH_2Cl_2$ (20 mL). The layers were separated, and the aqueous layer extracted with $CH_2Cl_2$. The combined organic extracts were washed with saturated aqueous NaCl, dried over $Na_2SO_4$, filtered and concentrated in vacuo to give Intermediate 2C (1.30 g, 97% yield). Intermediate 2C was carried onto the next reaction without further purification. HPLC/MS (Method D) RT=1.10 min, $[M-MeSO_3H+H]^+$ 199.1.

Intermediate 2D. (E)-4-(4-azidobut-1-enyl)-1,2-dichlorobenzene

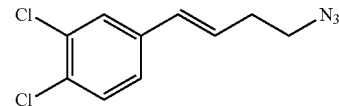 [SMILES: [N-]=[N+]=NCC/C=C/c1ccc(Cl)c(Cl)c1]

To a solution of Intermediate 2C (1.3 g, 4.4 mmol) in DMF (7 mL) was added $NaN_3$ (0.86 g, 13 mmol). The reaction mixture was stirred at rt for 16 h. The reaction mixture was diluted with EtOAc (100 mL). The organic layer was washed with 10% aqueous LiCl solution (3×200 mL), dried over $Na_2SO_4$ and dried in vacuo. The product was isolated by silica gel chromatography to obtain 570 mg (87% yield) of Intermediate 2D. HPLC/MS (Method C) RT=4.02 min, $[M+Na]^+$ 263.2.

Intermediate 2

To a solution of Intermediate 2D (570 mg, 2.3 mmol) in ethyl acetate (40 mL) was added platinum(IV) oxide (53 mg, 0.23 mmol). The contents were purged with hydrogen, then stirred under 1 atm hydrogen for 1.5 h. The reaction mixture was sparged with Ar, then filtered and dried in vacuo. 444 mg (69% yield) of Intermediate 2 was obtained as a crude product that was used without further purification. HPLC/MS (Method D) RT=0.77 min, [M+1]+218.1; $^1$H NMR (400 MHz, chloroform-d) (δ ppm): 1.44-1.51 (m, 2H), 1.57-1.75 (m, 4H), 2.57 (t, J=7.65 Hz, 2H), 2.71 (t, J=7.03 Hz, 2H), 6.99 (dd, J=8.28, 2.01 Hz, 1H), 7.24-7.26 (m, 1H), 7.32 (d, J=8.28 Hz, 1H).

Intermediate 3.
3-(3,4-dichlorophenoxy)propan-1-amine

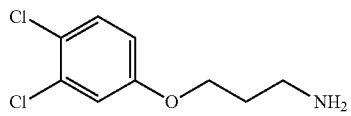

Intermediate 3A. tert-butyl 3-(3,4-dichlorophenoxy)propylcarbamate

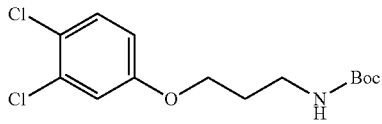 [SMILES: CC(C)(C)OC(=O)NCCCOc1ccc(Cl)c(Cl)c1]

To a solution of tert-butyl 3-bromopropylcarbamate (0.5 g, 2 mmol) and 3,4-dichlorophenol (0.38, 2.3 mmol) in DMF (10.5 mL) was added Cs$_2$CO$_3$ (1.02 g, 3.10 mmol). The reaction mixture was stirred at rt for 72 h. The reaction mixture was diluted with water and extracted with EtOAc (3×). The combined organic extracts were washed with saturated aqueous NaCl and water (1:1), dried over Na$_2$SO$_4$, filtered and evaporated to dryness. The crude product was purified by silica gel chromatography to provide Intermediate 3A (543 mg, 56% yield). HPLC/MS (Method B) RT=3.85 min, [M+H]$^+$ 320.2.

Intermediate 3

To a solution of Intermediate 3A (540 mg, 1.7 mmol) in CH$_2$Cl$_2$ (9 mL) was added TFA (1 mL). The reaction mixture was stirred at rt for 1 h, then washed with 1 N aqueous NaOH. The aqueous layers were combined and washed with CH$_2$Cl$_2$. The combined organic layers were washed with water and saturated aqueous NaCl, dried over Na$_2$SO$_4$, filtered and evaporate to dryness in vacuo. Intermediate 3 was used without further purification (255 mg, 65% yield). HPLC/MS (Method C) RT=2.30 min, [M+H]$^+$ 220.1; $^1$H NMR (500 MHz, CHCl$_3$-d$_1$) (δ ppm): 1.26 (s, 2H), 1.87-1.96 (m, 2H), 2.90 (t, J=6.60 Hz, 2H), 4.02 (t, J=6.05 Hz, 2H), 6.75 (dd, J=8.80, 2.75 Hz, 1H), 7.00 (d, J=2.75 Hz, 1H), 7.31 (d, J=8.80 Hz, 1H).

Intermediate 4.
4-(3,4-dichlorophenoxy)butan-1-amine

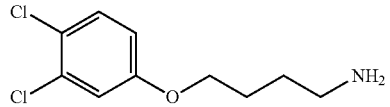 [SMILES: NCCCCOc1ccc(Cl)c(Cl)c1]

Intermediate 4A. 2-(4-(3,4-dichlorophenoxy)butyl)isoindoline-1,3-dione

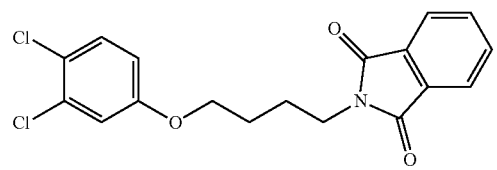 [SMILES: O=C1c2ccccc2C(=O)N1CCCCOc1ccc(Cl)c(Cl)c1]

To a solution of 2-(4-bromobutyl)isoindoline-1,3-dione (0.60 g, 2.1 mmol) and 3,4-dichlorophenol (0.38 g, 2.3 mmol) in DMF (11 mL) was added cesium carbonate (1.0 g, 3.2 mmol). The reaction was stirred at rt over for 72 h. The reaction mixture was diluted with water and extracted with EtOAc. The combined organic extracts were washed with saturated aqueous NaCl:water (1:1), dried over Na$_2$SO$_4$, filtered and evaporated to dryness. Crude material was purified by silica gel chromatography to give 541 mg of pure Intermediate 4A (69% yield). $^1$H NMR (500 MHz, CDCl$_3$-d$_1$) (δ ppm): 1.80-1.91 (m, 4H), 3.76 (t, J=6.60 Hz, 2H), 3.96 (t, J=6.05 Hz, 2H), 6.72 (dd, J=9.35, 2.75 Hz, 1H), 6.96 (d, J=2.75 Hz, 1H), 7.28 (d, J=8.80 Hz, 1H), 7.72 (dd, J=5.22, 3.02 Hz, 2H), 7.85 (dd, J=5.22, 3.02 Hz, 2H).

Intermediate 4

To a solution of Intermediate 4A (400 mg, 1.1 mmol) in EtOH (5 mL) was added hydrazine hydrate (0.32 mL, 6.6 mmol). The reaction mixture was stirred at 60° C. for 16 h. The reaction mixture was allowed to cool to rt. EtOAc was added and the mixture was stirred for 5 min. The solids were removed by filtering the mixture. The filtrate was evaporated to dryness in vacuo yielding a crude material. The semisolid was extracted with Et$_2$O. The combined Et$_2$O washings were evaporated in vacuo to give Intermediate 4 (226 mg, 84% yield). HPLC/MS (Method C) RT=2.50 min, [M+H]$^+$ 234.1; $^1$H NMR (500 MHz, DMSO-d$_6$) (δ ppm): 1.39-1.48 (m, 2H), 1.66-1.75 (m, 2H), 2.55 (t, J=6.87 Hz, 2H), 3.97 (t, J=6.32 Hz, 2H), 6.93 (dd, J=9.07, 2.47 Hz, 1H), 7.20 (d, J=2.20 Hz, 1H), 7.48 (d, J=8.80 Hz, 1H).

Intermediate 5. (Z)—N-(3-(3,4-dichlorophenyl)propyl)-2-(2,2-dimethyl-5-oxo-1,3-dioxolan-4-ylidene)acetamide

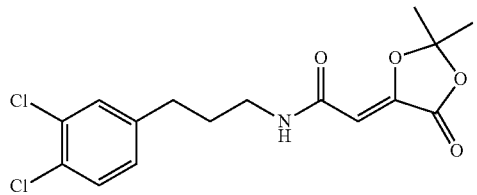 [SMILES: CC1(C)OC(=O)/C(=C/C(=O)NCCCc2ccc(Cl)c(Cl)c2)O1]

To a cold (0° C.) solution of the hydrochloride salt of Intermediate 1 (7.1 g, 30 mmol), (Z)-2-(2,2-dimethyl-5-oxo-1,3-dioxolan-4-ylidene)acetic acid (5.6 g, 33 mmol), EDC (6.8 g, 36 mmol), and HOBt (5.4 g, 36 mmol) in DMF (200 mL) was added N-methylmorpholine (13 mL, 120 mmol). The reaction mixture was allowed to warm to rt, stirred for 16 h, diluted with EtOAc (500 mL), the solution washed with saturated aqueous NaCl:water (1:1), and the organic portion dried over $MgSO_4$, filtered and evaporated to dryness in vacuo. The product was purified by silica gel chromatography (330 g silica gel) to obtain 9.68 g (89%) of Intermediate 5. HPLC/MS (Method C) RT=3.40 min; $[M+H]^+$ 359; $^1$H NMR (500 MHz, chloroform-d) (δ ppm): 1.76 (s, 6H), 1.88 (quin, J=7.42 Hz, 2H), 2.64 (t, 2H), 3.37 (q, 2H), 5.86 (s, 1H), 6.37 (br. s., 1H), 7.01-7.07 (m, 1H), 7.28 (d, 1H), 7.35 (d, J=7.70 Hz, 1H).

Intermediate 6. (E)-4-(3,4-dichlorophenyl)but-3-en-1-amine

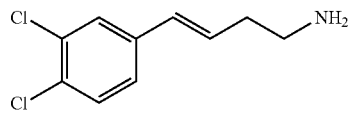 [SMILES: NCC/C=C/c1ccc(Cl)c(Cl)c1]

To a solution of Intermediate 2C (50 mg, 0.21 mmol) in THF (1 mL) were added $Ph_3P$ (60 mg, 0.23 mmol) and $H_2O$ (7.4 μl, 0.41 mmol). The reaction mixture was heated to reflux for 2 h, cooled to rt, then dried in vacuo. The crude product was dissolved in MeOH and loaded onto an Agilent ACCU-BOND® SPE SCX cartridge. The cartridge was washed with MeOH (4 column volumes). The product was eluted with 2 N $NH_3$ in MeOH (4 column volumes). Evaporation of the solvent in vacuo provided 41 mg (92% yield) of Intermediate 6. HPLC/MS (Method A; 2 min gradient) RT=0.88 min, $[M+H]^+$ 216; $^1$H NMR (400 MHz, chloroform-d) (δ ppm): 1.37 (s, 2H), 2.35 (dq, J=6.78, 1.00 Hz, 2H), 2.84 (t, J=6.65 Hz, 2H), 6.19 (td, J=15.81, 7.03 Hz, 1H), 6.35 (d, J=15.81 Hz, 1H), 7.15 (dd, J=8.28, 2.01 Hz, 1H), 7.34 (d, J=8.28 Hz, 1H), 7.42 (d, J=2.01 Hz, 1H).

Intermediate 7. N-(2-(2-(2-aminoethoxy)ethoxy)ethyl)-3-(1,3-dioxoisoindolin-2-yl)propanamide

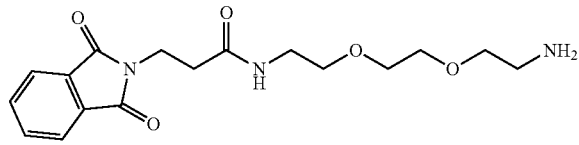 [SMILES: NCCOCCOCCNC(=O)CCN1C(=O)c2ccccc2C1=O]

Intermediate 7A. tert-butyl 2-(2-(2-(3-(1,3-dioxoisoindolin-2-yl)propanamido)ethoxy)-ethoxy)ethylcarbamate

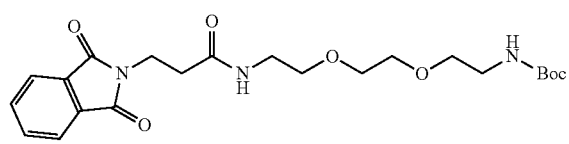 [SMILES: CC(C)(C)OC(=O)NCCOCCOCCNC(=O)CCN1C(=O)c2ccccc2C1=O]

By appropriate application of the method used to synthesize Intermediate 5, tert-butyl 2-(2-(2-aminoethoxy)ethoxy)ethylcarbamate (400 mg, 1.6 mmol) and 3-(1,3-dioxoisoindolin-2-yl)propanoic acid (388 mg, 1.8 mmol) were combined to provide Intermediate 7A (700 mg, 87% yield). HPLC/MS (Method C) RT=2.80 min, $[M+H]^+$ 450.

Intermediate 7

By the appropriate application of the method used to provide Intermediate 3, Intermediate 7A (700 mg, 1.6 mmol) was converted to Intermediate 7 (540 mg, 94% yield). HPLC/MS (Method C) RT=1.18 min, $[M+H]^+$ 350; $^1$H NMR (500 MHz, chloroform-d) (δ ppm): 1.27 (t, J=7.15 Hz, 1H), 1.41-1.46 (m, 10H), 2.05 (s, 2H), 2.63 (t, J=7.15 Hz, 2H), 2.89 (s, 1H), 2.97 (s, 2H), 3.45 (d, J=4.95 Hz, 2H), 3.54 (ddd, J=10.31, 5.09, 4.95 Hz, 5H), 3.57 (br. s., 3H), 4.02 (t, J=7.15 Hz, 2H), 4.13 (d, J=7.15 Hz, 1H), 7.71 (d, J=4.95 Hz, 2H), 7.83-7.87 (m, 2H).

Intermediate 8. 1-ethyl-4,5-dioxopyrrolidine-3-carboxylic acid

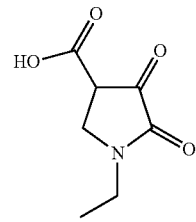

A solution of ethyl 1-ethyl-4,5-dioxopyrrolidine-3-carboxylate (150 mg, 0.753 mmol) and LiOH (43.3 mg, 1.81 mmol) in THF (0.5 mL) and $H_2O$ (0.5 mL) was heated at 80° C. for 1 h using microwave irradiation. The reaction solution was concentrated under reduced pressure and acidified with 1 N aqueous HCl, whereupon a precipitate formed. $CH_2Cl_2$ was added to the suspension and the precipitate was collected by filtration and dried in vacuo to provide Intermediate 8 (92.1 mg, 71.4% yield). HPLC/MS (Method D) RT=0.48 min, $[M+H]^+$ 172.1; $^1$H NMR (400 MHz, Solvent) (δ ppm): 1.11-1.24 (m, 3H), 3.53 (q, J=7.28 Hz, 2H), 3.84 (s, 0.47; H), 4.04 (s, 1.53; H).

Intermediate 9. 1-ethyl-4-methoxy-5-oxo-2,5-dihydro-1H-pyrrole-3-carboxylic acid

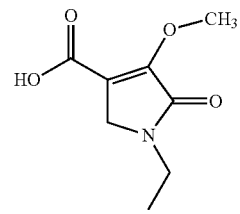

Intermediate 9A. ethyl 1-ethyl-4-methoxy-5-oxo-2,5-dihydro-1H-pyrrole-3-carboxylate

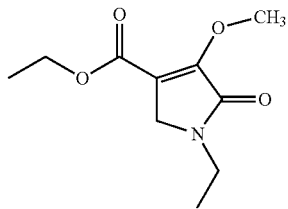

To a solution of ethyl 1-ethyl-4,5-dioxopyrrolidine-3-carboxylate (200 mg, 1.0 mmol) and DIPEA (0.18 mL, 1.0 mmol) in ACN (1.8 mL) and MeOH (0.2 mL) was added TMS-CH$_2$N$_2$ (2.0 M in Et2O; 0.5 mL, 1.0 mmol). The reaction mixture was stirred at rt for 3.5 h, then evaporated in vacuo. The product was purified by silica gel chromatography (40 g silica gel; linear gradient of 0-50% MeOH:EtOAc (10:1) in hexanes over 15 min) to obtain Intermediate 9A (203 mg, 95% yield). HPLC/MS (Method D) RT=0.73 min, [M+H]$^+$ 214.2.

Intermediate 9

A solution of Intermediate 9A (20 mg, 0.094 mmol) and NaOH (9.8 mg, 0.24 mmol) in MeOH (0.12 mL) and H$_2$O (0.12 mL) was stirred at 70° C. for 1 h. The reaction mixture was concentrated and the residue was dissolved CH$_2$Cl$_2$ and acidified using concentrated HCl. LCMS indicated aqueous layer contains small amount of product. The reaction mixture was lyophilized to give Intermediate 9 (29.1 mg, 0.094 mmol, 101% yield). HPLC/MS (Method D) RT=0.53, [M+H]$^+$ 186.1; $^1$H NMR (400 MHz, MeOH-d$_4$) (δ ppm): 4.21 (3H, s), 4.08 (2H, s), 3.51 (2H, q, J=7.28 Hz), 1.20 (3H, m).

Intermediate 10. 3-(3,4-dichlorophenylthio)propan-1-amine

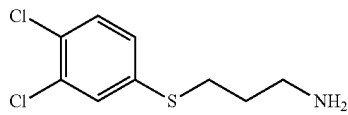 [SMILES: NCCCSc1ccc(Cl)c(Cl)c1]

Intermediate 10A. 2-(3-(3,4-dichlorophenylthio)propyl)isoindoline-1,3-dione

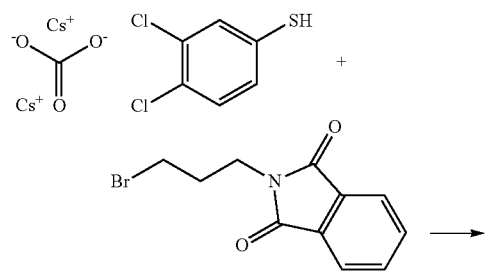

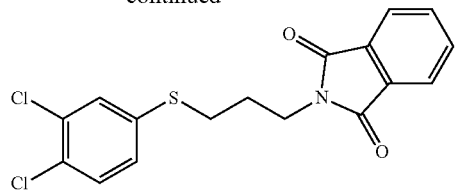

3,4-dichlorobenzenethiol (500 mg, 2.79 mmol) and 2-(3-bromopropyl)isoindoline-1,3-dione (823 mg, 3.07 mmol) were stirred in DMF (2 mL) at rt. Cs$_2$CO$_3$ (1.64 g, 5.03 mmol) was added. The reaction mixture was stirred at rt for 14 h. H$_2$O was added and the aqueous phase was extracted with EtOAc. The organic layer was dried over MgSO$_4$, filtered and concentrated to give crude product, which was triturated with ether, filtered and dried to give Intermediate 10A (760 mg, 2.08 mmol, 74.0% yield). HPLC/MS (Method N) RT=4.00 min [M+1]$^+$ 365.8.

Intermediate 10

To a solution of Intermediate 10A (100 mg, 0.270 mmol) in EtOH (1 mL) was added hydrazine (52 µL, 1.6 mmol). The reaction mixture was stirred at 60° C. for 3 h, diluted with EtOAc, filtered and the filter cake was rinsed with MeOH. The filtrate was dried over Na$_2$SO$_4$, filtered and concentrated under reduced pressure to give Intermediate 10 (63 mg, 0.27 mmol, 98% yield). HPLC/MS (Method L) RT=1.68 min [M+H]$^+$ 237. $^1$H NMR (500 MHz, CHCl$_3$-D) δ 1.64 (s, 2H) 1.71-1.73 (m, 2H) 2.79-2.81 (t, J=6.60 Hz, 2H) 2.98-3.00 (t, J=6.05 Hz, 2H) 7.42 (s, 2.75 Hz, 1H) 7.29-7.40 (d, J=2.75 Hz, 2H).

Intermediate 11. 1-(2,4-difluorophenyl)-4-ethoxy-5-oxo-2,5-dihydro-1H-pyrrole-3-carboxylic acid

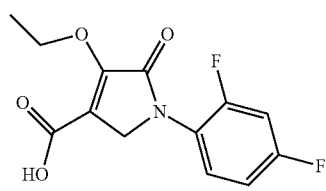 [SMILES: CCOC1=C(C(=O)O)CN(c2ccc(F)cc2F)C1=O]

Intermediate 11A. ethyl 2-(2,4-difluorophenylamino)-2-oxoacetate

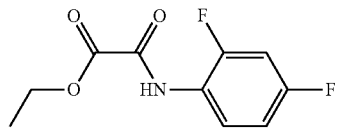

To a solution of 2,4-difluoroaniline (10 g, 77 mmol) and triethylamine (12.95 mL, 93.00 mmol) in THF (50 mL) was added ethyl 2-chloro-2-oxoacetate (9.05 mL, 81.0 mmol) drop wise at 0° C. A white solid precipitated instantly. The reaction mixture was stirred at rt for 1 h. The solvent was evaporated, and Et$_2$O was added. The solution was washed with 1N HCl (20 mL), saturated NaHCO$_3$ and then brine, then the organic layer dried over MgSO$_4$, filtered and concentrated to give Intermediate 11A (15.8 g, 68.9 mmol, 89.0% yield) as a white crystalline solid. HPLC/MS (Method L) RT=1.58 min, [M+H]$^+$ 230.0.

Intermediate 11B. dimethyl 1-(2,4-difluorophenyl)-4-ethoxy-5-oxo-2,5-dihydro-1H-pyrrole-2,3-dicarboxylate

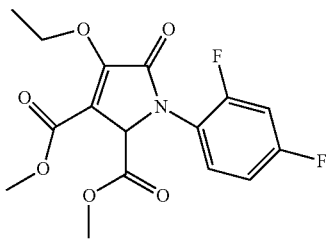 [SMILES: CCOC1=C(C(=O)OC)C(C(=O)OC)N(c2ccc(F)cc2F)C1=O]

To a stirred solution of triphenylphosphine (629 mg, 2.40 mmol) and Intermediate 11A (458 mg, 2.00 mmol) in ClCH$_2$CH$_2$Cl (1 mL) was added dimethyl but-2-ynedioate (0.26 mL, 2.1 mmol) drop wise at rt. The reaction mixture was stirred at 80° C. in a capped vial for 18 h. The reaction mixture was allowed to cool to rt, loaded on to a 40 g silica gel column and purified with 0-100% EtOAc/Hex to give Intermediate 11B (560 mg, 1.58 mmol, 79.0% yield) as a slightly tan viscous oil. HPLC/MS (Method L) RT=1.77 min, [M+H]+ 356.0.

Intermediate 11

To a mixture of Intermediate 11B (1.6 g, 4.5 mmol) in MeOH (3 mL) and THF (9 mL) was added 1N LiOH (13.51 mL, 13.51 mmol). The reaction mixture was stirred at reflux for 0.5 h then concentrated. To the residue was added 1N HCl to acidify pH to 2. The aqueous layer was extracted with DCM three times. The combined organic layers were dried over Na$_2$SO$_4$, filtered and concentrated to give Intermediate 11 as a light yellow solid (1.28 g, 4.52 mmol, 100% yield). HPLC/MS (Method L) RT=1.62 min, [M+H]+ 284.0.

Intermediate 12. dimethyl 4-ethoxy-1-(4-fluorophenyl)-5-oxo-2,5-dihydro-1H-pyrrole-2,3-dicarboxylate

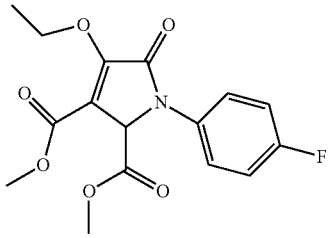 [SMILES: CCOC1=C(C(=O)OC)C(C(=O)OC)N(c2ccc(F)cc2)C1=O]

To a stirred solution of triphenylphosphine (262 mg, 1.00 mmol) and 4-fluoroaniline (111 mg, 1.00 mmol) in CH$_2$Cl$_2$ (5 mL) was added dimethyl but-2-ynedioate (142 mg, 1.00 mmol) dropwise. The reaction mixture turned brown and was stirred for 1 h before triethylamine (139 μL, 1.00 mmol) and ethyl 2-chloro-2-oxoacetate (150 mg, 1.10 mmol) were added. The reaction mixture was stirred at rt for 14 h, concentrated and the residue was purified by ISCO, eluting with Hex/EtOAc (0-20% B over 15 min) to Intermediate 12 (180 mg, 0.530 mmol, 53.0% yield) as a white solid. HPLC/MS (Method L) RT=1.75 min, [M+H]$^+$ 337.9.

Intermediate 13. 4-ethoxy-2-(methoxycarbonyl)-5-oxo-1-phenyl-2,5-dihydro-1H-pyrrole-3-carboxylic acid

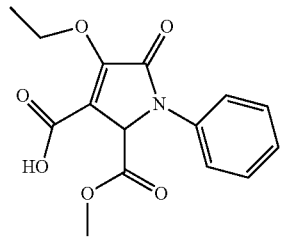 [SMILES: CCOC1=C(C(=O)O)C(C(=O)OC)N(c2ccccc2)C1=O]

To a mixture of dimethyl 4-ethoxy-5-oxo-1-phenyl-2,5-dihydro-1H-pyrrole-2,3-dicarboxylate (240 mg, 0.750 mmol), which was synthesized according to similar methods as described for Intermediate 11, in MeOH (1 mL) was added 1N NaOH (1.50 mL, 1.50 mmol). The reaction mixture was heated at 80° C. for 2 h, allowed to cool to rt, and then concentrated. To the residue was added 1N HCl to acidify pH to 2. The solvent was removed under reduced pressure to afford crude Intermediate 13 as a gray solid which was used without further purification. HPLC/MS (Method L) RT=1.59 min, [M+H]$^+$ 306.0.

Intermediate 14. (R)—N-(1-(3-bromophenyl)ethyl)-1-(2,4-difluorophenyl)-4-ethoxy-5-oxo-2,5-dihydro-1H-pyrrole-3-carboxamide

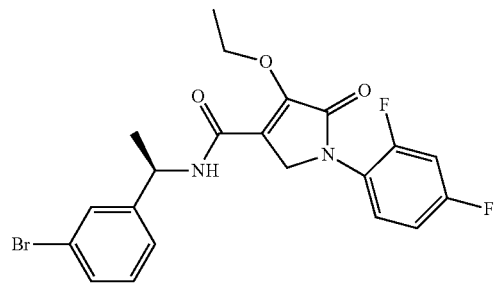 [SMILES: CCOC1=C(C(=O)N[C@H](C)c2cccc(Br)c2)CN(c2ccc(F)cc2F)C1=O]

Intermediate 14A. 1-(2,4-difluorophenyl)-4-ethoxy-5-oxo-2,5-dihydro-1H-pyrrole-3-carbonyl chloride

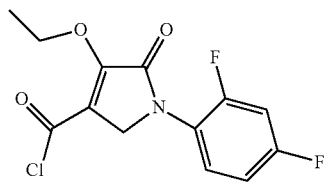 [SMILES: CCOC1=C(C(=O)Cl)CN(c2ccc(F)cc2F)C1=O]

To a solution of Intermediate 11 (0.14 g, 0.50 mmol) in DCM (2 mL) was added oxalyl chloride (0.38 mL, 0.75 mmol) and one drop of DMF. The reaction mixture was stirred at rt for 1.5 h and the resulting Intermediate 14A was used directly for next step. HPLC/MS (Method L) RT=1.79 min, [M+H]$^+$ 298.0.

Intermediate 14

To a solution of Intermediate 14A (648 mg, 2.15 mmol) in DCM (2 mL) was added TEA (0.90 mL, 6.4 mmol) and (R)-1-(3-bromophenyl)ethanamine (430 mg, 2.15 mmol). The reaction mixture was stirred at rt for 18 h and diluted with DCM. The organic layer was separated and washed with 1N HCl and brine, dried over Na$_2$SO$_4$, filtered and concentrated. The residue was purified by ISCO (0-40% EtOAc/Hexanes) to give Intermediate 14 (605 mg, 1.30 mmol, 61.0% yield) as a yellow oil. HPLC/MS (Method L) RT=2.25 min, [M+H]$^+$ 465.0.

Intermediate 15.
4-(3,4-dichlorophenyl)butan-2-amine (racemic)

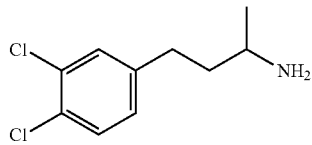

Intermediate 15A 3-(3,4-dichlorophenyl)-N-methoxy-N-methylpropanamide

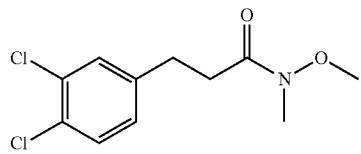 [SMILES: CON(C)C(=O)CCc1ccc(Cl)c(Cl)c1]

To a solution of 3-(3,4-dichlorophenyl)propanoic acid (0.50 g, 2.3 mmol) and N,O-dimethylhydroxylamine hydrochloride (0.27 g, 2.7 mmol) in DCM (5 mL) was added EDCI (0.57 g, 3.0 mmol), HOBt (0.35 g, 2.3 mmol) and TEA (0.39 mL, 2.8 mmol). The reaction mixture was stirred at rt for 18 h, concentrated and the residue was purified by ISCO chromatography (EtOAc/Hexanes 0-100% over 20 min, column 40 g, flow rate 40 mL/min) to give Intermediate 15A (569 mg, 2.17 mmol, 95.0% yield) as a clear oil. HPLC/MS (Method R) RT=1.76 min, [M+1]$^+$ 262.1.

Intermediate 15B.
4-(3,4-dichlorophenyl)butan-2-one

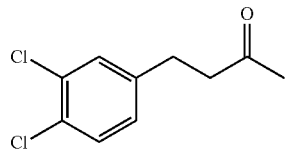

At 0° C. to a solution of 3-(3,4-dichlorophenyl)-N-methoxy-N-methylpropanamide (569 mg, 2.17 mmol) in ether (10 mL) was added drop wise methyl magnesium bromide (2.17 mL, 6.51 mmol) and the solution was stirred at 0° C. for 1 h. The reaction mixture was allowed to warm up to rt and stirred for 18 h. The reaction mixture was cooled to 0° C. and brine was added to quench the reaction. The aqueous layer was extracted with DCM three times. The combined organic layers were dried over MgSO$_4$, filtered and concentrated. The residue was purified by ISCO chromatography (EtOAc/Hexanes 0-50% over 20 min, column 40 g, flow rate 40 mL/min) to give Intermediate 15B (292 mg, 1.34 mmol, 62.0% yield) as a yellow oil. $^1$H NMR (400 MHz, CHLOROFORM-d) δ ppm 2.15 (3H, s), 2.75 (2H, t, J=6.9 Hz), 2.80-2.90 (2H, m), 7.02 (1H, dd, J=8.2, 2.2 Hz), 7.28 (1H, d, J=2.2 Hz), 7.33 (1H, d, J=8.2 Hz).

Intermediate 15 (Racemic)

Ammonium acetate (178 mg, 2.30 mmol) was added to a solution of Intermediate 15B (50 mg, 0.23 mmol) in methanol (1 mL) and the reaction mixture was stirred at rt for 10 min, then sodium cyanoborohydride (87.0 mg, 1.38 mmol) was added and the reaction mixture was stirred at rt for 18 h. The reaction mixture was diluted with DCM, washed with saturated NaHCO$_3$, dried over MgSO$_4$, filtered and concentrated to give Intermediate 15 (49.9 mg, 100% crude). HPLC/MS (Method D) RT=0.75 min, [M+1]$^+$ 218.1.

Intermediate 16.
4-(3,4-dichlorophenyl)butan-2-amine hydrochloride
(Enantiomer A)

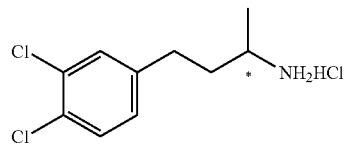

Intermediate 16A. 3-(3,4-dichlorophenyl)propanal

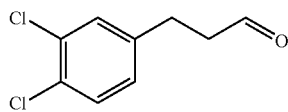 [SMILES: O=CCCc1ccc(Cl)c(Cl)c1]

Palladium(II) acetate (0.17 g, 0.73 mmol) was added to a mixture of 1,2-dichloro-4-iodobenzene (2.00 g, 7.33 mmol), prop-2-en-1-ol (0.75 mL, 11 mmol), benzyltriethylammonium chloride (1.67 g, 7.33 mmol) and sodium bicarbonate (1.54 g, 18.3 mmol) in DMF (5 mL) and the mixture was degassed and back filled with Ar three times. The reaction mixture was heated at 60° C. for 2 h. The mixture was diluted with Et$_2$O (15 mL) and H$_2$O (15 mL) and the mixture was filtered through a celite pad. The organic layer was separated and the aqueous layer was extracted with E$_2$O twice. The combined organic layers were dried over MgSO$_4$, filtered and concentrated. The residue was purified by ISCO chromatography (EtOAc/Hexanes 0-10% over 20 min, column 80 g, flow rate 40 mL/min) to give Intermediate 16A (1.0 g, 4.9 mmol, 67% yield) as a yellow oil. $^1$H NMR (400 MHz, CHLOROFORM-d) δ ppm 2.78 (2H, t, J=7.3 Hz), 2.91 (2H, t, J=7.3 Hz), 7.03 (1H, dd, J=8.2, 2.1 Hz), 7.29 (1H, d, J=2.3 Hz), 7.35 (1H, d, J=8.0 Hz), 9.81 (1H, s).

Intermediate 16B. (S,E)-N-(3-(3,4-dichlorophenyl)propylidene)-2-methylpropane-2-sulfinamide

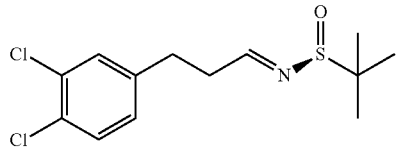 [SMILES: CC(C)(C)[S@](=O)/N=C/CCc1ccc(Cl)c(Cl)c1]

To a solution of Intermediate 16A (1.0 g, 4.9 mmol) in CH$_2$Cl$_2$ (5 mL) was added (S)-2-methylpropane-2-sulfinamide (0.72 g, 5.9 mmol) followed by the addition of pyridine 4-methylbenzenesulfonate (0.062 g, 0.25 mmol) and MgSO$_4$ (2.96 g, 24.6 mmol). The reaction mixture was stirred at rt for 18 h, and then filtered through a celite pad. The filtrate was concentrated under reduced pressure and the residue was purified by ISCO chromatography (EtOAc/Hexanes 0-30% over 15 min, column 80 g, flow rate 85 mL/min) to give Intermediate 16B (1.20 g, 3.93 mmol, 80.0% yield) as a white solid. HPLC/MS (Method D) RT=1.13 min, [M+1]$^+$ 306.0.

Intermediate 16C. (S)—N-(4-(3,4-dichlorophenyl)butan-2-yl)-2-methylpropane-2-sulfinamide

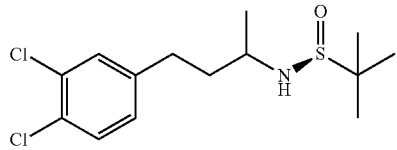 [SMILES: CC(CCc1ccc(Cl)c(Cl)c1)N[S@@](=O)C(C)(C)C]

To a solution of Intermediate 16B (4.00 g, 13.1 mmol) in DCM (50 mL) was added slowly a solution of methylmagnesium bromide in toluene and THF (13.99 mL, 1.400 M, 19.59 mmol) and the reaction mixture was heated to reflux for 2.5 h. The reaction mixture was allowed to cool to rt and, diluted with DCM, washed with saturated NH$_4$Cl, and the organic portion dried over MgSO$_4$, filtered and concentrated. The residue was purified by ISCO chromatography (EtOAc/Hexanes 0-50% over 30 min, column 330 g, flow rate 100 mL/min) to give Intermediate 16C (2.80 g, 8.69 mmol, 67.0% yield) as a white solid. HPLC/MS (Method D) RT=1.12 min, [M+1]$^+$ 322.1; Chiral HPLC (Method L) RT=4.55 min, PA=100%.

Intermediate 16

To a solution of Intermediate 16C (2.67 g, 8.27 mmol) in Et$_2$O (12 mL) was added a solution of HCl in Et$_2$O (12.41 mL, 2.000M, 24.82 mmol) and the reaction mixture was stirred at rt for 1 h. The white precipitate was filtered and rinsed with Et$_2$O to give Intermediate 16 (1.81 g, 100% crude) as a white solid. HPLC/MS (Method D) RT=0.74 min, [M+1]$^+$ 219.9.

Intermediate 17. 4-(3,4-dichlorophenyl)butanoic acid

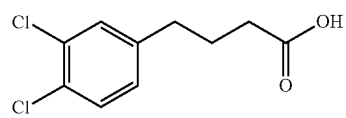 [SMILES: O=C(O)CCCc1ccc(Cl)c(Cl)c1]

Intermediate 17A. 3-(3,4-dichlorophenyl)propan-1-ol

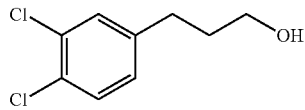 [SMILES: OCCCc1ccc(Cl)c(Cl)c1]

At rt to a suspension of 3-(3,4-dichlorophenyl)propanoic acid (2.0 g, 9.1 mmol) in THF (40 mL) was added borane-THF (18.3 mL, 1.00M in THF, 18.3 mmol). After 12 h, the reaction mixture was cooled to 0° C. and quenched by the cautious addition of 1M NaOH. The reaction mixture was diluted with ether, washed with water twice, then brine, and the organic portion dried over MgSO$_4$, filtered, and concentrated. Trituration with 10% Ethyl acetate/Hexane (300 mL) gave a white powder which was collected by filtration to give Intermediate 17A (2.00 g, 9.80 mmol, 100% crude). $^1$H NMR (400 MHz, CHLOROFORM-d) δ ppm 1.73-1.81 (2H, m), 2.56-2.65 (2H, m), 3.59 (2H, t, J=6.4 Hz), 6.96 (1H, dd, J=8.0, 2.0 Hz), 7.22 (1H, d, J=2.0 Hz), 7.27 (1H, d, J=8.3 Hz).

Intermediate 17B. 4-(3,4-Dichlorophenyl)butanenitrile

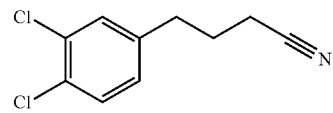 [SMILES: N#CCCCc1ccc(Cl)c(Cl)c1]

Intermediate 17A (2.0 g, 9.8 mmol) was dissolved in pyridine (20 mL) and treated with methane sulfonyl chloride (0.84 mL, 10 mmol) drop wise while maintaining the temperature below 20° C. The reaction mixture was stirred at rt for 3 h and added to concentrated HCl (10 mL) in crushed ice. The layers were separated and the aqueous layer was extracted with ethyl acetate twice. The combined organic layers were washed with saturated NaHCO$_3$ twice and brine and the organic portion dried over Na$_2$SO$_4$, filtered and concentrated. The resulting light yellow sulfonate ester was immediately dissolved in DMF (20 mL) and water (4 mL) and cooled to 0° C. Solid potassium cyanide (0.95 g, 15 mmol) was added to the reaction mixture and the mixture was stirred at rt for 72 h. The reaction mixture was then diluted with water and the aqueous phase extracted with ethyl acetate twice. The combined organic layers were washed with H$_2$O twice, brine twice, dried over Na$_2$SO$_4$, filtered and concentrated. The residue was purified by ISCO chromatography (EtOAc/Hexanes 0-80%, column 80 g) to give Intermediate 17B (1.06 g, 24.8 mmol, 51.0%) as a white solid. HPLC/MS (Method L) RT=1.952 min, [M+1]$^+$=214.0.

Intermediate 17

Intermediate 17B (900 mg, 4.20 mmol) was dissolved in ethanol (10 mL) and treated with aqueous sodium hydroxide (50% in water, 10 mL). The reaction mixture was heated at reflux for 3 h. After allowing to cool to rt, the mixture was concentrated in vacuo and the crude product dissolved in ethyl acetate and washed with water twice. The combined aqueous layers were acidified to pH ~2.0 with concentrated hydrochloric acid. The product precipitated out as a white solid, which was extracted with ethyl acetate twice. The combined organic layers were washed with brine twice, dried over $Na_2SO_4$, filtered and concentrated to afford Intermediate 17 (1.00 g, 4.20 mmol, 100%) as a white solid. HPLC/MS (Method L) RT=1.97 min, $[M+1]^+$=233.1.

Intermediate 18.
5-(3,4-dichlorophenyl)pentan-2-amine hydrobromide (Enantiomer A)

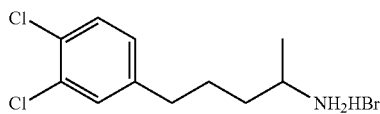

Intermediate 18A.
5-(3,4-dichlorophenyl)pentan-2-amine

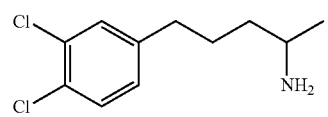

By appropriate application of methods described for Intermediate 15, Intermediate 17 (1.0 g, 4.3 mmol) was converted to Intermediate 18A (0.62 g, 62% for three steps). HPLC/MS (Method L): RT=1.66 min, $[M+1]^+$=232.0.

Intermediate 18B. benzyl 5-(3,4-dichlorophenyl)pentan-2-ylcarbamate (Enantiomer A)

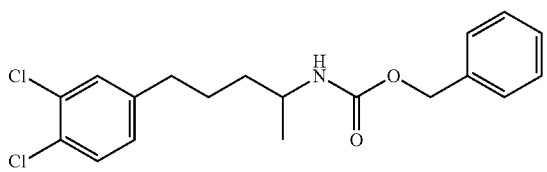 [SMILES: CC(CCCc1ccc(Cl)c(Cl)c1)NC(=O)OCc1ccccc1]

Intermediate 18A (0.500 g, 2.15 mmol) and sodium carbonate (0.50 g, 4.7 mmol) were combined in THF (10 mL) and treated with benzyl chloroformate (0.31 mL, 2.2 mmol) drop wise over 15 min. The reaction mixture was stirred at rt for 18 h. The mixture was concentrated in vacuo, diluted with DCM and washed with saturated $Na_2CO_3$ twice, brine and the organic portion dried over $Na_2SO_4$, filtered and concentrated. The residue was purified by ISCO chromatography (EtOAc/Hexanes 0-50%, column 40 g) to give benzyl 5-(3,4-dichlorophenyl)pentan-2-ylcarbamate (440 mg, 1.20 mmol, 56.0%) as a clear oil. HPLC/MS (HPLC Method L): RT=2.32 min, $[M+1]^+$=366.0. The racemates were separated on chiral prep HPLC (chiral AD 10 micron 4.6×250 mm, 15 min 5% isocratic. A=EtOH/MeOH (50/50). B=Heptane; RT=9.8 min) to afford Intermediate 18B (220 mg, 0.600 mmol, 28.0%). $^1$H NMR (400 MHz, CHLOROFORM-d) δ ppm 1.07 (3H, d), 1.32-1.41 (2H, m), 1.51-1.62 (2H, m), 2.42-2.57 (2H, m), 3.62-3.75 (1H, m), 4.42 (1H, br. s.), 5.02 (2H, s), 6.91 (1H, d, J=7.5 Hz), 7.17 (1H, br. s.), 7.23-7.31 (6H, m).

Intermediate 18

Intermediate 18B (220 mg, 0.600 mmol) was added hydrobromic acid (0.50 ml, 33% in acetic acid, 3.0 mmol) and the reaction mixture was stirred at rt for 1.5 h. The reaction mixture was triturated with ether (20 mL) to afford Intermediate 18 (120 mg, 0.380 mol, 64.0%). HPLC/MS (Method L): RT=1.68 min, $[M+1]^+$=232.1.

Intermediate 19.
5-(3,4-dichlorophenyl)pentan-2-amine hydrobromide (Enantiomer B)

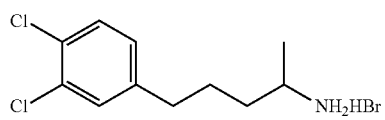

Intermediate 19A. benzyl 5-(3,4-dichlorophenyl)pentan-2-ylcarbamate (Enantiomer B)

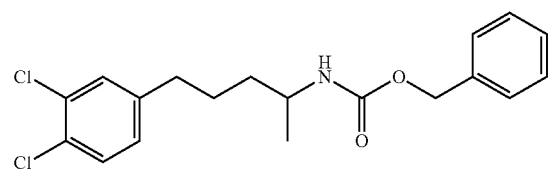 [SMILES: CC(CCCc1ccc(Cl)c(Cl)c1)NC(=O)OCc1ccccc1]

By appropriate application of method described for Intermediate 18B, Intermediate 18A (0.50 g, 2.2 mmol) was converted to Intermediate 19A (225 mg, 0.610 mmol, 28.0%). Chiral separation RT=12.89 min.

Intermediate 19

By appropriate application of procedures described in Intermediate 18, Intermediate 19A (225 mg, 0.610 mmol) was converted to Intermediate 19 (150 mg, 78.0%) as a white powder. HPLC/MS (Method L): RT=1.67 min, $[M+1]^+$=232.1.

Intermediate 20.
2-amino-5-(3,4-dichlorophenyl)pentanenitrile

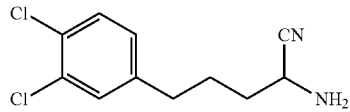 [SMILES: N#CC(N)CCCc1ccc(Cl)c(Cl)c1]

Intermediate 20A. 4-(3,4-dichlorophenyl)butan-1-ol

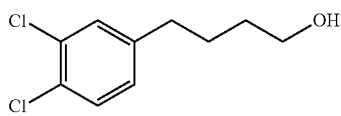 [SMILES: OCCCCc1ccc(Cl)c(Cl)c1]

At 0° C. to a solution of 4-(3,4-dichlorophenyl)butanoic acid (3.7 g, 16 mmol) in dry THF (50 mL) was added borane THF complex (31.7 mL, 1.00 M in THF, 31.7 mmol) cautiously over 15 min and the reaction mixture allowed to warm to rt overnight. The reaction mixture was cooled to 0° C. and quenched by the cautious addition of 1 M NaOH. The reaction mixture was diluted with ether, washed with water twice, then brine, dried over MgSO$_4$, filtered and concentrated. The residue was triturated with 10% ethyl acetate/hexanes (300 mL) to give Intermediate 20A (3.50 g, 100%) as white powder. $^1$H NMR (400 MHz, CHLOROFORM-d) δ ppm 1.47-1.66 (4H, m), 2.53 (2H, t, J=7.5 Hz), 3.55-3.61 (2H, m), 6.94 (1H, dd, J=8.2, 2.1 Hz), 7.17-7.21 (1H, m), 7.26 (1H, d, J=8.3 Hz).

Intermediate 20B. 4-(3,4-Dichlorophenyl)butanal

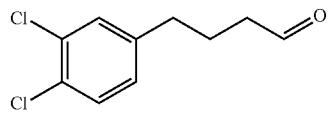 [SMILES: O=CCCCc1ccc(Cl)c(Cl)c1]

To a solution of Intermediate 20A (3.5 g, 16 mmol) in DCM (100 mL) was added silica gel (2.5 g) followed by pyridinium chlorochromate (4.13 g, 19.2 mmol). After stirring for 1 h, the reaction mixture was filtered and the filtrate was diluted with water and the layers were separated. The aqueous layer was further extracted with dichloromethane twice. The combined organic layers were washed with 1N HCl twice, water twice, brine twice, dried over MgSO$_4$, filtered and concentrated. The residue was purified by ISCO chromatography (EtOAc/Hexanes 0-70%, column 40 g) to give Intermediate 20B (2.3 g, 66%) as an oil. $^1$H NMR (400 MHz, CHLOROFORM-d) δ ppm 1.80-1.92 (2H, m), 2.36-2.43 (2H, m), 2.50-2.60 (2H, m), 6.94 (1H, dd, J=8.3, 2.0 Hz), 7.25-7.32 (1H, m), 7.28 (1H, d, J=8.3 Hz), 9.70 (1H, s).

Intermediate 20

Trimethylsilyl cyanide (0.42 mL, 3.1 mmol) and zinc iodide (33 mg, 0.10 mmol) were combined in a pressure tube and treated with a solution of Intermediate 20B (0.45 g, 2.1 mmol) in anhydrous THF (6 mL). After stirring for 15 min at rt, a solution of ammonia (10.4 mL, 7.00 N in methanol, 72.5 mmol) was introduced. The tube was sealed and the reaction mixture was stirred at 60° C. for 3 h. The solvent was removed in vacuo to afford Intermediate 20 (501 mg, 100% crude) as a dark brown oil. HPLC/MS (Method L) RT=1.59 min, [M+1]$^+$ 243.1.

Intermediate 21. 4-methoxy-1-methyl-5-oxo-N-(prop-2-ynyl)-2,5-dihydro-1H-pyrrole-3-carboxamide

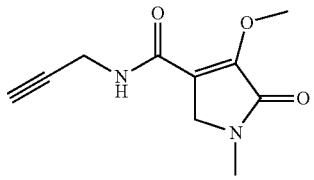

To a solution of prop-2-yn-1-amine (0.43 mL, 7.7 mmol), 4-methoxy-1-methyl-5-oxo-2,5-dihydro-1H-pyrrole-3-carboxylic acid (1.2 g, 7.0 mmol) and PyBOP® (4.01 g, 7.71 mmol) in DMF (25 mL) was added diisopropylethylene amine (3.67 mL, 21.0 mmol) and the reaction mixture was stirred at rt for 2 h. The reaction mixture was concentrated and purified by ISCO chromatography (ethyl acetate/hexane 1-100%, column 40 g cartridge) to afford Intermediate 21 (1.2 g, 82%) as a white paste. HPLC/MS (Method L) RT=0.99 min, [M+1]$^+$ 209.2.

Intermediate 22. 2-methoxy-3-oxo-3,5,6,7,8,8a-hexahydroindolizine-1-carboxylic acid

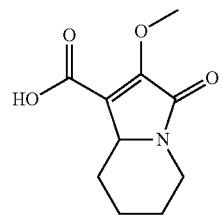

Intermediate 22A. ethyl 2-(piperidin-2-yl)acetate

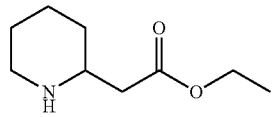

At rt a mixture of ethyl 2-(pyridin-2-yl)acetate (3.0 g, 18 mmol) and platinum (IV) oxide (0.825 g, 3.63 mmol) in methanol (25 mL) was subject to hydrogenation at 50 psi for 18 h. After filtration, the filtrate was concentrated to afford Intermediate 22A (3.0 g, 96%) as a clear oil. HPLC/MS (Method L) RT=0.99 min, [M+1]$^+$ 172.2.

Intermediate 22B. ethyl 2-(2-(2-ethoxy-2-oxoethyl)piperidin-1-yl)-2-oxoacetate

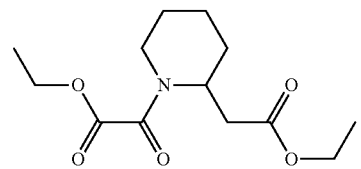 [SMILES: CCOC(=O)CC1CCCCN1C(=O)C(=O)OCC]

At 0° C. to a solution of Intermediate 22A (3.00 g, 17.5 mmol) and TEA (4.9 mL, 35 mmol) in DCM (100 mL) was added mono-ethyl oxalyl chloride (1.96 mL, 17.5 mmol) and the reaction mixture was stirred at rt for 2 h. The reaction mixture was quenched by a few drops of MeOH and concentrated. The residue was purified by ISCO chromatography (ethyl acetate/hexanes 0-100%, column 80 g) to give Intermediate 22B (3.8 g, 95%) as a clear oil. HPLC/MS (Method L) RT=1.45 min, [M+1]$^+$ 272.1.

Intermediate 22C. ethyl 2-hydroxy-3-oxo-3,5,6,7,8,
8a-hexahydroindolizine-1-carboxylate

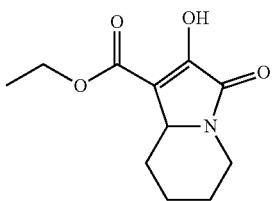 [SMILES: CCOC(=O)C1=C(O)C(=O)N2CCCCC12]

Intermediate 22B (3.75 g, 13.8 mmol) was suspended in toluene (100 mL) and treated with potassium ethoxide (5.42 mL, 24% in methanol, 13.8 mmol). The clear mixture was heated at 100° C. for 4 h. After cooling to rt, the solvent was evaporated and the residue was dissolved in ethyl acetate. The organic layer was washed with 10% citric acid twice, brine twice, dried over Na$_2$SO$_4$, filtered and concentrated to afford Intermediate 22C (2.0 g, 64%) as a clear oil. $^1$H NMR (400 MHz, CHLOROFORM-d) δ ppm 1.28 (3H, td, J=7.2, 1.8 Hz), 1.46-1.87 (5H, m), 2.19 (1H, br. s.), 3.12-3.51 (1H, m), 4.09-4.23 (2H, m), 4.27-4.42 (2H, m).

Intermediate 22D. ethyl 2-methoxy-3-oxo-3,5,6,7,8,
8a-hexahydroindolizine-1-carboxylate

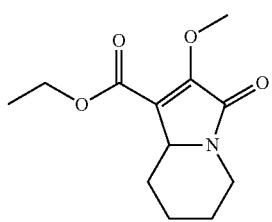 [SMILES: CCOC(=O)C1=C(OC)C(=O)N2CCCCC12]

At 0° C. to a solution of Intermediate 22C (30 mg, 0.13 mmol) and N,N-diisopropylethylamine (35 μL, 0.20 mmol) in methanol (0.15 mL) and acetonitrile (1.35 mL) was added (trimethylsilyl)diazomethane (0.10 mL, 2.0 M in diethyl ether, 0.20 mmol). The reaction mixture was stirred at rt for 2 h, concentrated and the residue was purified by ISCO chromatography (ethyl acetate/hexane 0-100%, column, 4 g) to afford Intermediate 22D (20 mg, 63%). $^1$H NMR (400 MHz, CHLOROFORM-d) δ ppm 1.25-1.41 (5H, m), 1.50-1.61 (1H, m), 1.76-1.98 (2H, m), 2.44-2.52 (1H, m), 2.79-2.90 (1H, m), 3.95 (1H, dd, J=11.4, 3.6 Hz), 4.23-4.38 (6H, m).

Intermediate 22

The mixture of Intermediate 22D (50 mg, 0.21 mmol) and a solution of lithium hydroxide (0.25 mL, 0.25 mmol) in methanol (0.5 mL) and water (0.5 mL) was stirred for 30 min, then neutralized with a 1 N hydrochloric acid (0.25 mL, 0.25 mmol). The solvent was removed in vacuo to afford Intermediate 22 (44.0 mg, 100% crude) as a black solid. HPLC/MS (Method L) RT=1.13 min, [M+1]$^+$ 212.2.

Examples

Examples 6, 7 and 9 were synthesized via parallel synthesis according to the following method.

To a solution of (Z)-2-(2,2-dimethyl-5-oxo-1,3-dioxolan-4-ylidene)acetic acid (0.27 g, 1.6 mmol) in CH$_2$Cl$_2$ (3.9 mL) was added oxalyl chloride (0.13 mL, 1.6 mmol). A few drops of DMF were added, and the reaction mixture was stirred at rt for 2 h to produce a 0.4 M stock solution of (Z)-2-(2,2-dimethyl-5-oxo-1,3-dioxolan-4-ylidene)acetyl chloride (Solution A). An aliquot of Solution A (0.25 mL, 0.1 mmol) was added to each 16×100 mm Wheaton tubes that had been charged separately with CH$_2$Cl$_2$ (0.25 mL), DIEA (0.050 mL, 0.3 mmol) and an amine (0.1 mmol) corresponding to the R$^5$-amide contained in the final example. The vials were capped and the reaction mixtures were agitated at 400 rpm at rt for 16 h using an INNOVA® platform shaker. After removal from the shaker, each reaction mixture was diluted with MeOH (0.25 mL), treated with polystyrene-isocyanate resin (0.091 g, 1.1 mmol/g, 0.1 mmol) and agitated at 400 rpm for 2 h. Following filtration to remove the polystyrene beads, the filtrates were collected and dried under a stream of N$_2$ for 1 h using a ZYMARK® tabletop dryer set to 45° C. The amides thus formed were carried onto the next step without further purification. To a separate reaction vessel was added paraformaldehyde (87 mg, 2.88 mmol), MeOH (10.6 mL) and CH$_3$NH$_2$ (2.0 M in THF; 1.44 mL, 2.88 mmol). This mixture was heated to 60° C. for 5 min using microwave irradiation to provide Solution B. To each vial containing an amide was added a 0.5 mL aliquot of Solution B. The reaction mixtures were agitated at 400 rpm at 80° C. for 16 h on an INNOVA® platform shaker. The reaction mixtures were removed from the shaker, cooled to rt and diluted with MeOH (0.25 mL). Examples 1-12 were purified from their corresponding solutions by RP preparative HPLC using Method H. HPLC/MS data for each compound was collected using Method E, and the molecular masses were determined by MS (ES) by the formula m/z. Both the retention time and MS data for Examples 6, 7 and 9 are listed in Table 2. Note: 2.0 M CH$_3$NH$_2$ in MeOH may be substituted for 2.0 M CH$_3$NH$_2$ in THF.

Examples 22 and 33 were synthesized via parallel synthesis according to the following method. To each microwave vial containing an aldehyde (0.08 mmol) corresponding to the R$^3$ group contained in Examples 13-36 was added MeOH (0.65 mL) and CH$_3$NH$_2$ (2.0 M in THF; 0.04 mL, 0.08 mmol). The reaction mixtures were heated to 60° C. for 10 min using microwave irradiation, then cooled to rt. To each reaction mixture was added a 0.24 M solution of Intermediate 5 in MeOH (0.22 mL, 0.05 mmol). The resulting reaction mixtures were heated to 100° C. for 20 min using microwave irradiation. After cooling to rt, they were diluted with MeOH (0.25 mL). Examples 22 and 33 were purified from their corresponding solutions by RP preparative HPLC using Method H. HPLC/MS data for each compound was collected using Method E, and the molecular masses of the compounds were determined by MS (ES) by the formula m/z. Both the retention time and MS data are listed in Table 2.

Examples 48, 61, 62, 63, 74, 75, 81, 83, 84, 85, 87, 88, 96, 98, 100, 101, 103, 104, 105, 106, 107, 108, 111, 115, 118, 119, 123, 129, 136, 138, 139 and 140 were synthesized via parallel synthesis according to the following method. To each microwave vial containing an amine (0.09 mmol) corresponding to the $R^1$ group contained in these examples was added a suspension of paraformaldehyde (0.12 M in MeOH, 0.750 mL, 0.09 mmol). The reaction mixtures were heated to 60° C. for 10 min using microwave irradiation, then cooled to rt. To each reaction mixture was added a 0.24 M solution of Intermediate 5 in MeOH (0.25 mL, 0.06 mmol). The resulting reaction mixtures were heated to 100° C. for 10 min using microwave irradiation. After cooling to rt, they were diluted with MeOH (0.25 mL). These examples were purified from their corresponding solutions by RP preparative HPLC using Method H. Analytical data for these examples in Table 2 are reported as follows: compound retention times were recorded using HPLC/MS conditions (Method E), and the molecular masses of the compounds were determined by MS (ES) by the formula m/z.

Example 143

(E)-N-(4-(3,4-dichlorophenyl)but-3-enyl)-4-hydroxy-1-methyl-5-oxo-2,5-dihydro-1H-pyrrole-3-carboxamide

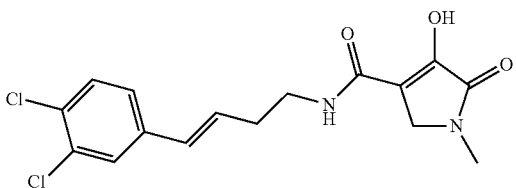 [SMILES: CN1CC(C(=O)NCC/C=C/c2ccc(Cl)c(Cl)c2)=C(O)C1=O]

Example 143A (Z)—N-((E)-4-(3,4-dichlorophenyl)but-3-enyl)-2-(2,2-dimethyl-5-oxo-1,3-dioxolan-4-ylidene)acetamide

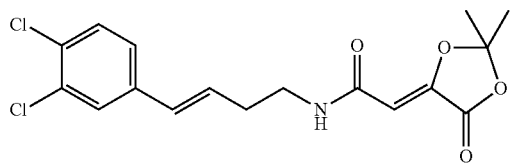 [SMILES: CC1(C)OC(=O)/C(=C/C(=O)NCC/C=C/c2ccc(Cl)c(Cl)c2)O1]

By appropriate application of method used to synthesize Intermediate 5, Intermediate 6 (41 mg, 0.19 mmol) was converted to Example 143 A (38 mg, 0.10 mmol, 54% yield). HPLC/MS (Method D) RT=1.06 min, [M+H]+ 370.

Example 143

The mixture of paraformaldehyde (3.08 mg, 0.103 mmol) and Methylamine (0.051 mL, 0.10 mmol) in MeOH (2 mL) was subject to microwave irridiation for 10 min at 60° C., followed by addition of Example 143A (38 mg, 0.10 mmol) and the reaction mixture was subject to microwave irradiation at 100° C. for 10 min. The reaction mixture was purified by RP preparative HPLC using Method T to give Example 143 (9.2 mg, 0.025 mmol, 24% yield). HPLC/MS (Method D) RT=0.95 min, [M+H]+ 355; $^1$H NMR (500 MHz, methanol-$d_3$) (δ ppm): 2.48 (q, J=6.69 Hz, 2H) 3.06 (s, 3H) 3.52 (q, J=6.69 Hz, 2H) 4.04 (s, 2H) 6.18 (td, J=15.69, 7.15, 7.03 Hz, 1H) 6.38 (d, J=15.81 Hz, 1H) 6.94 (t, J=5.40 Hz, 1H) 7.15 (dd, J=8.28, 2.01 Hz, 1H) 7.33 (d, J=8.28 Hz, 1H) 7.40 (d, J=2.01 Hz, 1H)

By appropriate application of method described for Example 143, Example 151 was synthesized.

Example 167

N-(3-(3,4-dichlorophenyl)propyl)-1-(2-(4-fluorophenoxy)ethyl)-4-hydroxy-5-oxo-2,5-dihydro-1H-pyrrole-3-carboxamide

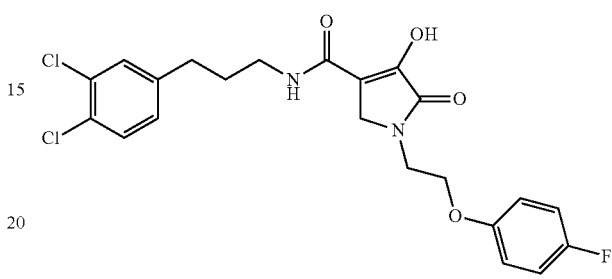

To a solution of 2-(4-fluorophenoxy)ethanamine (0.022 g, 0.14 mmol) in MeOH (3 mL) was added DIPEA (0.024 mL, 0.14 mmol). The mixture was stirred for 5 min at rt, then paraformaldehyde (4.19 mg, 0.140 mmol) was added. The mixture heated at 60° C. for 10 min using microwave irradiation. The reaction was cooled to rt, then Intermediate 5 (50 mg, 0.140 mmol) was added in a single portion. The reaction mixture was heated at 100° C. for 15 min using microwave irradiation, then stirred at rt for 16 h. The reaction mixture was diluted with MeOH:H$_2$O (9:1) containing 0.1% TFA, then purified by RP preparative HPLC (Method C) to obtain 9.2 mg (14% yield) of Example 167. HPLC/MS (Method C) RT=3.35 min, [M+H]+ 468; $^1$H NMR (500 MHz, methanol-$d_3$) (δ ppm): 1.83-1.95 (m, 2H), 2.66 (t, J=7.70 Hz, 2H), 3.36 (t, J=6.87 Hz, 2H), 3.85 (t, J=5.22 Hz, 2H), 4.11-4.20 (m, 4H), 6.91 (d, J=4.40 Hz, 1H), 6.93 (d, J=3.85 Hz, 1H), 6.99 (t, J=8.80 Hz, 2H), 7.14 (dd, J=8.25, 2.20 Hz, 1H), 7.35-7.41 (m, 2H).

By appropriate application of the methods described for Example 167, Examples 169 and 175 were synthesized.

Example 177

1-(2-(2-(2-aminoethoxy)ethoxy)ethyl)-N-(3-(3,4-dichlorophenyl)-propyl)-4-hydroxy-5-oxo-2,5-dihydro-1H-pyrrole-3-carboxamide trifluoroacetic acid salt

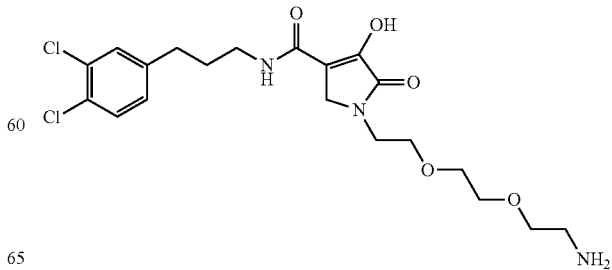

Example 177A tert-butyl 2-(2-(2-(4-(3-(3,4-dichlorophenyl)propyl-carbamoyl)-3-hydroxy-2-oxo-2,5-dihydro-1H-pyrrol-1-yl)ethoxy)ethoxy)ethylcarbamate

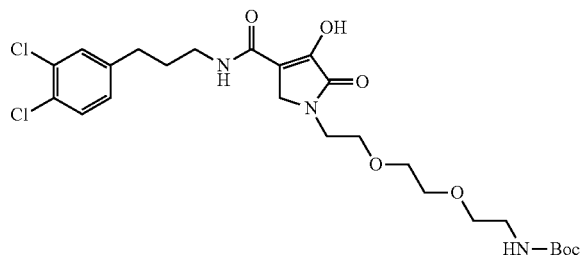 [SMILES: CC(C)(C)OC(=O)NCCOCCOCCN1CC(C(=O)NCCCc2ccc(Cl)c(Cl)c2)=C(O)C1=O]

To a solution of tert-butyl 2-(2-(2-aminoethoxy)ethoxy)ethylcarbamate (311 mg, 1.3 mmol) in MeOH (5 mL) was added paraformaldehyde (38 mg, 1.3 mmol). The mixture was heated at 60° C. for 10 min using microwave irradiation. The resulting solution was added to a second vial containing Intermediate 5 (449 mg, 1.252 mmol). The reaction mixture was heated at 100° C. for 15 min using microwave irradiation. After cooling to rt, the reaction was diluted with EtOAc, washed with 5% aqueous citric acid and saturated aqueous NaCl:$H_2O$ (1:1), dried over $MgSO_4$, filtered and evaporated to dryness in vacuo to obtain 680 mg (68% yield) of Example 177A. HPLC/MS (Method C) RT=3.34 min, [M+H]$^+$ 560.3.

Example 177

By appropriate application of the method used to synthesize Intermediate 3, Example 177A (680 mg, 1.2 mmol) was converted to Example 177 (300 mg, 42% yield). HPLC/MS (Method C) RT=2.75 min, [M+H]$^+$ 461; $^1$H NMR (500 MHz, MeOH-$d_3$) (δ ppm): 1.86-1.94 (m, 3H), 2.68 (t, J=7.70 Hz, 3H), 3.10-3.14 (m, 3H), 3.35 (s, 3H), 3.37 (t, J=6.87 Hz, 3H), 3.65 (s, 5H), 3.66-3.71 (m, 9H), 4.11 (s, 3H), 7.14-7.17 (m, 1H), 7.40 (s, 2H), 7.41 (s, 1H).

Example 178

1-(2-(2-(2-(3-aminopropanamido)ethoxy)ethoxy)ethyl)-N-(3-(3,4-dichlorophenyl)propyl)-4-hydroxy-5-oxo-2,5-dihydro-1H-pyrrole-3-carboxamide trifluoroacetic acid salt

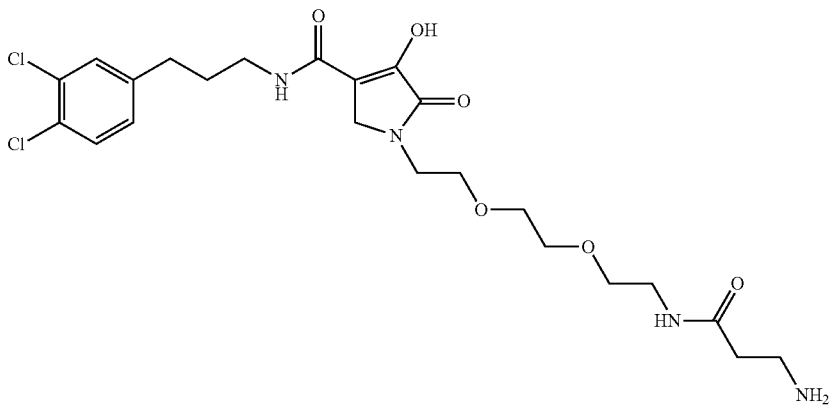 [SMILES: NCCC(=O)NCCOCCOCCN1CC(C(=O)NCCCc2ccc(Cl)c(Cl)c2)=C(O)C1=O]

Example 178A

N-(3-(3,4-dichlorophenyl)propyl)-1-(2-(2-(2-(3-(1,3-dioxoisoindolin-2-yl)propanamido)ethoxy)ethoxy)ethyl)-4-hydroxy-5-oxo-2,5-dihydro-1H-pyrrole-3-carboxamide

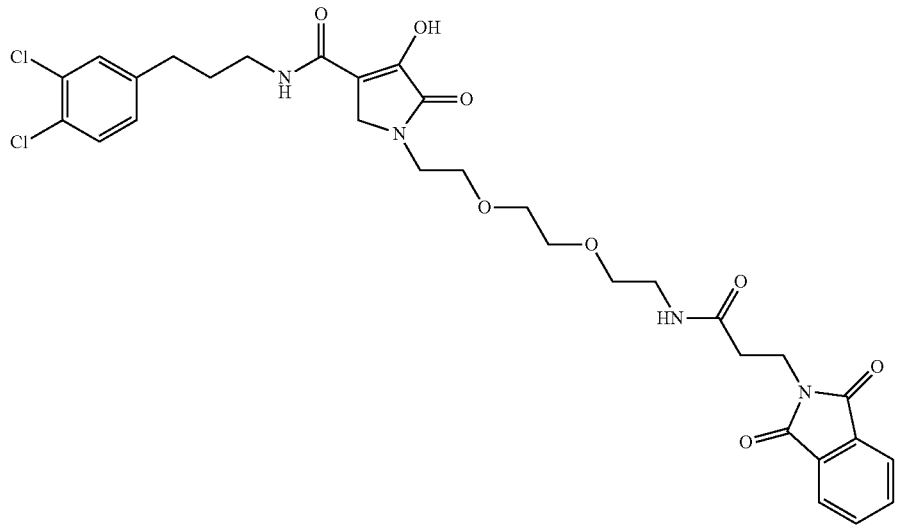 [SMILES: O=C(CCN1C(=O)c2ccccc2C1=O)NCCOCCOCCN1CC(C(=O)NCCCc2ccc(Cl)c(Cl)c2)=C(O)C1=O]

By appropriate application of the method used to provide Example 177A, Intermediate 5 (219 mg, 0.61 mmol), Intermediate 7 (214 mg, 0.61 mmol) and paraformaldehyde (18 mg, 0.61 mmol) were converted to Example 178A (66 mg, 13% yield). HPLC/MS (Method C) RT=3.10 min, [M+H]$^+$ 662.

Example 178

To a solution of Example 178A (66 mg, 0.10 mmol) in MeOH (1 mL) was added NH$_2$NH$_2$.H$_2$O (0.029 mL, 0.599 mmol). The reaction mixture was stirred at rt for 4 h, diluted with EtOAc and evaporated in vacuo. The crude product was dissolved ACN/H$_2$O (1:1) containing 0.1% TFA, then purified using RP preparative HPLC (Method J) to obtain 8.7 mg (12% yield) of Example 178. HPLC/MS RT=2.70 min, [M+H]$^+$ 532. $^1$H NMR (500 MHz, methanol-d$_3$) (δ ppm): 1.83-1.95 (m, 2H), 2.59 (t, J=6.60 Hz, 2H), 2.66 (t, J=7.70 Hz, 2H), 3.17 (t, J=6.32 Hz, 2H), 3.35 (t, J=6.05 Hz, 4H), 3.52 (t, J=5.22 Hz, 2H), 3.54-3.61 (m, 4H), 3.61-3.71 (m, 5H), 4.10 (s, 2H), 7.14 (d, J=9.90 Hz, 1H), 7.34-7.44 (m, 2H).

Example 179

N-(3-(3,4-dichlorophenyl)propyl)-4-(3-(3,4-dichlorophenyl)-propylamino)-1-ethyl-5-oxo-2,5-dihydro-1H-pyrrole-3-carboxamide

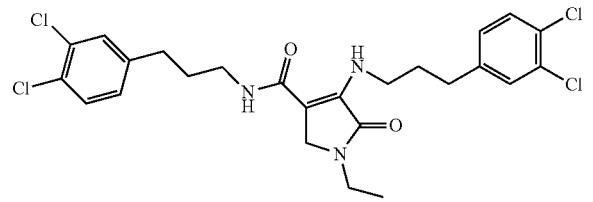 [SMILES: CCN1CC(C(=O)NCCCc2ccc(Cl)c(Cl)c2)=C(NCCCc2ccc(Cl)c(Cl)c2)C1=O]

To a solution of Intermediate 8 (20 mg, 0.12 mmol) in CH$_2$Cl$_2$ (1 mL) was added oxalyl chloride (0.011 mL, 0.13 mmol). The reaction mixture was stirred at rt for 2.5 h. The reaction mixture was concentrated. The intermediate was dissolved in DCM (1 mL) and 3-(3,4-dichlorophenyl)propan-1-amine (23.85 mg, 0.117 mmol) and Hunig's base (0.041 mL, 0.234 mmol) were added. The resulting reaction mixture was stirred at rt for 16 h, then concentrated in vacuo, redissolved in MeOH and purified by RP preparative HPLC (Method I) to provide Example 179 (5 mg, 7.2% yield). HPLC/MS (Method D) RT=1.0 min, [M+H]$^+$ 546.1; $^1$H NMR (400 MHz, chloroform-d) (δ ppm): 7.33 (2H, m), 7.24 (1H, d, J=2.01 Hz), 7.19 (1H, d, J=1.76 Hz), 6.98 (1H, m), 6.92 (1H, dd, J=8.28, 1.76 Hz), 4.55 (1H, d, J=8.78 Hz), 3.84 (2H, m), 3.81 (1H, dd, J=7.40, 3.64 Hz), 3.67 (1H, d, J=4.02 Hz), 3.57 (2H, d, J=7.03 Hz), 3.27 (1H, m), 3.11 (1H, dd, J=13.30, 5.52 Hz), 3.02 (1H, s), 2.81 (1H, m), 2.57 (3H, m), 1.97 (1H, s), 1.81 (2H, m), 1.19 (3H, t, J=6.53 Hz).

Example 180

N-(3-(3,4-Dichlorophenyl)propyl)-1-ethyl-4-hydroxy-5-oxo-2,5-dihydro-1H-pyrrole-3-carboxamide

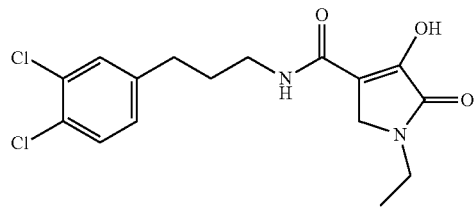 [SMILES: CCN1CC(C(=O)NCCCc2ccc(Cl)c(Cl)c2)=C(O)C1=O]

Example 180A

N-(3-(3,4-Dichlorophenyl)propyl)-1-ethyl-4-methoxy-5-oxo-2,5-dihydro-1H-pyrrole-3-carboxamide

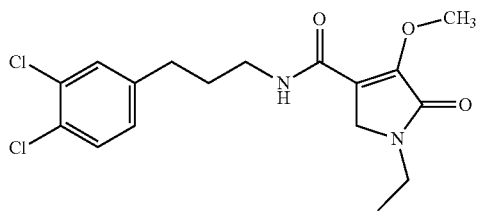 [SMILES: CCN1CC(C(=O)NCCCc2ccc(Cl)c(Cl)c2)=C(OC)C1=O]

To a solution of Intermediate 9 (17 mg, 0.09 mmol) in CH$_2$Cl$_2$ (1 mL) was added oxalyl chloride (9.0 μL, 0.10 mmol) at rt. The reaction mixture was stirred at rt 4 h. The reaction mixture was concentrated. The residue was dissolved in DCM (1 mL), followed by the addition of Intermediate 1 (19 mg, 0.09 mmol) and DIPEA (0.016 mL, 0.09 mmol). The reaction was stirred at room temperature for 16 h. The product was purified by silica gel chromatography (12 g silica gel; 50% EtOAC:MeOH (10:1) in hexanes isocratic) to give Example 180A (16.5 mg, 47% yield). HPLC/MS (Method D) RT=1.0 min, [M+H]$^+$ 371.2; $^1$H NMR (400 MHz, chloroform-d) (δ ppm): 1.20 (t, J=7.28 Hz, 3H), 1.88 (dt, J=14.74, 7.31 Hz, 2H), 2.59-2.72 (m, 2H), 3.38 (q, J=6.86 Hz, 2H), 3.50 (q, J=7.28 Hz, 2H), 3.99 (s, 2H), 4.34 (s, 3H), 6.96 (br. s., 1H), 7.00-7.07 (m, 1H), 7.29 (d, J=2.01 Hz, 1H), 7.35 (d, J=8.28 Hz, 1H).

Example 180

To a solution of Example 180A (17 mg, 0.045 mmol) in CH$_2$Cl$_2$ (1 mL) was added BCl$_3$ (2.0 M in CH$_2$Cl$_2$; 0.06 mL, 0.12 mmol). The reaction mixture was stirred at rt for 2.75 h. Additional BCl$_3$ (2.0 M in CH$_2$Cl$_2$; 0.06 mL, 0.12 mmol) was added and the reaction mixture was stirred at room rt for an additional 2 h. The excess BCl$_3$ was quenched with MeOH. The mixture was concentrated, dissolved in MeOH and purified by RP preparative HPLC (Method I) to obtain 7.7 mg (44% yield) of Example 180. HPLC/MS (Method D) RT=0.95 min; [M+H]$^+$ 357.3; $^1$H NMR (400 MHz, chloroform-d) (δ ppm): 7.34 (1H, d, J=8.34 Hz), 7.29 (1H, m), 7.04 (1H, dd, J=8.08, 2.02 Hz), 6.92 (1H, t, J=5.31 Hz), 4.07 (2H, s), 3.58 (2H, q, J=7.33 Hz), 3.41 (2H, q, J=6.82 Hz), 2.65 (2H, m), 1.90 (2H, ddd, J=14.78, 7.33, 7.20 Hz), 1.23 (3H, m).

Example 181

1-ethyl-4-hydroxy-5-oxo-N-(4-sulfamoylphenethyl)-2,5-dihydro-1H-pyrrole-3-carboxamide

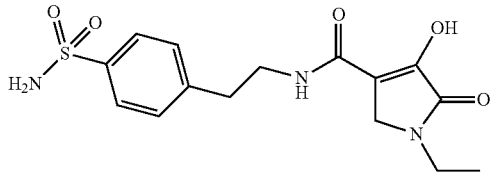 [SMILES: CCN1CC(C(=O)NCCc2ccc(S(N)(=O)=O)cc2)=C(O)C1=O]

Example 181A 1-ethyl-4-methoxy-5-oxo-N-(4-sulfamoylphenethyl)-2,5-dihydro-1H-pyrrole-3-carboxamide

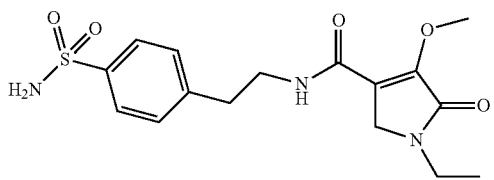 [SMILES: CCN1CC(C(=O)NCCc2ccc(S(N)(=O)=O)cc2)=C(OC)C1=O]

By appropriate application of method described for Example 180A, 4-(2-aminoethyl)benzenesulfonamide (64.9 mg, 0.324 mmol) and 1-ethyl-4-hydroxy-5-oxo-2,5-dihydro-1H-pyrrole-3-carbonyl chloride (66.0 mg, 0.324 mmol) were converted to Example 181A (57 mg, 0.15 mmol, 45% yield). HPLC/MS (Method D) RT=0.65 min, [M+H]F 390.1; $^1$HNMR (400 MHz, CHLOROFORM-d) δ ppm 1.13-1.28 (m, 3H) 2.96 (t, J=6.87 Hz, 2H) 3.50 (q, J=7.15 Hz, 2H) 3.60-3.72 (m, 2H) 3.99 (s, 2H) 4.25 (s, 3H) 7.00 (d, J=2.20 Hz, 1H) 7.39 (d, J=8.25 Hz, 2H) 7.89 (d, J=8.25 Hz, 2H).

Example 181

By appropriate application of method described for Example 180, Example 181A (57 mg, 0.15 mmol) was converted to Example 181 (38 mg, 0.10 mmol, 69% yield). HPLC/MS (Method D) RT=0.60 min, [M+H]F 354.1; $^1$H NMR (500 MHz, METHANOL-$d_3$) δ ppm 1.19 (t, J=7.15 Hz, 3H) 2.95 (t, J=7.15 Hz, 2H) 3.50 (q, J=7.15 Hz, 2H) 3.60 (t, J=7.15 Hz, 2H) 3.98 (s, 2H) 7.43 (m, J=8.25 Hz, 2H) 7.83 (m, J=8.25 Hz, 2H)

Example 182

1-ethyl-4-hydroxy-N-(3-(methyl(phenyl)amino)propyl)-5-oxo-2,5-dihydro-1H-pyrrole-3-carboxamide

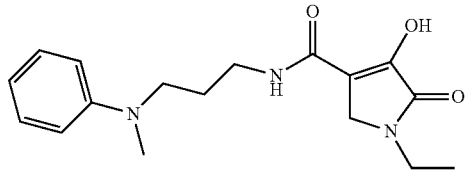 [SMILES: CCN1CC(C(=O)NCCCN(C)c2ccccc2)=C(O)C1=O]

Example 182A 1-ethyl-4-methoxy-N-(3-(methyl(phenyl)amino)propyl)-5-oxo-2,5-dihydro-1H-pyrrole-3-carboxamide

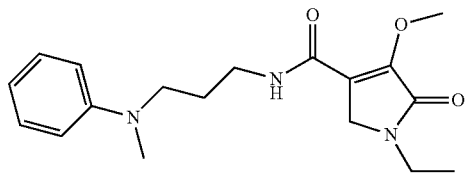 [SMILES: CCN1CC(C(=O)NCCCN(C)c2ccccc2)=C(OC)C1=O]

By appropriate application of method described for Example 180A, N1-methyl-N1-phenylpropane-1,3-diamine (53.2 mg, 0.324 mmol) and 1-ethyl-4-hydroxy-5-oxo-2,5-dihydro-1H-pyrrole-3-carbonyl chloride (66.0 mg, 0.324 mmol) were converted to Example 182A (54 mg, 0.16 mmol, 49% yield). HPLC/MS (Method D) RT=0.60 min, [M+H]$^+$ 354.2; $^1$H NMR (400 MHz, CHLOROFORM-d) δ ppm 1.20 (t, J=7.42 Hz, 3H) 1.74-1.90 (m, 2H) 3.18 (s, 3H) 3.40 (q, J=6.23 Hz, 2H) 3.50 (d, J=7.70 Hz, 1H) 3.53-3.61 (m, 2H) 3.93-4.00 (m, 2H) 4.35 (s, 3H) 7.24-7.33 (m, 1H) 7.39-7.48 (m, 1H) 7.48-7.57 (m, 4H) 12.41 (br. s., 1H).

Example 182

By appropriate application of method described for Example 180, Example 182A (51 mg, 0.15 mmol) was converted to Example 182 (40 mg, 0.12 mmol, 79% yield). HPLC/MS (Method D) RT=0.56 min, [M+H]$^+$ 318.2; $^1$H NMR (500 MHz, METHANOL-$d_3$) δ ppm 1.21 (t, J=7.15 Hz, 3H) 1.72-1.86 (m, 2H) 3.28 (s, 3H) 3.39 (t, J=6.60 Hz, 2H) 3.52 (q, J=7.33 Hz, 2H) 3.61-3.72 (m, 2H) 4.02 (s, 2H) 7.54 (d, J=6.60 Hz, 1H) 7.57-7.67 (m, 4H).

Example 184

4-(benzylamino)-N-(3-(3,4-dichlorophenyl)propyl)-1-ethyl-5-oxo-2,5-dihydro-1H-pyrrole-3-carboxamide

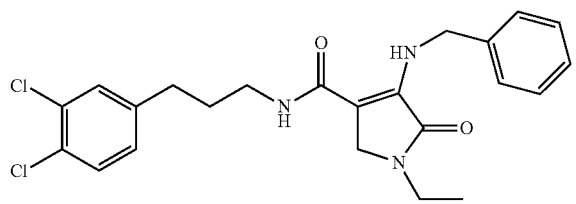 [SMILES: CCN1CC(C(=O)NCCCc2ccc(Cl)c(Cl)c2)=C(NCc2ccccc2)C1=O]

To a solution of Example 180 (20 mg, 0.06 mmol) and benzylamine (6 µL, 0.06 mmol) in EtOH (0.5 mL) was added a drop of HOAc. The reaction mixture was heated at 100° C. for 1 h using microwave irradiation, and then was concentrated in vacuo. The residue was dissolved in MeOH and purified by RP preparative HPLC (Method C) to obtain 10.1 mg (0.021 mmol, 38% yield) of Example 184. HPLC/MS (Method D) RT=1.14 min, [M+H]$^+$ 446.3; $^1$H NMR (400 MHz, chloroform-d) (δ ppm): 1.20 (t, J=7.28 Hz, 3H), 1.84 (quin, J=7.34 Hz, 2H), 3.34 (q, J=6.78 Hz, 2H), 3.50 (q, J=7.28 Hz, 2H), 3.78 (s, 2H), 4.93 (t, J=5.52 Hz, 1H), 5.01 (d, J=6.53 Hz, 2H), 7.02 (dd, J=8.16, 2.13 Hz, 1H), 7.18-7.26 (m, 1H), 7.27-7.39 (m, 6H), 7.49 (t, J=6.02 Hz, 1H).

Example 185

N-(3-(3,4-dichlorophenyl)propyl)-1-ethyl-4-(methylamino)-5-oxo-2,5-dihydro-1H-pyrrole-3-carboxamide

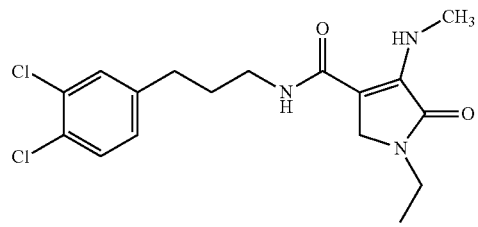 [SMILES: CCN1CC(C(=O)NCCCc2ccc(Cl)c(Cl)c2)=C(NC)C1=O]

To a solution of Example 180 (20 mg, 0.06 mmol) and CH$_3$NH$_2$ (2.0 M in MeOH, 0.06 mL, 0.1 mmol) in EtOH (0.5 mL) was added a drop of HOAc. The reaction mixture was heated at 100° C. for 1 h using microwave irradiation. Additional CH$_3$NH$_2$ (2.0 M in MeOH, 0.06 mL, 0.1 mmol) was added and the reaction was microwaved at 100° C. for 30 min. The reaction mixture was concentrated in vacuo and purified by silica gel chromatography (12 g silica gel; using linear gradient of 0-100% EtOAc in hexanes over 20 min) to obtain 10 mg (50% yield) of Example 185. HPLC/MS (Method F) RT=7.03 min, [M+H]$^+$ 370.1; $^1$H NMR (400 MHz, chloroform-d) (δ ppm): 1.19 (t, J=7.15 Hz, 3H), 1.87 (qd, J=7.33, 7.15 Hz, 2H), 2.65 (t, J=7.42 Hz, 2H), 3.28 (d, J=6.05 Hz, 3H), 3.37 (q, J=6.60 Hz, 2H), 3.49 (q, J=7.15 Hz, 2H), 3.78 (s, 2H), 4.86-4.97 (m, 1H), 7.04 (d, J=6.60 Hz, 2H), 7.29 (s, 1H), 7.35 (d, J=8.25 Hz, 1H).

Example 186

4-amino-N-(3-(3,4-dichlorophenyl)propyl)-1-ethyl-5-oxo-2,5-dihydro-1H-pyrrole-3-carboxamide

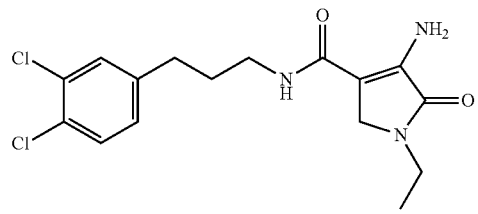 [SMILES: CCN1CC(C(=O)NCCCc2ccc(Cl)c(Cl)c2)=C(N)C1=O]

A solution of Example 180 (20 mg, 0.06 mmol) and ammonium formate (7 mg, 0.1 mmol) in EtOH (0.5 mL) was heated at 100° C. for 90 min using microwave irradiation. The reaction mixture was concentrated in vacuo and purified by silica gel chromatography (12 g silica gel; using linear gradient of 0-100% EtOAc in hexanes over 20 min) to give 8.48 mg (42.1% yield) of Example 186 as a pale yellow solid. HPLC/MS (Method C) RT=1.74 min, [M+H]$^+$ 356.3; $^1$H-NMR (400 MHz, chloroform-d) (δ ppm): 1.21 (t, J=7.15 Hz, 3H), 1.88 (dq, J=7.42, 7.24 Hz, 2H), 2.65 (t, J=7.42 Hz, 2H), 3.33-3.44 (m, 2H), 3.54 (q, J=7.33 Hz, 2H), 3.79 (s, 2H), 4.98 (br. s., 1H), 5.74 (br. s., 2H), 7.04 (dd, J=8.24, 2.20 Hz, 1H), 7.28-7.32 (m, 1H), 7.35 (d, J=8.24 Hz, 1H).

Example 187

3-(4-(3-(3,4-dichlorophenyl)propylcarbamoyl)-3-hydroxy-2-oxo-2,5-dihydro-1H-pyrrol-1-yl)propanoic acid

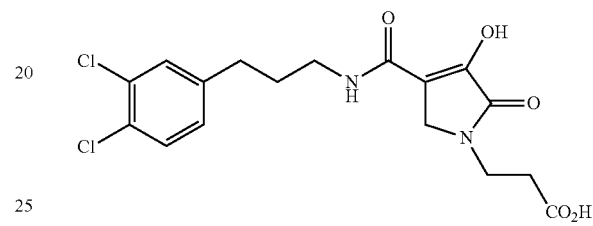

Example 187A ethyl 3-(4-(3-(3,4-dichlorophenyl)propylcarbamoyl)-3-hydroxy-2-oxo-2,5-dihydro-1H-pyrrol-1-yl)propanoate

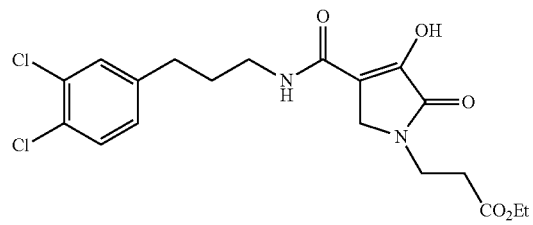 [SMILES: CCOC(=O)CCN1CC(C(=O)NCCCc2ccc(Cl)c(Cl)c2)=C(O)C1=O]

To a solution of ethyl 3-aminopropanoate hydrochloride (30.0 mg, 0.195 mmol) in methanol (3 mL) was added DIPEA (0.102 mL, 0.586 mmol) and paraformaldehyde (5.87 mg, 0.195 mmol). The reaction was heated to 60° C. for 5 min using microwave irradiation. The solution was cooled to rt and transferred to a second vessel charged with Intermediate 5 (70 mg, 0.195 mmol). The reaction mixture was heated to 100° C. for 15 min using microwave irradiation. After cooling to rt, the reaction was diluted with EtOAc (300 mL) containing 5% citric acid (3 mL). The mixture was washed with a solution of saturated brine and water (1:1), dried over MgSO$_4$, filtered and evaporated to dryness in vacuo to provide crude Example 187A (84 mg, 90% yield), which was carried onto the next step without further purification. HPLC/MS (Method C) RT=2.90 min, [M+H]$^+$ 430.0.

Example 187

To a solution of Example 187A (84 mg, 0.196 mmol) in THF (1.5 mL) was added a 1.0 M solution of LiOH (0.489 mL, 0.489 mmol). The reaction mixture was stirred at rt for 4 h. The solvent was removed in vacuo and the residue was dissolved in ACN/H$_2$O (9:1 containing 0.1% TFA) and purified according to Method J to obtain Example 187 (19 mg, 24% yield). HPLC/MS (Method C) RT=2.18 min, [M+H]+ 402; ¹H NMR (500 MHz, MeOH-d₃) (δ ppm): 1.85-1.93 (m, 2H), 2.62-2.70 (m, 4H), 3.36 (t, J=6.87 Hz, 2H), 3.73 (t, J=6.87 Hz, 2H), 4.04 (s, 2H), 7.15 (d, J=8.25 Hz, 1H), 7.36-7.42 (m, 2H).

By appropriate application of the methods described for Example 187, Examples 190 was synthesized.

Example 193

N-(3-(3,4-dichlorophenyl)propyl)-1-(4-fluorophenethyl)-4-hydroxy-2-methyl-5-oxo-2,5-dihydro-1H-pyrrole-3-carboxamide

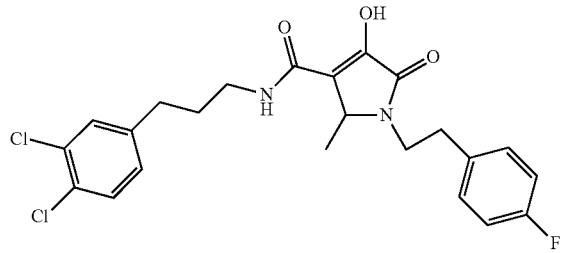 [SMILES: CC1C(C(=O)NCCCc2ccc(Cl)c(Cl)c2)=C(O)C(=O)N1CCc1ccc(F)cc1]

To a solution of 2-(4-fluorophenyl)ethanamine (0.044 mL, 0.335 mmol) in CH₃OH (4 mL) was added DIPEA (0.146 mL, 0.837 mmol) and a 1.7 M methanolic solution of acetaldehyde (0.197 mL, 0.335 mmol). The reaction mixture was stirred at rt for 2 h. The solution was added to a second vial charged with Intermediate 5 (100 mg, 0.279 mmol). The reaction mixture was heated to 100° C. for 10 min using microwave irradiation. The reaction mixture was cooled to rt and diluted with EtOAc (200 mL), washed with 5% citric acid and saturated NaCl/H₂O (1:1), dried over MgSO₄, filtered and evaporated to dryness in vacuo. The residue was dissolved in MeOH/H₂O (9:1 containing 0.1% TFA), then purified using Method I to obtain Example 193 (15 mg, 11% yield). HPLC/MS (Method B) RT=3.40 min, [M+H]+ 466.0; ¹H NMR (500 MHz, CH₃OH-d₃) (δ ppm): 1.33 (d, J=6.60 Hz, 3H), 1.82-1.93 (m, 2H), 2.66 (t, J=7.70 Hz, 2H), 2.87 (s, 1H), 2.93 (d, J=7.70 Hz, 2H), 3.35 (s, 1H), 3.38 (dd, J=14.30, 7.70 Hz, 2H), 7.00 (t, J=8.80 Hz, 2H), 7.15 (d, J=8.25 Hz, 1H), 7.24 (dd, J=8.25, 5.50 Hz, 2H), 7.36-7.42 (m, 2H).

Example 194

N-(3-(3,4-dichlorophenyl)propyl)-4-hydroxy-2-methyl-5-oxo-1-(2-phenoxyethyl)-2,5-dihydro-1H-pyrrole-3-carboxamide

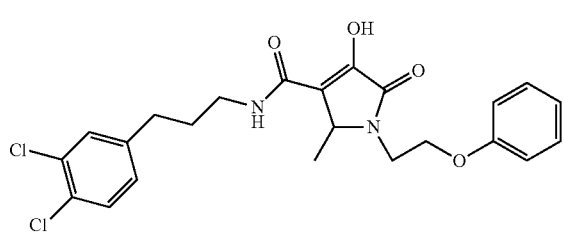 [SMILES: CC1C(C(=O)NCCCc2ccc(Cl)c(Cl)c2)=C(O)C(=O)N1CCOc1ccccc1]

Example 194 was obtained by appropriate application of the method used to provide Example 193. HPLC/MS (Method B) RT=3.40 min, [M+H]+ 464.0; ¹H NMR (500 MHz, CH₃OH-d₃) (δ ppm): 1.44 (d, J=6.60 Hz, 3H), 1.85-1.94 (m, 2H), 2.67 (t, J=7.42 Hz, 2H), 3.33-3.45 (m, 2H), 3.60 (s, 1H), 4.08-4.15 (m, 2H), 4.17-4.25 (m, 1H), 4.41 (d, J=6.60 Hz, 1H), 6.89-6.95 (m, 3H), 7.12-7.17 (m, 1H), 7.25 (d, J=7.15 Hz, 1H), 7.38 (s, 1H), 7.39 (d, J=4.95 Hz, 1H).

Example 197

N-(3-(3,4-dichlorophenyl)propyl)-7-hydroxy-3,6-dioxo-1,2,3,4,6,8a-hexahydropyrrolo[1,2-a]pyrazine-8-carboxamide

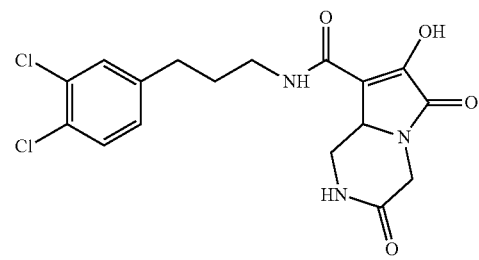 [SMILES: O=C1CN2C(=O)C(O)=C(C(=O)NCCCc3ccc(Cl)c(Cl)c3)C2CN1]

Example 197A ethyl 2-(2-((tert-butoxycarbonylamino)methyl)-3-(3-(3,4-dichlorophenyl)propylcarbamoyl)-4-hydroxy-5-oxo-2,5-dihydro-1H-pyrrol-1-yl)acetate

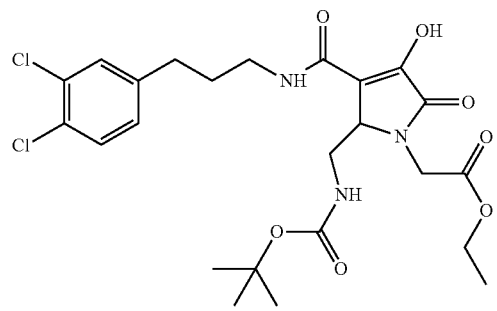 [SMILES: CCOC(=O)CN1C(=O)C(O)=C(C(=O)NCCCc2ccc(Cl)c(Cl)c2)C1CNC(=O)OC(C)(C)C]

To a solution of ethyl 2-aminoacetate hydrochloride (117 mg, 0.837 mmol) in CH₃OH (5 mL) were added DIPEA (0.439 mL, 2.51 mmol) and tert-butyl 2-oxoethylcarbamate (133 mg, 0.837 mmol). The reaction mixture was heated to 60° C. for 10 min using microwave irradiation. The resulting solution was added to a second vessel charged with Intermediate 5 (300 mg, 0.837 mmol). The reaction mixture was heated to 100° C. for 15 min using microwave irradiation. The reaction was cooled to rt, diluted with EtOAc (300 mL), quenched with 5% aqueous citric acid (7 mL), washed with saturated brine/H₂O (1:1), dried over MgSO₄, filtered and evaporated to dryness in vacuo. Isolated Example 197A (300 mg, 0.413 mmol, 49% yield) as a crude product was used without further purification in the next step. HPLC/MS (Method C) RT=3.5 min, [M+H]+ 544.0.

Example 197B 2-(2-((tert-butoxycarbonylamino)methyl)-3-(3-(3,4-dichlorophenyl)propylcarbamoyl)-4-hydroxy-5-oxo-2,5-dihydro-1H-pyrrol-1-yl)acetic acid

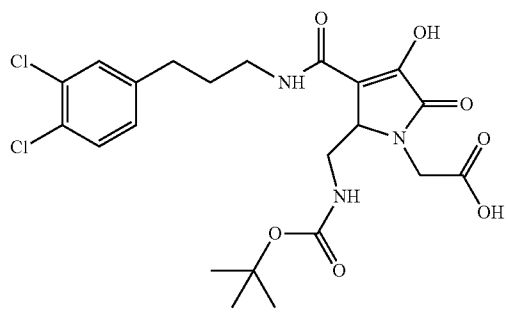 [SMILES: CC(C)(C)OC(=O)NCC1C(C(=O)NCCCc2ccc(Cl)c(Cl)c2)=C(O)C(=O)N1CC(=O)O]

To a solution of Example 197A (300 mg, 0.551 mmol) in THF (5 mL) was added a 1M solution of aqueous LiOH (3.31 mL, 3.31 mmol). The reaction mixture was stirred at rt for 3 h. The solvents were removed in vacuo. The residue was dissolved CH$_3$OH/H$_2$O (9:1) containing 0.1% TFA and purified by Method I to provide Example 197B (40 mg, 14% yield). HPLC/MS (Method A) RT=2.45 min, [M+H]+ 516.1.

Example 197C.

2-(2-(aminomethyl)-3-(3-(3,4-dichlorophenyl)propylcarbamoyl)-4-hydroxy-5-oxo-2,5-dihydro-1H-pyrrol-1-yl)acetic acid

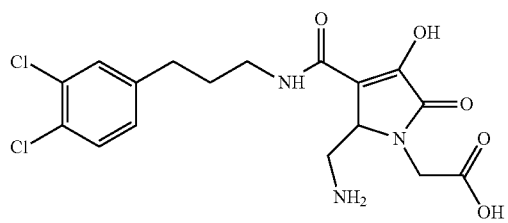 [SMILES: NCC1C(C(=O)NCCCc2ccc(Cl)c(Cl)c2)=C(O)C(=O)N1CC(=O)O]

To a solution of Example 197B (40 mg, 0.077 mmol) in CH$_2$Cl$_2$ (0.8 mL) was added TFA (0.2 mL). The reaction mixture was stirred at rt for 2 h. The reaction was diluted with toluene (imp and concentrated in vacuo to give Example 197C (28 mg, 87% yield). HPLC/MS (Method C) RT=1.4 min, [M+H]+ 417.

Example 197

To a solution of Example 197C (28 mg, 0.053 mmol), EDC (11.13 mg, 0.058 mmol) and HOBT (8.89 mg, 0.058 mmol) in DMF (1 mL) was added N-methylmorpholine (0.029 mL, 0.264 mmol). The reaction mixture was stirred at rt for 16 h. The reaction mixture was diluted with EtOAc (400 mL), washed with saturated brine/H$_2$O (1:1), dried over MgSO$_4$, filtered and evaporated to dryness in vacuo. The residue was triturated with ACN/H$_2$O containing 0.5% TFA. The solids were collected by filtration to yield Example 197 (2.1 mg, 9.3% yield). HPLC/MS (Method C) RT=1.8 min, [M+H]+ 399.0. $^1$H NMR (500 MHz, DMSO-d$_6$) (δ ppm): 1.77 (qd, J=7.33, 7.15 Hz, 2H), 2.59 (t, J=7.42 Hz, 2H), 2.83 (t, J=11.27 Hz, 1H), 3.21 (td, J=12.92, 6.60 Hz, 2H), 3.67-3.79 (m, 2H), 4.22 (d, J=18.15 Hz, 1H), 4.32 (dd, J=10.45, 3.85 Hz, 1H), 7.22 (dd, J=8.25, 2.20 Hz, 1H), 7.44 (br. s., 1H), 7.50 (d, J=2.20 Hz, 1H), 7.52 (d, J=8.25 Hz, 1H), 8.20 (d, J=5.50 Hz, 1H).

Example 198

N-(3-(3,4-dichlorophenyl)propyl)-8-hydroxy-3,7-dioxo-2,3,4,5,7,9a-hexahydro-1H-pyrrolo[1,2-a][1,4]diazepine-9-carboxamide

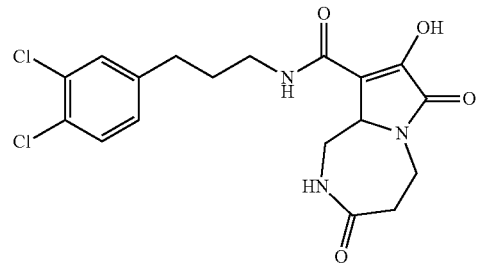 [SMILES: O=C1CCN2C(=O)C(O)=C(C(=O)NCCCc3ccc(Cl)c(Cl)c3)C2CN1]

Example 198A tert-butyl 3-(2-(aminomethyl)-3-(3-(3,4-dichlorophenyl)propyl-carbamoyl)-4-hydroxy-5-oxo-2,5-dihydro-1H-pyrrol-1-yl)propanoate

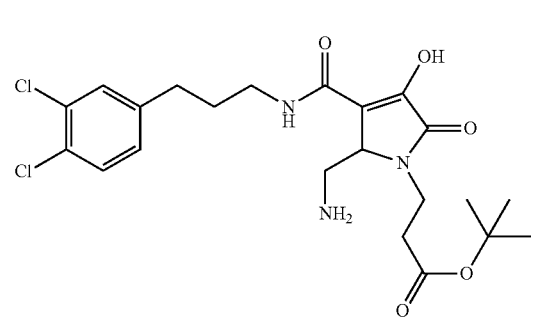 [SMILES: CC(C)(C)OC(=O)CCN1C(=O)C(O)=C(C(=O)NCCCc2ccc(Cl)c(Cl)c2)C1CN]

To a solution of tert-butyl 3-aminopropanoate hydrochloride (114 mg, 0.628 mmol) in CH$_3$OH (3.5 mL) was added DIPEA (0.329 mL, 1.885 mmol) and tert-butyl 2-oxoethylcarbamate (100 mg, 0.628 mmol). The reaction mixture was heated to 60° C. for 10 min using microwave irradiation. The resulting solution was added to a second vessel charged with Intermediate 5 (225 mg, 0.628 mmol). The reaction mixture was heated to 100° C. for 15 min using microwave irradiation. The reaction was cooled to rt, diluted with EtOAc (300 mL), quenched with 20 mL 5% aqueous citric acid, washed with a mixture of saturated brine/H$_2$O (1:1), dried over MgSO$_4$, filtered and evaporated to dryness in vacuo to provide Example 198A (285 mg, 84%), which was used in the next step without further purification. HPLC/MS (Method C) RT=3.5 min, [M+H]+ 487.0.

Example 198B 3-(2-(aminomethyl)-3-(3-(3,4-dichlorophenyl)propylcarbamoyl)-4-hydroxy-5-oxo-2,5-dihydro-1H-pyrrol-1-yl)propanoic acid

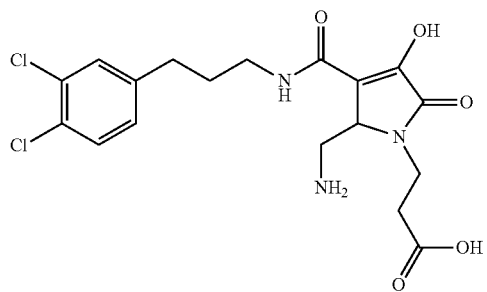 [SMILES: NCC1C(C(=O)NCCCc2ccc(Cl)c(Cl)c2)=C(O)C(=O)N1CCC(=O)O]

To a solution of Example 198A (285 mg, 0.527 mmol) in CH$_2$Cl$_2$ (2 mL) was added TFA (0.6 mL). The reaction mixture was stirred at rt for 16 h. The solvents were removed in vacuo and the residue was dissolved in ACN/H$_2$O (9:1) containing 0.1% TFA. Then purified by preparative HPLC using Method J to provide Example 198B (33 mg, 12%). HPLC/MS (Method C) RT=2.3 min, [M+H]+=431.0.

Example 198

By appropriate application of the method used to give Example 197 from Example 197C, Example 198 (2.5 mg, 7.4% yield) was obtained from Example 198B (33 mg). HPLC/MS (Method C) RT=2.5 min, [M+H]+ 413.0; $^1$H NMR (500 MHz, CH$_3$OH-d$_3$) (δ ppm): 1.85-1.93 (m, 2H), 2.53 (dd, J=14.57, 4.12 Hz, 1H), 2.65-2.71 (m, 2H), 3.03 (dd, J=14.57, 9.07 Hz, 1H), 3.15-3.24 (m, 2H), 3.95-4.02 (m, 1H), 4.24 (d, J=7.15 Hz, 1H), 4.34-4.45 (m, 1H), 7.16 (dd, J=8.25, 2.20 Hz, 1H), 7.35-7.43 (m, 2H).

Example 199

N-(3-(3,4-Dichlorophenyl)propyl)-4-hydroxy-5-oxo-1-(2-oxo-2-(phenylsulfonamido)ethyl)-2,5-dihydro-1H-pyrrole-3-carboxamide

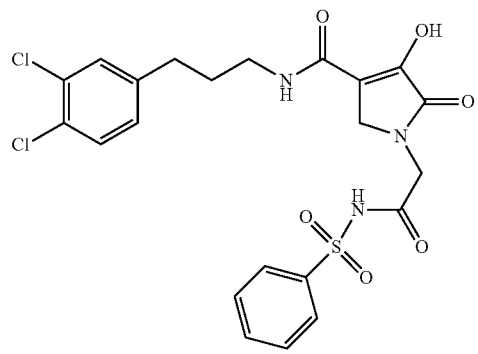 [SMILES: O=C(CN1CC(C(=O)NCCCc2ccc(Cl)c(Cl)c2)=C(O)C1=O)NS(=O)(=O)c1ccccc1]

A solution of Example 190 (22 mg, 0.057 mmol), benzenesulfonamide (8.93 mg, 0.057 mmol), DMAP (3.47 mg, 0.028 mmol), and EDC (10.89 mg, 0.057 mmol) in DMF (0.5 mL) was stirred at rt for 16 h. The reaction mixture was dissolved in ACN/H$_2$O (9:1) containing 0.1% TFA and purified by preparative HPLC using Method J to provide Example 199 (2.5 mg, 7.7% yield). HPLC/MS Method C) RT=2.70 min [M+H]+ 527.0; $^1$H NMR (500 MHz, chloroform-d) (δ ppm): 1.84-1.93 (m, 2H), 2.66 (t, J=7.70 Hz, 2H), 3.97 (s, 2H), 4.21 (s, 2H), 7.15 (dd, J=8.25, 2.20 Hz, 1H), 7.35-7.44 (m, 2H), 7.60 (t, J=7.70 Hz, 2H), 7.69 (d, J=7.15 Hz, 1H), 8.02 (d, J=7.70 Hz, 2H).

By appropriate application of the methods described for Example 199, Examples 200-201 were synthesized.

Example 202

(R)—N-(4-(3,4-dichlorophenyl)butan-2-yl)-1-(2,4-difluorophenyl)-4-hydroxy-5-oxo-2,5-dihydro-1H-pyrrole-3-carboxamide

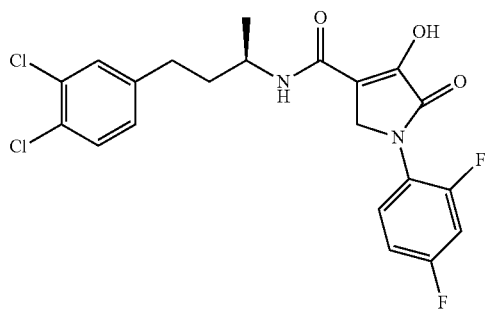 [SMILES: C[C@H](CCc1ccc(Cl)c(Cl)c1)NC(=O)C1=C(O)C(=O)N(c2ccc(F)cc2F)C1]

Example 202A (R)—N-(4-(3,4-dichlorophenyl)butan-2-yl)-1-(2,4-difluorophenyl)-4-ethoxy-5-oxo-2,5-dihydro-1H-pyrrole-3-carboxamide

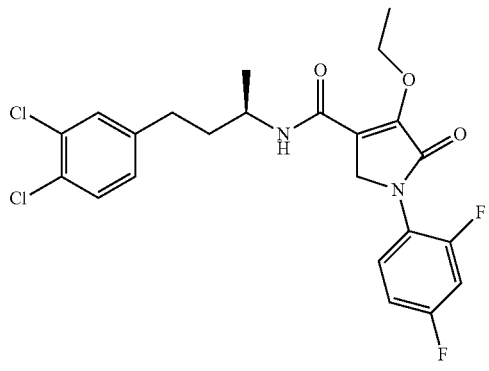 [SMILES: CCOC1=C(C(=O)N[C@H](C)CCc2ccc(Cl)c(Cl)c2)CN(c2ccc(F)cc2F)C1=O]

To a solution of Intermediate 14A (45 mg, 0.15 mmol) in DCM was added TEA (63 µL, 0.45 mmol) and (R)-4-(3,4-dichlorophenyl)butan-2-amine HCl (46 mg, 0.18 mmol). The reaction mixture was stirred at rt for 14 h. The reaction mixture was diluted with DCM, washed with 1N HCl and brine, dried over Na$_2$SO$_4$, and purified by ISCO (0-40% EtOAc/

Hex) to give Example 202A (37 mg, 0.080 mmol, 51% yield) as a yellow solid. HPLC/MS (Method L) RT=2.35 min, [M+H]+ 483.2.

Example 202

To a solution of Example 202A (37 mg, 0.080 mmol) in CHCl$_3$ (1 mL) was added boron trichloride (0.23 mL, 0.23 mmol). The reaction mixture was stirred at rt for 14 h, quenched with MeOH and concentrated. The residue was purified by prep HPLC using a 10 minute gradient from 0 to 100% B (Column: Phenomenex AXIA Luna 300×75 mm 5 nm; Solvent A: 10% ACN-90% H$_2$O-0.1% TFA; Solvent B: 90% ACN-10% H$_2$O-0.1% TFA). The product fraction was collected (RT=8.86 min) and concentrated to give Example 202 (28 mg, 0.060 mmol, 77% yield) as a white solid. HPLC/MS (Method L) RT=2.27 min, [M+H]+ 455.0; $^1$H NMR (500 MHz, Acetone) δ ppm 7.67 (1H, td, J=8.80, 6.05 Hz), 7.45-7.47 (1H, m), 7.23 (1H, dd, J=8.25, 2.20 Hz), 7.15-7.22 (2H, m), 7.08-7.14 (1H, m), 4.39-4.49 (2H, m), 4.11-4.22 (1H, m), 2.68-2.81 (2H, m), 1.83-1.96 (2H, m), 1.25 (3H, d, J=6.60 Hz).

Examples 212, 217, 219, 203, 220, and 222 were synthesized from intermediates following a similar procedure described for Example 202.

Example 224

1-(4-cyanophenyl)-N-(3-(3,4-dichlorophenyl)propyl)-4-hydroxy-5-oxo-2,5-dihydro-1H-pyrrole-3-carboxamide

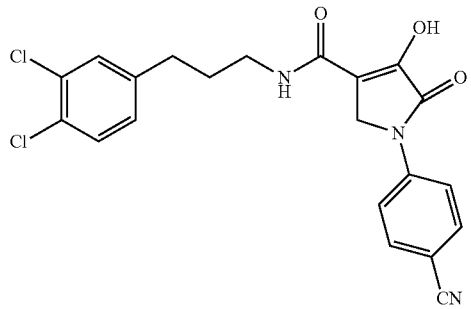 [SMILES: N#Cc1ccc(N2CC(C(=O)NCCCc3ccc(Cl)c(Cl)c3)=C(O)C2=O)cc1]

Zinc (II) cyanide (7.28 mg, 62.0 mmol), Example 203 (20 mg, 41 mmol), and tetrakis(triphenylphosphine)palladium(0) (4.77 mg, 4.13 mmol) were stirred in DMF (0.5 mL) at 130° C. for 10 min in microwave. The reaction mixture was filtered and concentrated to give a yellow solid. The residue was purified by reverse phase preparative HPLC using a 15 minute gradient from 30 to 100% B (Column: Phenomenex AXIA Luna 300×75 mm 5u; Solvent A: 10% ACN-90% H$_2$O-0.1% TFA; Solvent B: 90% ACN-10% H$_2$O-0.1% TFA) to give Example 224 (3.0 mg, 6.3 mmol, 15% yield). HPLC/MS (Method L) RT=2.11 min, [M+H]+ 429.9; $^1$H NMR (400 MHz, MeOD) δ ppm 8.03 (2H, d, J=8.84 Hz), 7.72-7.79 (2H, m), 7.35-7.43 (2H, m), 7.16 (1H, dd, J=8.34, 2.02 Hz), 4.46 (2H, s), 3.41 (2H, t, J=6.95 Hz), 2.69 (2H, t, J=7.58 Hz), 1.93 (2H, qd, J=7.33, 7.07 Hz).

Example 225

N-(4-(3,4-dichlorophenyl)butan-2-yl)-1-ethyl-4-hydroxy-5-oxo-2,5-dihydro-1H-pyrrole-3-carboxamide (racemate)

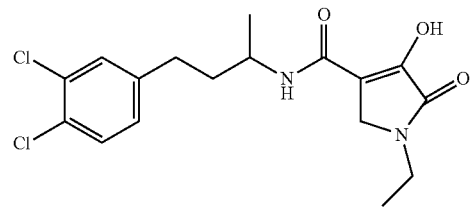 [SMILES: CCN1CC(C(=O)NC(C)CCc2ccc(Cl)c(Cl)c2)=C(O)C1=O]

By appropriate application of method described in Example 180, 4-(3,4-dichlorophenyl)butan-2-amine (racemic) (50 mg, 0.23 mmol) and 1-ethyl-4-methoxy-5-oxo-2,5-dihydro-1H-pyrrole-3-carboxylic acid (85 mg, 0.46 mmol) were converted to Example 225 (racemate) (12 mg, 0.032 mmol, 15% yield for two steps). HPLC/MS (Method D) RT=0.97 min, [M+1]+ 371.1; $^1$H NMR (400 MHz, CHLOROFORM-d) δ ppm 1.16-1.39 (m, 6H) 1.74-1.95 (m, 2H) 2.67 (t, J=7.78 Hz, 2H) 3.62 (q, J=7.03 Hz, 2H) 4.12 (s, 1H) 4.14-4.28 (m, 1H) 6.98-7.10 (m, 1H) 7.30 (d, J=1.25 Hz, 1H) 7.34 (d, J=8.28 Hz, 1H).

Example 226

N-(4-(3,4-dichlorophenyl)butan-2-yl)-1-ethyl-4-hydroxy-5-oxo-2,5-dihydro-1H-pyrrole-3-carboxamide

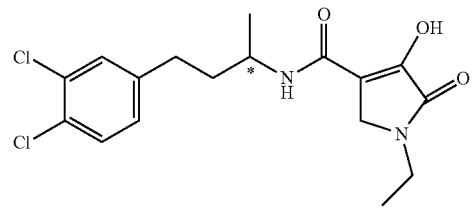 [SMILES: CCN1CC(C(=O)NC(C)CCc2ccc(Cl)c(Cl)c2)=C(O)C1=O]

Example 226A

N-(4-(3,4-dichlorophenyl)butan-2-yl)-1-ethyl-4-methoxy-5-oxo-2,5-dihydro-1H-pyrrole-3-carboxamide

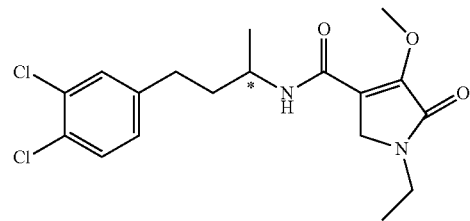 [SMILES: CCN1CC(C(=O)NC(C)CCc2ccc(Cl)c(Cl)c2)=C(OC)C1=O]

To a solution of Intermediate 16 (2.41 g, 8.27 mmol) and 1-ethyl-4-methoxy-5-oxo-2,5-dihydro-1H-pyrrole-3-carboxylic acid (1.84 g, 9.92 mmol) in DCM (25 mL) was added EDC (3.96 g, 20.7 mmol), HOBT (3.17 g, 20.7 mmol) and N-methylmorpholine (3.64 mL, 33.1 mmol). The reaction mixture was stirred at rt for 18 h, diluted with DCM, washed by brine, dried over MgSO₄, filtered and concentrated. The residue was purified by ISCO chromatography (EtOAc-IPA (10-1)/Hexanes 0-100% over 30 min, column 220 g, flow rate 100 mL/min) to give Example 226A (3.39 g, 8.80 mmol, 100% yield). HPLC/MS (Method D) RT=1.09 min, [M+1]⁺ 385.1.

Example 226

At 0° C. to s solution of Example 226A (675 mg, 1.75 mmol) in DCM (10 mL) was added boron tribromide-methyl sulfide complex (5.26 mL, 1.00 M, 5.26 mmol) slowly. The reaction mixture was stirred at rt for 1 h, quenched by adding MeOH and was stirred at rt for 30 min. The reaction mixture was concentrated down, taken into DCM, washed with brine, dried over MgSO4, filtered and concentrated. The residue was purified by RP Prep-HPLC (Method S) to obtain Example 226 (389 mg, 1.05 mmol, 60.0% yield) as an off white solid. HPLC/MS (Method D) RT=0.99 min, [M+1]⁺ 371.2; ¹H NMR (400 MHz, CHLOROFORM-d) δ ppm 1.23-1.30 (6H, m), 1.75-1.89 (2H, m), 2.58-2.71 (2H, m), 3.58 (2H, q, J=7.2 Hz), 4.05 (2H, d, J=1.5 Hz), 4.17 (1H, dd, J=8.5, 6.8 Hz), 6.55 (1H, br. s.), 7.03 (1H, dd, J=8.0, 2.0 Hz), 7.28 (1H, d, J=2.0 Hz), 7.32 (1H, d, J=8.0 Hz).

Example 227

N-(1-(3,4-dichlorophenyl)pentan-3-yl)-4-hydroxy-1-methyl-5-oxo-2,5-dihydro-1H-pyrrole-3-carboxamide (from (R)-2-methylpropane-2-sulfinamide)

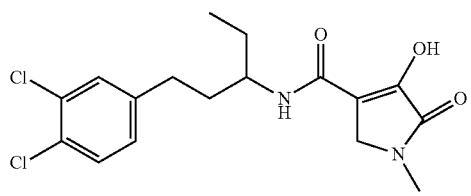 [SMILES: CCC(CCc1ccc(Cl)c(Cl)c1)NC(=O)C1=C(O)C(=O)N(C)C1]

Example 227A 1-(3,4-dichlorophenyl)pentan-3-amine hydrochloride (from (R)-2-methylpropane-2-sulfinamide)

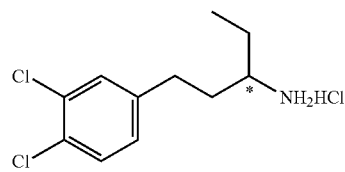

By appropriate application of methods described for Intermediate 16, 3-(3,4-dichlorophenyl)propanal (97 mg, 0.47 mmol), (R)-2-methylpropane-2-sulfinamide (69 mg, 0.57 mmol) and ethylmagnesium bromide in ether (0.163 mL, 3.00 M, 0.490 mmol) were converted to 1-(3,4-dichlorophenyl)pentan-3-amine hydrochloride (from (R)-2-methylpropane-2-sulfinamide) (73 mg, 0.27 mmol, 56%). HPLC/MS (Method D) RT=0.78 min, [M+1]⁺ 234.0.

Example 227

By appropriate application of methods described for Example 226, Example 227A (36 mg, 0.12 mmol) and 4-methoxy-1-methyl-5-oxo-2,5-dihydro-1H-pyrrole-3-carboxylic acid (30 mg, 0.18 mmol) were converted to Example 227 (27 mg, 0.73 mmol, 62%) as a white solid. HPLC/MS (Method D) RT=0.99 min, [M+1]⁺ 371.2; ¹H NMR (400 MHz, CHLOROFORM-d) δ ppm 0.95 (t, J=7.40 Hz, 3H) 1.51 (ddd, J=14.24, 7.40, 7.22 Hz, 1H) 1.58-1.69 (m, 1H) 1.69-1.81 (m, 1H) 1.81-1.98 (m, 1H) 2.64 (t, J=7.91 Hz, 2H) 3.15 (s, 3H) 4.03 (ddd, J=8.60, 4.77, 4.45 Hz, 1H) 4.08 (s, 2H) 6.66 (d, J=9.03 Hz, 1H) 7.03 (dd, J=8.28, 2.01 Hz, 1H) 7.27 (d, J=1.76 Hz, 1H) 7.32 (d, J=8.03 Hz, 1H).

By appropriate application of the methods described for Example 226 or Example 227, Examples 232, 233, 236 and 237 were synthesized.

Example 239

N-(5-(3,4-dichlorophenyl)pentan-2-yl)-1-ethyl-4-hydroxy-5-oxo-2,5-dihydro-1H-pyrrole-3-carboxamide (Enantiomer A)

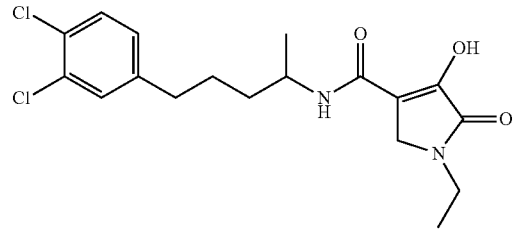 [SMILES: CCN1CC(C(=O)NC(C)CCCc2ccc(Cl)c(Cl)c2)=C(O)C1=O]

Example 239A

N-(5-(3,4-dichlorophenyl)pentan-2-yl)-1-ethyl-4-methoxy-5-oxo-2,5-dihydro-1H-pyrrole-3-carboxamide (Isomer A)

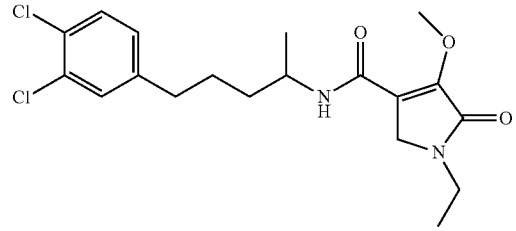 [SMILES: CCN1CC(C(=O)NC(C)CCCc2ccc(Cl)c(Cl)c2)=C(OC)C1=O]

To the mixture of Intermediate 18 (5-(3,4-Dichlorophenyl)pentan-2-amine hydrobromide) (46 mg, 0.15 mmol), 1-ethyl-4-methoxy-5-oxo-2,5-dihydro-1H-pyrrole-3-carboxylic acid (30 mg, 0.16 mmol) and PyBOP® (84. mg, 0.16 mmol) in DMF (1 mL) and DCM (0.5 mL) was added diisopropylethylamine (77 μL, 0.44 mmol) and the reaction was stirred at rt for 18 h. The reaction mixture was concentrated and the residue was purified by ISCO chromatography (4 g cartridge, 0 to 100% ethyl acetate/hexane) to afford Example 239A (42 mg, 72%) as an oil. HPLC/MS (Method L) RT=2.22 min, [M+1]⁺ 399.0.

Example 239

The solution of Example 239A (42 mg, 0.11 mmol) in DCM (1 mL) was treated with boron trichloride (316 µL, 0.320 mmol) at rt. After 12 h, methanol was added to the reaction mixture, stirred for 10 min and concentrated. The residue was dissolved in methanol and purified by reverse phase preparative HPLC (Method S) to give Example 239 (18 mg, 44%) as a white powder. HPLC/MS (Method L) RT=2.15 min, [M+1]$^+$ 385.0; $^1$H NMR (400 MHz, MeOD) δ ppm 1.18-1.26 (6H, m), 1.52-1.61 (2H, m), 1.62-1.77 (2H, m), 2.64 (2H, q, J=7.9 Hz), 3.54 (2H, q, J=7.3 Hz), 4.03 (2H, s), 4.05-4.15 (1H, m), 7.13 (1H, dd, J=8.2, 1.9 Hz), 7.36 (1H, d, J=2.0 Hz), 7.40 (1H, d, J=8.3 Hz).

Example 240

N-(5-(3,4-dichlorophenyl)pentan-2-yl)-1-ethyl-4-hydroxy-5-oxo-2,5-dihydro-1H-pyrrole-3-carboxamide (Enantiomer B)

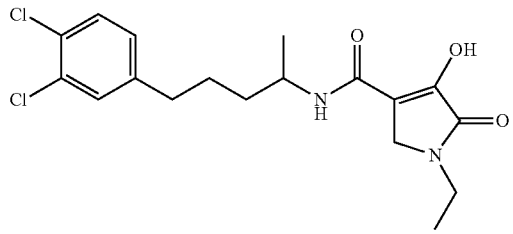 [SMILES: CCN1CC(C(=O)NC(C)CCCc2ccc(Cl)c(Cl)c2)=C(O)C1=O]

By appropriate application of method described for Example 239, Intermediate 19, 5-(3,4-Dichlorophenyl)pentan-2-amine hydrobromide (Enantiomer B) (40 mg, 0.17 mmol) was converted to Example 240 (15 mg, 56%) as a white powder. HPLC/MS (Method L) RT=2.15 min, [M+1]$^+$=385.0; $^1$H NMR (400 MHz, MeOD) δ ppm 1.20-1.27 (6H, m), 1.54-1.63 (2H, m), 1.63-1.78 (2H, m), 2.58-2.73 (2H, m), 3.55 (2H, q, J=7.3 Hz), 4.04 (2H, s), 4.06-4.17 (1H, m), 7.15 (1H, dd, J=8.3, 2.0 Hz), 7.38 (1H, d, J=2.0 Hz), 7.42 (1H, d, J=8.3 Hz).

Example 241 tert-butyl 2-(2-(2-(4-(4-chlorophenethylcarbamoyl)-3-hydroxy-2-oxo-2,5-dihydro-1H-pyrrol-1-yl)ethoxy)ethoxy)ethylcarbamate

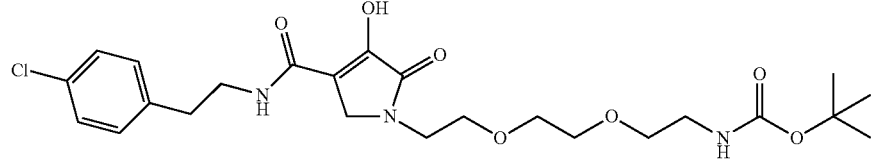 [SMILES: CC(C)(C)OC(=O)NCCOCCOCCN1CC(C(=O)NCCc2ccc(Cl)cc2)=C(O)C1=O]

Example 241A

N-(4-chlorophenethyl)-2-(2,2-dimethyl-5-oxo-1,3-dioxolan-4-ylidene)acetamide

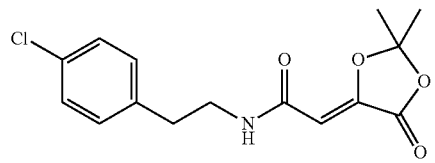 [SMILES: CC1(C)OC(=O)/C(=C/C(=O)NCCc2ccc(Cl)cc2)O1]

By appropriate application of method described in Intermediate 7, 2-(4-chlorophenyl)ethylamine (0.27 mL, 1.9 mmol) and 2-(2,2-dimethyl-5-oxo-1,3-dioxolan-4-ylidene)acetic acid (365 mg, 2.12 mmol) were converted to Example 241A (190 mg, 32%) as a white solid. HPLC/MS (Method L) RT=1.78 min, [M+1]$^+$ 310.0.

Example 241

By appropriate application of method described in Example 167, tert-butyl 2-(2-(2-aminoethoxy)ethoxy)ethylcarbamate (52 mg, 0.21 mmol) and Example 241A were converted to Example 241 (57 mg, 53%) as a white solid. HPLC/MS (Method L) RT=2.04 min, [M+1]$^+$ 512.1; $^1$H NMR (400 MHz, MeOD) δ ppm 1.44 (9H, s), 2.87 (2H, m), 3.22 (2H, m), 3.50 (2H, m), 3.56-3.63 (6H, m), 3.64-3.73 (6H, m), 7.21-7.39 (4H, m).

Example 242 tert-butyl 3-(2-(2-(2-(4-(4-chlorophenethylcarbamoyl)-3-hydroxy-2-oxo-2,5-dihydro-1H-pyrrol-1-yl)ethoxy)ethoxy)ethylamino)-3-oxopropylcarbamate

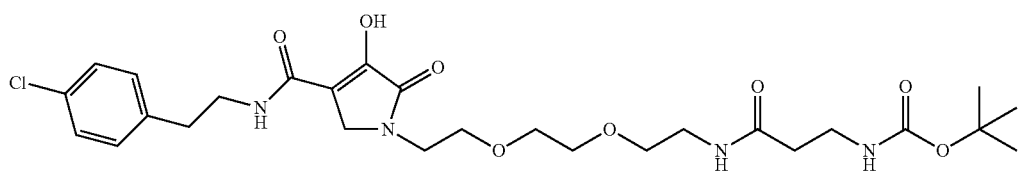 [SMILES: CC(C)(C)OC(=O)NCCC(=O)NCCOCCOCCN1CC(C(=O)NCCc2ccc(Cl)cc2)=C(O)C1=O]

Example 242A 1-(2-(2-(2-aminoethoxy)ethoxy)ethyl)-N-(4-chlorophenethyl)-4-hydroxy-5-oxo-2,5-dihydro-1H-pyrrole-3-carboxamide

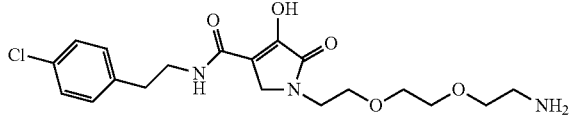 [SMILES: NCCOCCOCCN1CC(C(=O)NCCc2ccc(Cl)cc2)=C(O)C1=O]

To a solution of tert-butyl 2-(2-(2-(4-(4-chlorophenethylcarbamoyl)-3-hydroxy-2-oxo-2,5-dihydro-1H-pyrrol-1-yl)ethoxy)ethoxy)ethylcarbamate (45 mg, 0.090 mmol) in DCM (1 mL) was added trifluoroacetic acid (1 mL) and the reaction mixture was stirred at rt for 30 min. The reaction mixture was concentrated in vacuo. The crude hydrochloride salt was loaded onto an SCX cartridge in methanol. The cartridge was washed with several volumes of methanol which was discarded. A solution of ammonia in MeOH was flushed through the cartridge and the collected solution was concentrated to give Example 242A (35 mg, 97%) as a clear oil. HPLC/MS (Method L) RT=1.52 min, [M+1]$^+$ 412.2.

Example 242

To a solution of Example 242A (22 mg, 0.050 mmol), 3-(tert-butoxycarbonylamino)propanoic acid (10 mg, 0.050 mmol), and PyBOP® (31 mg, 0.060 mmol) in DMF (1 mL) and DCM (0.5 mL) was added diisopropylethylamine (28 μL, 0.16 mmol) and the reaction mixture was stirred at rt for 4 h. The reaction mixture was concentrated and the residue was dissolved in methanol and purified by reverse phase preparative HPLC (method T) to afford Example 242 (15 mg, 48%) as a clear oil. HPLC/MS (Method L) RT=2.02 min, [M+1]$^+$ 583.3; $^1$H NMR (400 MHz, MeOD) δ ppm 1.25 (9H, s), 2.20 (2H, t, J=6.8 Hz), 2.69 (2H, t, J=7.2 Hz), 3.12-3.16 (6H, m), 3.34 (2H, t, J=5.5 Hz), 3.39-3.53 (10H, m), 3.94-3.97 (2H, m), 7.04-7.15 (4H, m).

By appropriate application of the methods described for Example 242, Example 243 was synthesized.

Example 244 methyl 5-(3,4-dichlorophenyl)-2-(4-hydroxy-1-methyl-5-oxo-2,5-dihydro-1H-pyrrole-3-carboxamido)pentanoate

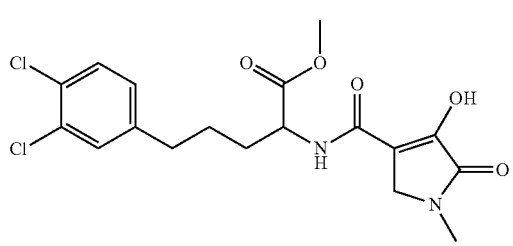 [SMILES: COC(=O)C(CCCc1ccc(Cl)c(Cl)c1)NC(=O)C1=C(O)C(=O)N(C)C1]

Example 244A

N-(1-cyano-4-(3,4-dichlorophenyl)butyl)-4-methoxy-1-methyl-5-oxo-2,5-dihydro-1H-pyrrole-3-carboxamide

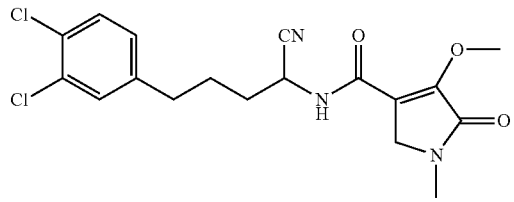 [SMILES: COC1=C(C(=O)NC(C#N)CCCc2ccc(Cl)c(Cl)c2)CN(C)C1=O]

Intermediate 20 (100 mg, 0.410 mmol), 4-methoxy-1-methyl-5-oxo-2,5-dihydro-1H-pyrrole-3-carboxylic acid (77 mg, 0.45 mmol) and PyBOP® (235 mg, 0.450 mmol) were combined in DMF (2 mL) and DCM (1 mL) at rt and treated with diisopropylethylamine (216 μL, 1.23 mmol). The reaction mixture was stirred at rt for 2 h and concentrated. The residue was purified by ISCO chromatography (EtOAc/Hexanes 0-100%, column 4 g) to afford Example 244A (45 mg, 28%) as a clear oil. HPLC/MS (Method L) RT=2.02 min, [M+1]$^+$ 396.1.

Example 244

To a solution of Example 244A (41 mg, 0.10 mmol) in DCM (1 mL) was added Boron trichloride (0.31 mL, 0.31 mmol) and the reaction mixture was stirred at rt for 18 h. The reaction was quenched with a few drops of methanol and concentrated. The residue was dissolved in methanol and purified by reverse phase preparative HPLC (method T) to afford Example 244 (15 mg, 35%) as a clear oil. HPLC/MS (Method L) RT=2.00 min, [M+1]$^+$ 415.1. $^1$H NMR (400 MHz, MeOD) δ ppm 1.51-1.85 (4H, m), 2.52 (2H, m), 2.94 (3H, s), 3.61 (3H, s), 3.86 (2H, m), 4.49 (1H, m), 6.99 (1H, dd, J=8.3, 2.3 Hz), 7.22 (1H, d, J=2.0 Hz), 7.27 (1H, d, J=8.0 Hz).

Example 245

N-(3-(3,4-dichlorophenyl)propyl)-4-hydroxy-1-(2-hydroxyethyl)-5-oxo-2,5-dihydro-1H-pyrrole-3-carboxamide

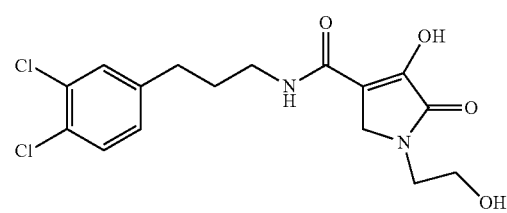 [SMILES: O=C(NCCCc1ccc(Cl)c(Cl)c1)C1=C(O)C(=O)N(CCO)C1]

To a solution of 2-aminoethanol (10 μL, 0.17 mmol) and paraformaldehyde (5.0 mg, 0.17 mmol) in methanol (3 mL) was added diisopropylethylamine (32 μL, 0.18 mmol) and the reaction mixture was subject to microwave irradiation at 60° C. for 10 min. To the resulting solution was added N-(3-(3,4-dichlorophenyl)propyl)-2-(2,2-dimethyl-5-oxo-1,3-dioxolan-4-ylidene)acetamide (60 mg, 0.17 mmol) and the reaction mixture was subject to microwave irradiation at 100° C.

for 15 min. After cooling to rt, the reaction was concentrated and the residue was purified by preparative HPLC (method T) to afford Example 245 (32 mg, 51%) as a white solid. HPLC/MS (Method L) RT=1.81 min, [M+1]+ 373.1 ¹H NMR (400 MHz, MeOD) δ ppm 1.85-1.99 (2H, m), 2.63-2.73 (2H, m), 3.30-3.43 (4H, m), 3.56-3.64 (2H, m), 3.71-3.80 (2H, m), 7.17 (1H, d, J=8.0 Hz), 7.37-7.45 (2H, m).

Example 246

1-(2-azidoethyl)-N-(3-(3,4-dichlorophenyl)propyl)-4-hydroxy-5-oxo-2,5-dihydro-1H-pyrrole-3-carboxamide

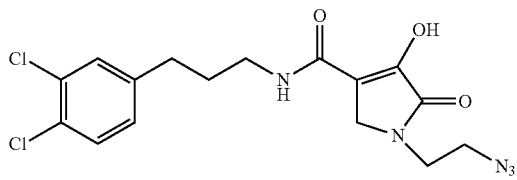 [SMILES: [N-]=[N+]=NCCN1CC(C(=O)NCCCc2ccc(Cl)c(Cl)c2)=C(O)C1=O]

Example 246A 1-(2-bromoethyl)-N-(3-(3,4-dichlorophenyl)propyl)-4-hydroxy-5-oxo-2,5-dihydro-1H-pyrrole-3-carboxamide

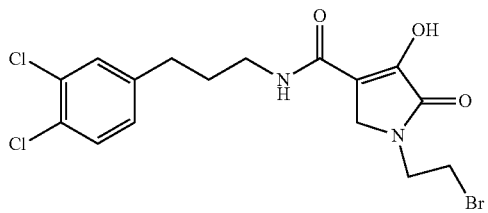 [SMILES: O=C(NCCCc1ccc(Cl)c(Cl)c1)C1=C(O)C(=O)N(CCBr)C1]

At 0° C. to a solution of Example 245 (70 mg, 0.19 mmol) in DCM (4 mL) was added phosphorus tribromide (21 µL, 0.21 mmol) drop wise. After stirring at 0° C. for 30 min, the reaction mixture was treated with saturated sodium bicarbonate and diluted with DCM. The layers were separated and the organic layer washed with water twice, brine twice, dried over Na₂SO₄, filtered and concentrated. The crude was purified on ISCO chromatography (ethyl acetate/hexane 0-100%) to afford Example 246A (16 mg, 20%) as an clear oil. HPLC/MS (Method L) RT=2.07 min, [M+1]+ 437.0.

Example 246

The solution of Example 246A (16 mg, 0.040 mmol) and sodium azide (7.2 mg, 0.11 mmol) in DMF (0.7 mL) was heated at 60° C. for 3 h. The reaction mixture was allowed to rt, diluted with ethyl acetate and washed with brine twice, dried over MgSO₄, filtered and concentrated. The residue was purified by reverse phase preparative HPLC (Method T) to give Example 246 (9.0 mg, 62%) as a white powder. HPLC/MS (Method L) RT=1.99 min, [M+1]+ 398.1. ¹H NMR (400 MHz, MeOD) δ ppm 1.85-1.97 (2H, m), 2.69 (2H, t, J=7.7 Hz), 3.39 (3H, J=6.9 Hz), 3.58 (2H, t, J=5.6 Hz), 3.68 (2H, t, J=5.6 Hz), 4.09 (2H, s), 7.18 (1H, dd, J=8.3, 2.0 Hz), 7.35-7.48 (2H, m).

Example 247

4-hydroxy-1-methyl-N-(3-(2-methylbenzo[d]thiazol-5-yl)prop-2-ynyl)-5-oxo-2,5-dihydro-1H-pyrrole-3-carboxamide

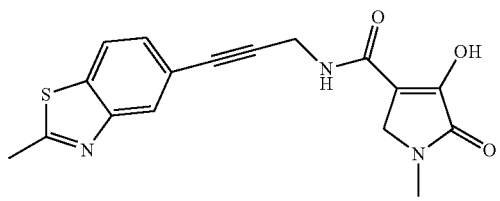 [SMILES: Cc1nc2cc(C#CCNC(=O)C3=C(O)C(=O)N(C)C3)ccc2s1]

5-Bromo-2-methylbenzo[d]thiazole (82 mg, 0.36 mmol), Intermediate 21 (50 mg, 0.24 mmol), copper (I) iodide (9 mg, 0.05 mmol), triphenylphosphine (13 mg, 0.050 mmol) and bis(triphenylphosphine)palladium chloride (17 mg, 0.020 mmol) were combined in a microwave tube and sealed. The system was back filled with nitrogen and evacuated with vacuum three times. The reaction mixture was charged with DMF (1.0 mL) and diethylamine (1.0 mL) and heated via microwave for 20 min at 120° C. After cooling to rt, the solvents were evaporated and the residue was purified by reverse phase preparative HPLC (Method T) to afford Example 247 (31 mg, 38%) as a clear oil. HPLC/MS (Method L) RT=1.61 min, [M+1]+ 342.1; ¹H NMR (400 MHz, MeOD) δ ppm 2.75 (3H, s), 2.98 (3H, s), 3.88-4.03 (2H, m), 4.28 (2H, m), 7.36 (1H, dd, J=8.4, 1.1 Hz), 7.80 (1H, d, J=8.5 Hz), 7.83 (1H, s).

Example 248

4-hydroxy-1-methyl-N-(3-(4-methyl-3-(trifluoromethyl)phenyl)prop-2-ynyl)-5-oxo-2,5-dihydro-1H-pyrrole-3-carboxamide

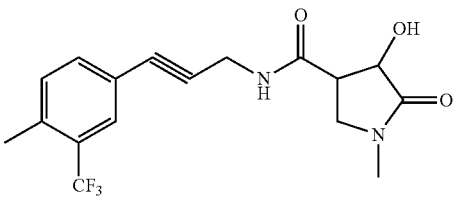 [SMILES: Cc1ccc(C#CCNC(=O)C2CN(C)C(=O)C2O)cc1C(F)(F)F]

By appropriate application of the methods described for Example 247, Example 248 was synthesized. HPLC/MS (Method L) RT=1.93 min, [M+1]+ 353.1.

Example 249

4-hydroxy-1-methyl-N-(3-(2-methylbenzo[d]thiazol-5-yl)propyl)-5-oxo-2,5-dihydro-1H-pyrrole-3-carboxamide

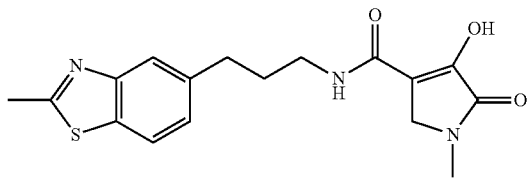 [SMILES: Cc1nc2cc(CCCNC(=O)C3=C(O)C(=O)N(C)C3)ccc2s1]

The solution of Example 247 (23 mg, 0.070 mmol) in methanol (10 mL) was subject to hydrogenation at rt under 1 atmosphere for 15 min using Pd/C as catalyst. The reaction mixture was filtered, concentrated and the residue was purified by reverse phase preparative HPLC (Method T) to afford Example 249 (0.9 mg, 4%) as a clear oil. HPLC/MS (Method L) RT=1.59 min, [M+1]$^+$ 346.2; $^1$H NMR (400 MHz, MeOD) δ ppm 2.01 (m, 2H), 2.84 (3H, s), 2.84-2.90 (2H, m), 3.07 (3H, s), 3.42 (2H, t, J=6.8 Hz), 3.94 (2H, m), 7.32 (1H, dd, J=8.3, 1.5 Hz), 7.75 (1H, s), 7.84 (1H, d, J=8.3 Hz).

By appropriate application of the methods described for Example 249, Examples 253, 259 and 263 were synthesized.

Example 266

N-(3-(3,4-dichlorophenyl)propyl)-2-hydroxy-3-oxo-3,5,6,7,8,8a-hexahydroindolizine-1-carboxamide

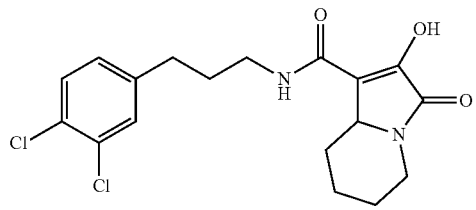 [SMILES: O=C(NCCCc1ccc(Cl)c(Cl)c1)C1=C(O)C(=O)N2CCCCC12]

Example 266A

N-(3-(3,4-dichlorophenyl)propyl)-2-methoxy-3-oxo-3,5,6,7,8,8a-hexahydroindolizine-1-carboxamide

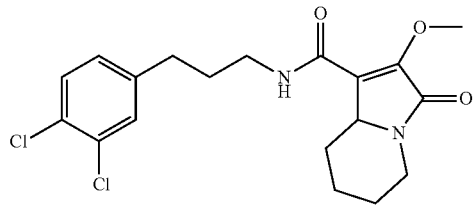 [SMILES: COC1=C(C(=O)NCCCc2ccc(Cl)c(Cl)c2)C2CCCCN2C1=O]

To a mixture of 3-(3,4-dichlorophenyl)propan-1-amine (57 mg, 0.24 mmol), Intermediate 22 (50 mg, 0.24 mmol) and PyBOP (136 mg, 0.260 mmol) in DMF (1.0 mL) was added diisopropylethylamine (12 μL, 0.71 mmol). The reaction was stirred at rt for 18 h. The reaction mixture was concentrated to remove most of the solvents and purified on ISCO (4 g cartridge, 0 to 100% ethyl acetate/hexane) to afford Example 266A (12 mg, 13%) as an oil. LC/MS (HPLC Method L): RT=2.07 min, [M+1]$^+$ 397.0.

Example 266

To a solution of Example 266A (12 mg, 0.030 mmol) in DCM (0.8 mL) was added boron trichloride (91 μL, 0.090 mmol) at rt and the reaction mixture was stirred at rt for 12 h. MeOH was added to quenched the reaction and the mixture was stirred for 10 min, concentrated and the residue was purified by reverse phase preparative HPLC (Method L) to give Example 266 (3 mg, 26%) as a clear oil. HPLC/MS (Method L) RT=2.04 min, [M+1]$^+$ 383.0; $^1$H NMR (400 MHz, MeOD) δ ppm 1.45-1.56 (6H, m), 1.75-1.88 (1H, m), 2.68-2.77 (1H, m), 2.87 (2H, m), 3.11-3.22 (1H, m), 4.14-4.21 (1H, m), 4.36-4.45 (1H, m), 7.35 (1H, dd, J=8.3, 2.0 Hz), 7.57-7.62 (2H, m).

Examples 267-268

N-(4-(3,4-dichlorophenyl)butan-2-yl)-2-hydroxy-3-oxo-3,5,6,7,8,8a-hexahydroindolizine-1-carboxamide (Enantiomer A) and N-(4-(3,4-dichlorophenyl)butan-2-yl)-2-hydroxy-3-oxo-3,5,6,7,8,8a-hexahydroindolizine-1-carboxamide (Enantiomer B)

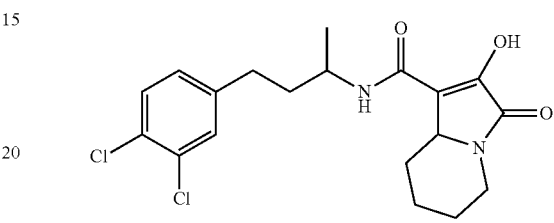

Example 267A and 268A

N-(4-(3,4-dichlorophenyl)butan-2-yl)-2-methoxy-3-oxo-3,5,6,7,8,8a-hexahydroindolizine-1-carboxamide (Enantiomer A) and N-(4-(3,4-dichlorophenyl)butan-2-yl)-2-methoxy-3-oxo-3,5,6,7,8,8a-hexahydroindolizine-1-carboxamide (Enantiomer B)

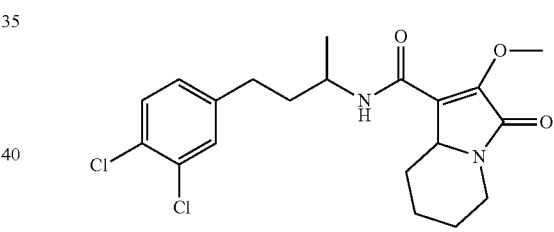

By appropriate application of method described in Example 266, 4-(3,4-dichlorophenyl)butan-2-amine (56.8 mg, 0.260 mmol) and 2-methoxy-3-oxo-3,5,6,7,8,8a-hexahydroindolizine-1-carboxylic acid (55 mg, 0.260 mmol) were converted to racemate N-(4-(3,4-dichlorophenyl)butan-2-yl)-2-methoxy-3-oxo-3,5,6,7,8,8a-hexahydroindolizine-1-carboxamide (30 mg, 28%). HPLC/MS (Method L) RT=2.147 min, [M+1]$^+$ 411.0. This racemate was separated on chiral PerpHPLC (chiral AD 10 micron 4.6×250 mm, 15 min 15% isocratic. A=Isopropyl alcohol. B=Heptane) to afford Enantiomer A: (10 mg, 10%) at RT of 11.08 min and Enantiomer B (13 mg, 12%) at RT of 13.38 min. Enantiomer A: HPLC/MS (Method L) RT=2.120 min, [M+1]$^+$ 411.0; Enantiomer B: HPLC/MS (Method L) RT=2.133 min, [M+1]$^+$ 411.0.

Example 267 and Example 268

Example 267A and Example 268A were converted to Example 267 and Example 268 by appropriate application of method described in Example 266. Enantiomer A: HPLC/MS (Method L) RT=2.103 min, [M+1]+ 397.0; Enantiomer B: HPLC/MS (Method L) RT=2.102 min, [M+1]+ 397.0.

Example 269

N-(4-(3,4-dichlorophenyl)butan-2-yl)-1-(2-(4-fluorobenzylamino)-2-oxoethyl)-4-hydroxy-5-oxo-2,5-dihydro-1H-pyrrole-3-carboxamide

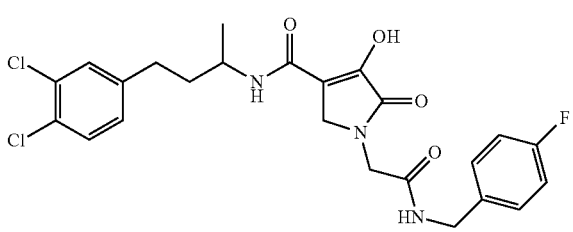 [SMILES: CC(CCc1ccc(Cl)c(Cl)c1)NC(=O)C1=C(O)C(=O)N(CC(=O)NCc2ccc(F)cc2)C1]

Example 269A 2-(4-(4-(3,4-dichlorophenyl)butan-2-ylcarbamoyl)-3-hydroxy-2-oxo-2,5-dihydro-1H-pyrrol-1-yl)acetic acid

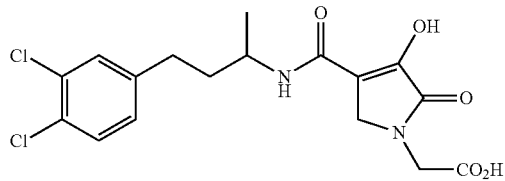 [SMILES: CC(CCc1ccc(Cl)c(Cl)c1)NC(=O)C1=C(O)C(=O)N(CC(=O)O)C1]

By appropriate application of method described for Example 167, 2-aminoacetic acid (18 mg, 0.24 mmol) and (Z)—N-(4-(3,4-dichlorophenyl)butan-2-yl)-2-(2,2-dimethyl-5-oxo-1,3-dioxolan-4-ylidene)acetamide (60 mg, 0.16 mmol) were converted to Example 269A (21 mg, 0.052 mmol, 33%). HPLC/MS (Method L) RT=1.90 min, [M+1]+ 401.0.

Example 269

To a solution of Example 269A (21 mg, 0.052 mmol), (4-fluorophenyl)methanamine (10 µL, 0.088 mmol) and PyBOP (27 mg, 0.052 mmol) in DCM (2 mL) was added DIEA (27 µL, 0.16 mmol) and the reaction mixture was stirred at rt for 18 h. The reaction mixture was diluted with EtOAc, washed with water and brine, dried over MgSO4, filtered and concentrated. The residue was purified by reverse phase preparative HPLC (Method U) to give Example 269 (3.1 mg, 5.8 µmol, 11% yield) as a white solid. HPLC/MS (Method L) RT=2.09 min, [M+1]+ 508.0.

Example 270

(E)-N-(4-(3,4-dichlorophenyl)butan-2-yl)-4-hydroxy-5-oxo-1-(3-(4-(trifluoromethoxy)phenyl)allyl)-2,5-dihydro-1H-pyrrole-3-carboxamide

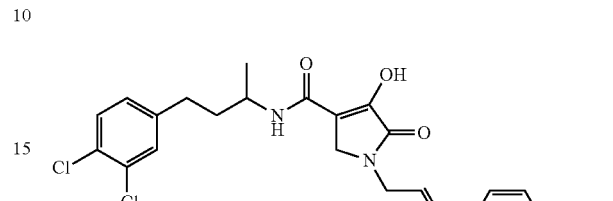

Example 270A

N-(4-(3,4-dichlorophenyl)butan-2-yl)-2-(2,2-dimethyl-5-oxo-1,3-dioxolan-4-ylidene)acetamide

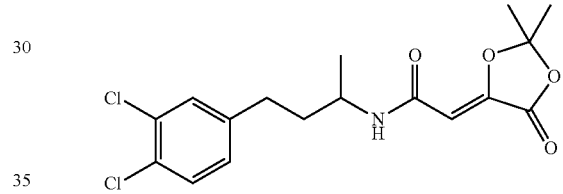

The mixture of 4-(3,4-Dichlorophenyl)butan-2-amine (1.0 g, 4.6 mmol), 2-(2,2-dimethyl-5-oxo-1,3-dioxolan-4-ylidene)acetic acid (0.79 g, 4.6 mmol) and PyBOP® (2.62 g, 5.04 mmol) in DMF (10 mL) was treated with diisopropylethylamine (2.40 mL, 13.8 mmol) and the reaction mixture was stirred at rt for 2 h. The reaction mixture was concentrated and purified by ISCO chromatography (12 g cartridge, 0 to 100% ethyl acetate/hexanes) to afford Example 270A (1.4 g, 82%) as a white solid. LC/MS (HPLC Method L): RT=2.08 min, [M+1]+ 372.0.

Example 270B

N-(4-(3,4-dichlorophenyl)butan-2-yl)-4-methoxy-5-oxo-1-(prop-2-ynyl)-2,5-dihydro-1H-pyrrole-3-carboxamide

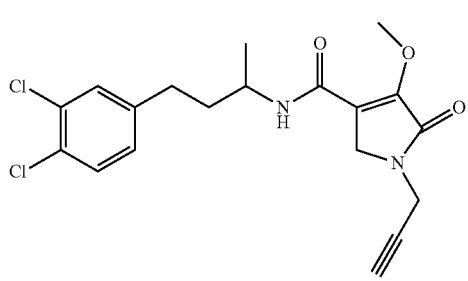 [SMILES: C#CCN1CC(C(=O)NC(C)CCc2ccc(Cl)c(Cl)c2)=C(OC)C1=O]

The reaction mixture of Prop-2-yn-1-amine (77.0 mg, 1.40 mmol), paraformaldehyde (42.0 mg, 1.40 mmol) and diisopropylethylamine (0.27 mL, 1.5 mmol) in methanol (14 mL) was subject to microwave irradiation at 60° C. for 10 min. To the cooled mixture, Example 270A (0.52 g, 1.4 mmol) was added and the reaction mixture was subject to microwave irradiation at 100° C. for 15 min. Solvent was removed and the residue was dissolved in methanol (1.5 mL) and acetonitrile (13.5 mL). At 0° C. to the reaction mixture was added (diazomethyl)trimethylsilane (1.1 mL, 2.1 mmol) and the mixture was stirred at rt for 18 h, concentrated and the residue was purified by ISCO chromatography (40 g cartridge, 0 to 10% methanol/methylene chloride) to afford Example 270B (0.47 g, 85%) as light brown oil. LC/MS (HPLC Method L): RT=2.10 min, [M+1]$^+$ 395.0.

Example 270C

N-(4-(3,4-dichlorophenyl)butan-2-yl)-4-hydroxy-5-oxo-1-(3-(4-(trifluoromethoxy)phenyl)prop-2-ynyl)-2,5-dihydro-1H-pyrrole-3-carboxamide

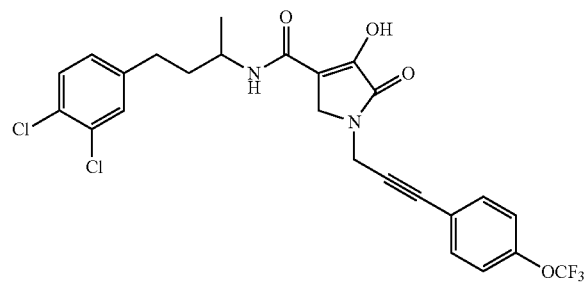 [SMILES: CC(CCc1ccc(Cl)c(Cl)c1)NC(=O)C1=C(O)C(=O)N(CC#Cc2ccc(OC(F)(F)F)cc2)C1]

The mixture of 1-Bromo-4-(trifluoromethoxy)benzene (37 mg, 0.15 mmol), Example 270B (60 mg, 0.15 mmol), (copper (I) iodide (6 mg, 0.03 mmol), triphenylphosphine (8 mg, 0.03 mmol) and bis(triphenylphosphine)palladium chloride (11 mg, 0.015 mmol) in dimethylformamide (1.0 mL) and diethylamine (1.0 mL) was filled with nitrogen and evacuated with vacuum three times. The reaction mixture was subject to microwave irradiation at 120° C. for 20 min. After cooling to rt, the solvents were evaporated to afford a dark brown residue which was dissolved in methanol and purified by reverse phase preparative HPLC (Method U) to afford Example 270C (15 mg, 18%) as a clear oil. LC/MS (HPLC Method L): RT=2.38 min, [M+1]$^+$ 541.0.

Example 270

The mixture of Example 270C (15 mg, 0.030 mmol) in methanol (10 mL) was loaded on to H-cube hydrogenator and recycled 15 min using a palladium on charcoal cartridge. The solution was collected and concentrated and was purified by reverse phase preparative HPLC (Method U) to afford Example 270 (2.0 mg, 13%) as a clear oil. LC/MS (HPLC Method L): RT=2.34 min, [M+1]$^+$ 543.0. $^1$H NMR (400 MHz, MeOD) δ ppm 7.23-7.34 (4H, m), 7.19 (1H, s), 7.17 (1H, s), 7.03 (1H, dd, J=8.3, 2.0 Hz), 6.62 (1H, d, J=11.5 Hz), 5.60-5.71 (1H, m), 4.25-4.31 (2H, m), 3.90-4.00 (1H, m), 3.78-3.84 (2H, m), 2.53-2.61 (2H, m), 1.69-1.79 (2H, m), 1.11 (3H, d, J=6.53 Hz).

Example 271

N-(4-(3,4-dichlorophenyl)butan-2-yl)-4-hydroxy-5-oxo-1-(3-(4-(trifluoromethoxy)phenyl)propyl)-2,5-dihydro-1H-pyrrole-3-carboxamide

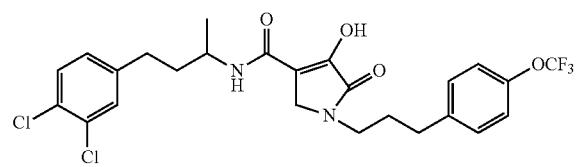 [SMILES: CC(CCc1ccc(Cl)c(Cl)c1)NC(=O)C1=C(O)C(=O)N(CCCc2ccc(OC(F)(F)F)cc2)C1]

The mixture of Example 270C (25 mg, 0.046 mmol) and Pd/C (2 mg, 2 μmol) in MeOH (1 mL) was subject to balloon hydrogenation for 2 h. The reaction mixture was filtered over celite, concentrated and the residue was purified by reverse phase preparative HPLC (Method U) to afford Example 271 (5.2 mg, 8.6 mmol, 19% yield). LC/MS (HPLC Method L): RT=2.34 min, [M+1]$^+$ 545.0. $^1$H NMR (400 MHz, MeOD) δ ppm 7.16-7.34 (5H, m), 6.98-7.10 (2H, m), 3.89-3.99 (1H, m), 3.79-3.86 (1H, m), 3.38-3.46 (1H, m), 2.49-2.63 (4H, m), 1.65-1.95 (4H, m), 1.05-1.16 (3H, d, J=6.53 Hz). LCMS (Method L) RT=2.342 min, [M+1]$^+$ 545.0.

Example 272

1-((1H-1,2,3-triazol-4-yl)methyl)-N-(4-(3,4-dichlorophenyl)butan-2-yl)-4-hydroxy-5-oxo-2,5-dihydro-1H-pyrrole-3-carboxamide

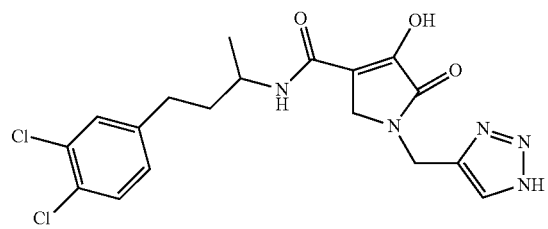 [SMILES: CC(CCc1ccc(Cl)c(Cl)c1)NC(=O)C1=C(O)C(=O)N(Cc2c[nH]nn2)C1]

The mixture of Example 270B (65 mg, 0.16 mmol), sodium azide (32 mg, 0.49 mmol) and copper(I) iodide (3.13 mg, 0.02 mmol) in DMF (1 mL) was subject to microwave irradiation at 100° C. for 25 min. After cooling to rt, the reaction was filtered over celite and concentrated. The residue was dissolved in methanol and purified by reverse phase preparative HPLC (Method U) to afford Example 272 (5 mg, 7%) as a clear oil. LC/MS (HPLC Method L): RT=1.89 min, [M+1]$^+$ 423.9. $^1$H NMR (400 MHz, MeOD) δ ppm 7.68 (1H, s), 7.19-7.31 (2H, m), 7.02 (1H, dd, J=8.3, 2.0 Hz), 4.69 (2H, s), 3.84-3.99 (3H, m), 2.51-2.61 (2H, m), 1.68-1.79 (2H, m), 1.11 (3H, d, J=6.78 Hz). LCMS (Method L) RT=1.890 min, [M+1]⁺ 424.0.

Example 273

N-(4-(3,4-dichlorophenyl)butan-2-yl)-1-(2-(3-fluoro-5-(trifluoromethyl)benzamido)ethyl)-4-hydroxy-5-oxo-2,5-dihydro-1H-pyrrole-3-carboxamide

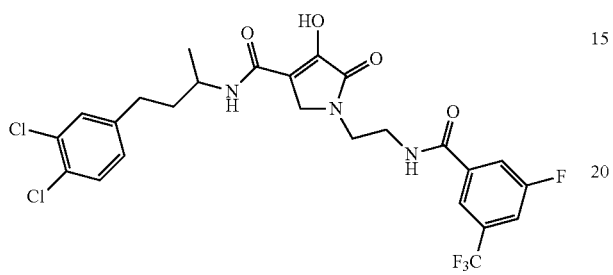

Example 273A 1-(2-aminoethyl)-N-(4-(3,4-dichlorophenyl)butan-2-yl)-4-hydroxy-5-oxo-2,5-dihydro-1H-pyrrole-3-carboxamide

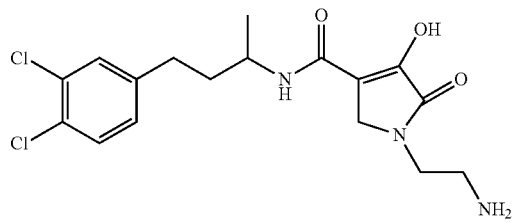 [SMILES: CC(CCc1ccc(Cl)c(Cl)c1)NC(=O)C1=C(O)C(=O)N(CCN)C1]

Example 273A was synthesized by method described in Example 167. LCMS (Method L) RT=1.7 min, [M+1]⁺ 386.

Example 273

A mixture of Example 273A (12 mg, 0.025 mmol), 3-fluoro-5-(trifluoromethyl)benzoic acid (8 mg, 0.04 mmol) and PyBOP (14 mg, 0.027 mmol) and DIPEA (0.013 mL, 0.074 mmol) in DCM (1.5 mL) was stirred at rt for 2 h. The reaction mixture was concentrated, and the residue was dissolved on MeOH and purified by reverse phase preparative HPLC (Method U) to afford Example 273 (5.0 mg, 8.0 μmol, 33% yield) as a white solid. HPLC/MS (Method L) RT=2.2 min, [M+H]⁺=576.0; ¹H NMR (400 MHz, CHLOROFORM-d) δ ppm 7.84 (1H, s), 7.68 (1H, d, J=8.53 Hz), 7.42 (1H, d, J=7.78 Hz), 7.28-7.35 (2H, m), 7.01 (1H, dd, J=8.28, 2.01 Hz), 6.16 (1H, d, J=8.53 Hz), 4.06-4.22 (3H, m), 3.77-3.85 (2H, m), 3.67-3.77 (2H, m), 2.56-2.73 (2H, m), 1.72-1.90 (2H, m), 1.23 (3H, d, J=6.53 Hz).

By appropriate application of the methods described for Example 273, Examples 274-277 were synthesized.

Example 278

1-(2-acetamidoethyl)-N-(4-(3,4-dichlorophenyl)butan-2-yl)-4-hydroxy-5-oxo-2,5-dihydro-1H-pyrrole-3-carboxamide

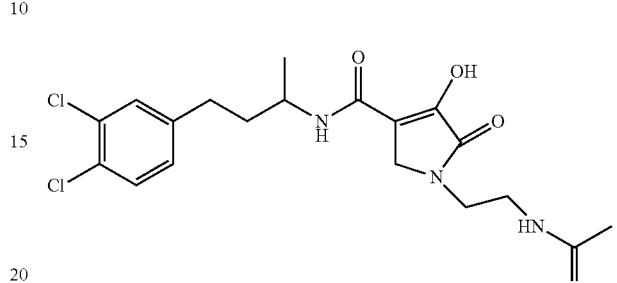

To a mixture of 1-(2-aminoethyl)-N-(4-(3,4-dichlorophenyl)butan-2-yl)-4-hydroxy-5-oxo-2,5-dihydro-1H-pyrrole-3-carboxamide (Example 273A) (38 mg, 0.087 mmol) and DIEA (30.2 μL, 0.173 mmol) in DCM (2 mL) was added acetyl chloride (8.00 μL, 0.113 mmol) and the reaction mixture was stirred at rt for 18 h. The reaction mixture was concentrated, and the residue was purified by reverse phase preparative HPLC (Method T) to give Example 278 (9.4 mg, 0.022 mmol, 25% yield). ¹H NMR (400 MHz, MeOD) δ ppm 1.95 (3H, d, J=6.53 Hz), 2.51-2.66 (5H, m), 3.38-3.46 (2H, m), 4.05 (2H, q, J=5.86 Hz), 4.24 (2H, t, J=6.02 Hz), 4.69-4.76 (1H, m), 4.78 (2H, s), 8.02 (2H, dd, J=8.16, 1.88 Hz), 8.30 (1H, d, J=2.01 Hz), 8.33 (1H, d, J=8.28 Hz), 8.75 (1H, t, J=5.77 Hz). HPLC/MS (Method L), RT=1.9 min, [M+H]⁺=427.9.

By appropriate application of the methods described for Example 278, Examples 279-280 were synthesized.

Example 281

N-(4-(3,4-dichlorophenyl)butan-2-yl)-4-hydroxy-5-oxo-1-(2-(3-(3-(trifluoromethyl)phenyl)ureido)ethyl)-2,5-dihydro-1H-pyrrole-3-carboxamide

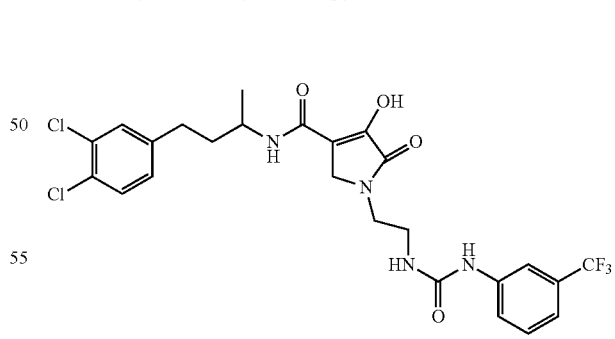

To a mixture of 1-(2-aminoethyl)-N-(4-(3,4-dichlorophenyl)butan-2-yl)-4-hydroxy-5-oxo-2,5-dihydro-1H-pyrrole-3-carboxamide (Example 273A) (33 mg, 0.075 mmol) and DIEA (26.3 μL, 0.150 mmol) in DCM (2 mL) was added 3-CF3-phenyl isocyanate (12 μL, 0.086 mmol) and the reaction mixture was stirred at rt for 18 h. The reaction mixture was concentrated, and the residue was purified by reverse phase preparative HPLC (Method T) to give Example 281 (14 mg, 0.024 mmol, 33% yield). HPLC/MS (Method L) RT=2.28 min, [M+H]$^+$=573.0; $^1$H NMR (400 MHz, CHLOROFORM-d) δ ppm 1.07-1.32 (3H, m), 1.79 (2H, d, J=7.0 Hz), 2.59 (2H, t, J=7.5 Hz), 3.54 (2H, t, J=15.2 Hz), 3.63 (2H, d, J=4.3 Hz), 3.99-4.24 (2H, m), 6.20 (1H, br, s), 6.34 (1H, br. s.), 6.97 (1H, d, J=8.0 Hz), 7.12-7.24 (2H, m), 7.24-7.35 (2H, m), 7.39 (1H, d, J=7.8 Hz), 7.58 (1H, br. s.), 8.03 (2H, br. s.).

By appropriate application of the methods described for Example 281, Examples 282 was synthesized. By appropriate application of the methods described for Example 184, Examples 283-291 were synthesized. By appropriate application of the methods described for Example 180, Examples 297-300 were synthesized. By appropriate application of the methods described for Example 167, Examples 301-307, 312, 314-317, 322, 323, 331, 332, 337, 339, 341, and 344-347 were synthesized.

Analytical data for Examples 169, 175, 200, 201, 212, 217, 219, 220, 222, 232, 233, 236, 237, 243, 253, 259, 263, 274-277, 279, 280, 282, 283-291, 297-300, 301-307, 312, 314-317, 322, 323, 331, 332, 337, 339, 341, and 344-347 in Table 2 are reported as follows: compound retention times were recorded using HPLC/MS conditions indicated in the table, and the molecular masses of the compounds were determined by MS (ES) by the formula m/z.

TABLE 2

| Ex. # | Structure | Name | RT (min) | [M + 1]$^+$ | LC/MS Methods |
|---|---|---|---|---|---|
| 6 | 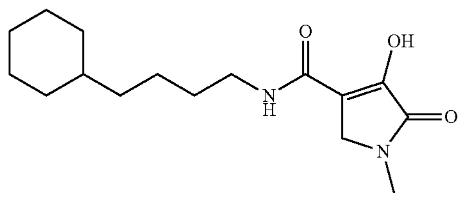 [SMILES: CN1CC(C(=O)NCCCCC2CCCCC2)=C(O)C1=O] | N-(4-cyclohexylbutyl)-4-hydroxy-1-methyl-5-oxo-2,5-dihydro-1H-pyrrole-3-carboxamide | 1.61 | 295.2 | E |
| 7 | 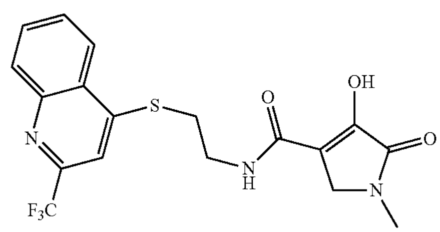 [SMILES: CN1CC(C(=O)NCCSc2cc(C(F)(F)F)nc3ccccc23)=C(O)C1=O] | 4-hydroxy-1-methyl-5-oxo-N-(2-(2-(trifluoromethyl)quinolin-4-ylthio)ethyl)-2,5-dihydro-1H-pyrrole-3-carboxamide | 2.84 | 412.1 | E |
| 9 | 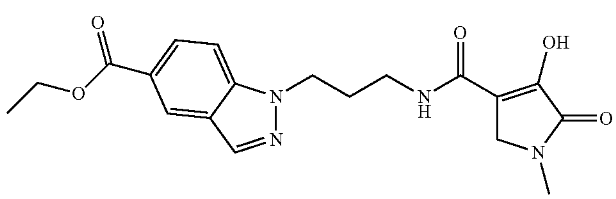 [SMILES: CCOC(=O)c1ccc2c(cnn2CCCNC(=O)C2=C(O)C(=O)N(C)C2)c1] | ethyl 1-(3-(4-hydroxy-1-methyl-5-oxo-2,5-dihydro-1H-pyrrole-3-carboxamido)propyl)-1H-indazole-5-carboxylate | 2.45 | 387.2 | E |
| 22 | 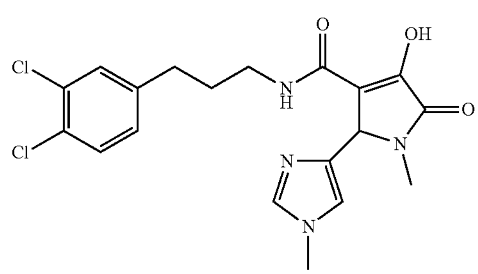 [SMILES: CN1C(=O)C(O)=C(C(=O)NCCCc2ccc(Cl)c(Cl)c2)C1c1cn(C)cn1] | N-(3-(3,4-dichlorophenyl)propyl)-4-hydroxy-1-methyl-2-(1-methyl-1H-imidazol-4-yl)-5-oxo-2,5-dihydro-1H-pyrrole-3-carboxamide | 1.34 | 422.9 | E |
| 33 | 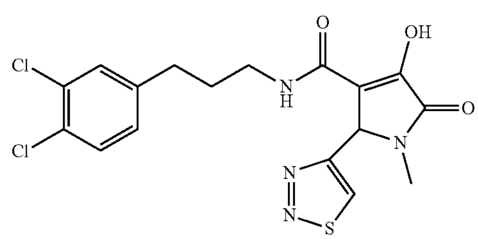 [SMILES: CN1C(=O)C(O)=C(C(=O)NCCCc2ccc(Cl)c(Cl)c2)C1c1csnn1] | N-(3-(3,4-dichlorophenyl)propyl)-4-hydroxy-1-methyl-5-oxo-2-(1,2,3-thiadiazol-4-yl)-2,5-dihydro-1H-pyrrole-3-carboxamide | 1.47 | 426.8 | E |

TABLE 2-continued

| Ex. # | Structure | Name | RT (min) | [M + 1]+ | LC/MS Methods |
|---|---|---|---|---|---|
| 48 | 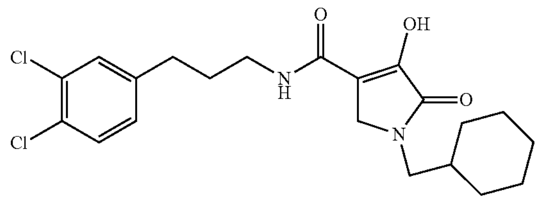 [SMILES: O=C(NCCCc1ccc(Cl)c(Cl)c1)C1=C(O)C(=O)N(CC2CCCCC2)C1] | 1-(cyclohexylmethyl)-N-(3-(3,4-dichlorophenyl)propyl)-4-hydroxy-5-oxo-2,5-dihydro-1H-pyrrole-3-carboxamide | 2.03 | 425.0 | E |
| 61 | 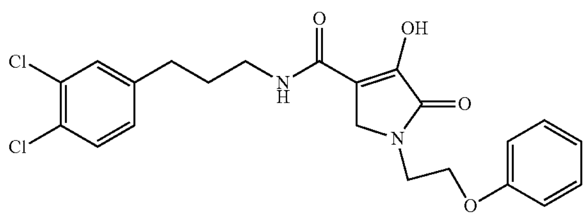 [SMILES: O=C(NCCCc1ccc(Cl)c(Cl)c1)C1=C(O)C(=O)N(CCOc2ccccc2)C1] | N-(3-(3,4-dichlorophenyl)propyl)-4-hydroxy-5-oxo-1-(2-phenoxyethyl)-2,5-dihydro-1H-pyrrole-3-carboxamide | 1.87 | 448.9 | E |
| 62 | Chiral | (R)-1-(1-benzylpyrrolidin-3-yl)-N-(3-(3,4-dichlorophenyl)propyl)-4-hydroxy-5-oxo-2,5-dihydro-1H-pyrrole-3-carboxamide | 2.24 | 487.9 | E |
| 63 | Chiral | (S)-1-(1-benzylpyrrolidin-3-yl)-N-(3-(3,4-dichlorophenyl)propyl)-4-hydroxy-5-oxo-2,5-dihydro-1H-pyrrole-3-carboxamide | 2.19 | 488.0 | E |
| 74 | 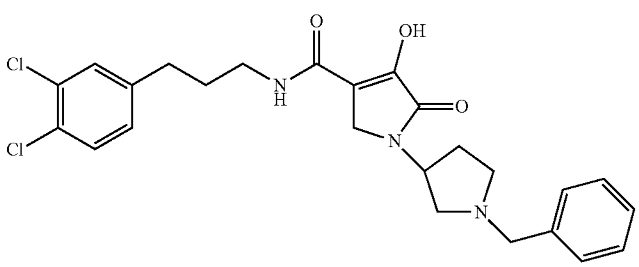 [SMILES: O=C(NCCCc1ccc(Cl)c(Cl)c1)C1=C(O)C(=O)N(C2CCN(Cc3ccccc3)C2)C1] | 1-(1-benzylpyrrolidin-3-yl)-N-(3-(3,4-dichlorophenyl)propyl)-4-hydroxy-5-oxo-2,5-dihydro-1H-pyrrole-3-carboxamide | 1.72 | 488.0 | E |
| 75 | 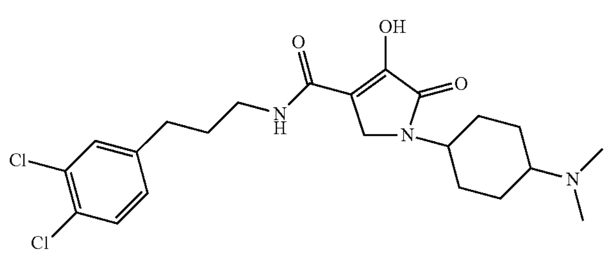 [SMILES: CN(C)C1CCC(N2CC(C(=O)NCCCc3ccc(Cl)c(Cl)c3)=C(O)C2=O)CC1] | N-(3-(3,4-dichlorophenyl)propyl)-1-(4-(dimethylamino)cyclohexyl)-4-hydroxy-5-oxo-2,5-dihydro-1H-pyrrole-3-carboxamide | 1.43 | 454.1 | E |

TABLE 2-continued

| Ex. # | Structure | Name | RT (min) | [M + 1]+ | LC/MS Methods |
|---|---|---|---|---|---|
| 81 | 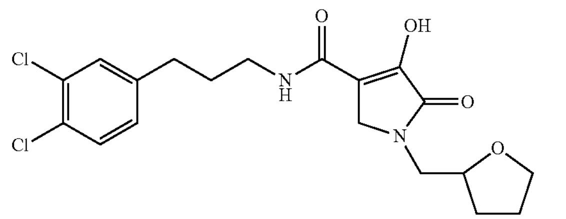 [SMILES: O=C(NCCCc1ccc(Cl)c(Cl)c1)C1=C(O)C(=O)N(CC2CCCO2)C1] | N-(3-(3,4-dichlorophenyl)propyl)-4-hydroxy-5-oxo-1-((tetrahydrofuran-2-yl)methyl)-2,5-dihydro-1H-pyrrole-3-carboxamide | 1.51 | 413.0 | E |
| 83 | 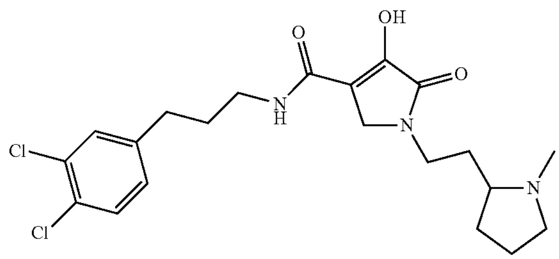 [SMILES: CN1CCCC1CCN1CC(C(=O)NCCCc2ccc(Cl)c(Cl)c2)=C(O)C1=O] | N-(3-(3,4-dichlorophenyl)propyl)-4-hydroxy-1-(2-(1-methylpyrrolidin-2-yl)ethyl)-5-oxo-2,5-dihydro-1H-pyrrole-3-carboxamide | 1.43 | 440.1 | E |
| 84 | 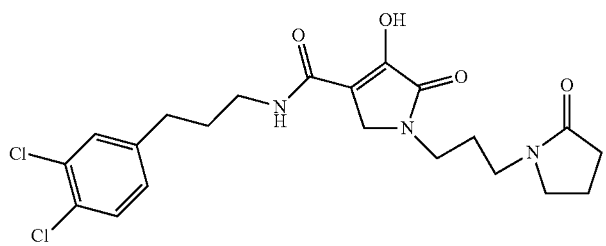 [SMILES: O=C(NCCCc1ccc(Cl)c(Cl)c1)C1=C(O)C(=O)N(CCCN2CCCC2=O)C1] | N-(3-(3,4-dichlorophenyl)propyl)-4-hydroxy-5-oxo-1-(3-(2-oxopyrrolidin-1-yl)propyl)-2,5-dihydro-1H-pyrrole-3-carboxamide | 1.44 | 454.0 | E |
| 85 | 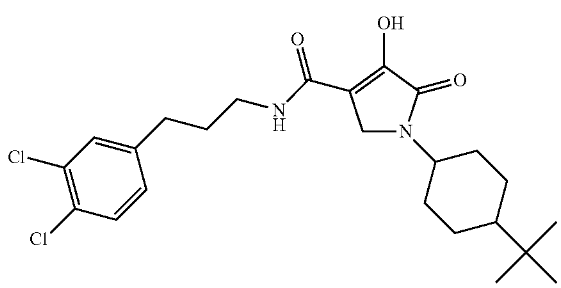 [SMILES: CC(C)(C)C1CCC(N2CC(C(=O)NCCCc3ccc(Cl)c(Cl)c3)=C(O)C2=O)CC1] | 1-(4-tert-butylcyclohexyl)-N-(3-(3,4-dichlorophenyl)propyl)-4-hydroxy-5-oxo-2,5-dihydro-1H-pyrrole-3-carboxamide | 2.42 | 467.0 | E |
| 87 | 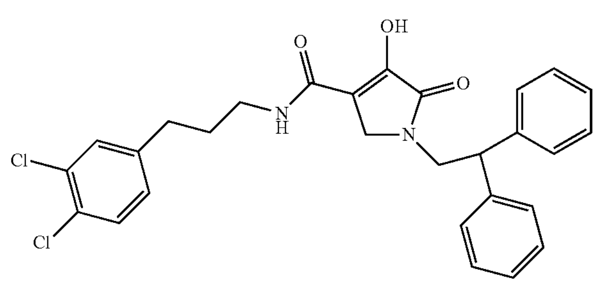 [SMILES: O=C(NCCCc1ccc(Cl)c(Cl)c1)C1=C(O)C(=O)N(CC(c2ccccc2)c2ccccc2)C1] | N-(3-(3,4-dichlorophenyl)propyl)-1-(2,2-diphenylethyl)-4-hydroxy-5-oxo-2,5-dihydro-1H-pyrrole-3-carboxamide | 2.15 | 509.0 | E |

TABLE 2-continued

| Ex. # | Structure | Name | RT (min) | [M + 1]+ | LC/MS Methods |
|---|---|---|---|---|---|
| 88 | 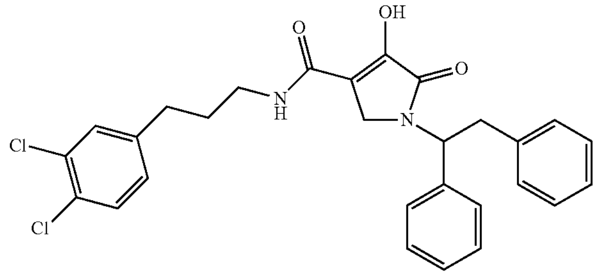 [SMILES: O=C(NCCCc1ccc(Cl)c(Cl)c1)C1=C(O)C(=O)N(C(Cc2ccccc2)c2ccccc2)C1] | N-(3-(3,4-dichlorophenyl)propyl)-1-(1,2-diphenylethyl)-4-hydroxy-5-oxo-2,5-dihydro-1H-pyrrole-3-carboxamide | 2.16 | 509.0 | E |
| 96 | 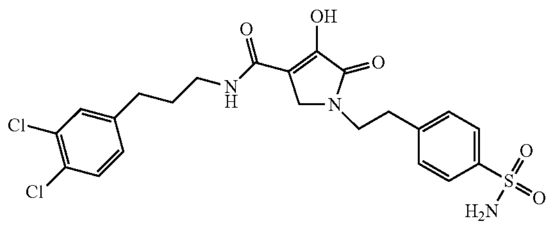 [SMILES: NS(=O)(=O)c1ccc(CCN2CC(C(=O)NCCCc3ccc(Cl)c(Cl)c3)=C(O)C2=O)cc1] | N-(3-(3,4-dichlorophenyl)propyl)-4-hydroxy-5-oxo-1-(4-sulfamoylphenethyl)-2,5-dihydro-1H-pyrrole-3-carboxamide | 1.49 | 511.9 | E |
| 98 | 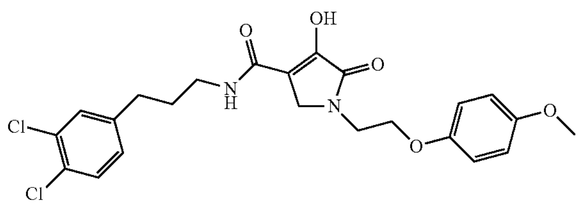 | N-(3-(3,4-dichlorophenyl)propyl)-4-hydroxy-1-(2-(4-methoxyphenoxy)ethyl)-5-oxo-2,5-dihydro-1H-pyrrole-3-carboxamide | 1.80 | 478.9 | E |
| 100 | 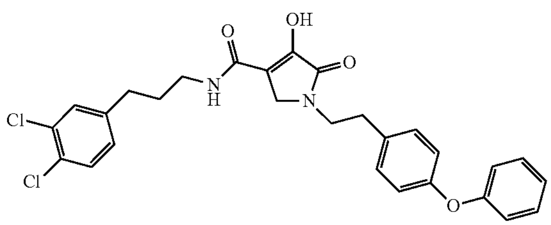 [SMILES: O=C(NCCCc1ccc(Cl)c(Cl)c1)C1=C(O)C(=O)N(CCc2ccc(Oc3ccccc3)cc2)C1] | N-(3-(3,4-dichlorophenyl)propyl)-4-hydroxy-5-oxo-1-(4-phenoxyphenethyl)-2,5-dihydro-1H-pyrrole-3-carboxamide | 2.25 | 524.9 | E |
| 101 | 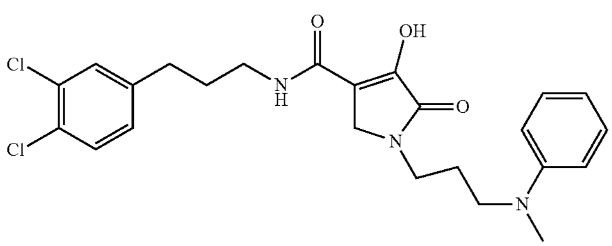 [SMILES: CN(CCCN1CC(C(=O)NCCCc2ccc(Cl)c(Cl)c2)=C(O)C1=O)c1ccccc1] | N-(3-(3,4-dichlorophenyl)propyl)-4-hydroxy-1-(3-(methyl(phenyl)amino)propyl)-5-oxo-2,5-dihydro-1H-pyrrole-3-carboxamide | 1.99 | 476.0 | E |
| 103 | 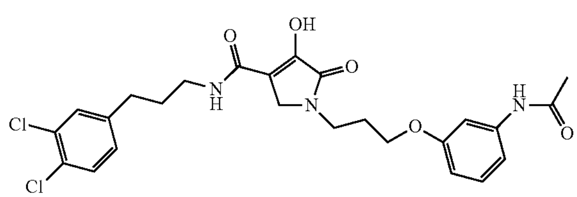 [SMILES: CC(=O)Nc1cccc(OCCCN2CC(C(=O)NCCCc3ccc(Cl)c(Cl)c3)=C(O)C2=O)c1] | 1-(3-(3-acetamidophenoxy)propyl)-N-(3-(3,4-dichlorophenyl)propyl)-4-hydroxy-5-oxo-2,5-dihydro-1H-pyrrole-3-carboxamide | 1.63 | 520.0 | E |

TABLE 2-continued

| Ex. # | Structure | Name | RT (min) | [M + 1]+ | LC/MS Methods |
|---|---|---|---|---|---|
| 104 | 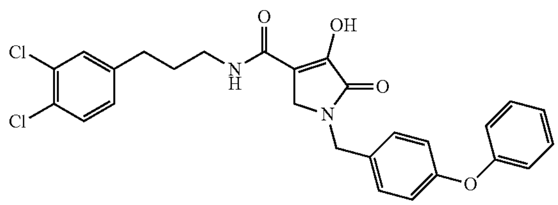 [SMILES: O=C(NCCCc1ccc(Cl)c(Cl)c1)C1=C(O)C(=O)N(Cc2ccc(Oc3ccccc3)cc2)C1] | N-(3-(3,4-dichlorophenyl) propyl)-4-hydroxy-5-oxo-1-(4-phenoxybenzyl)-2,5-dihydro-1H-pyrrole-3-carboxamide | 2.16 | 510.9 | E |
| 105 | 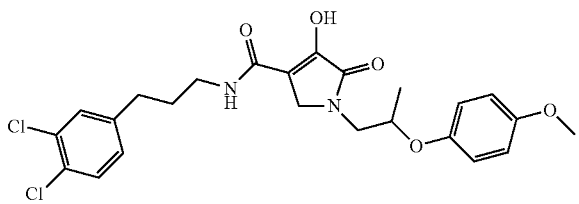 [SMILES: COc1ccc(OC(C)CN2CC(C(=O)NCCCc3ccc(Cl)c(Cl)c3)=C(O)C2=O)cc1] | N-(3-(3,4-dichlorophenyl) propyl)-4-hydroxy-1-(2-(4-methoxyphenoxy)propyl)-5-oxo-2,5-dihydro-1H-pyrrole-3-carboxamide | 1.87 | 492.9 | E |
| 106 | 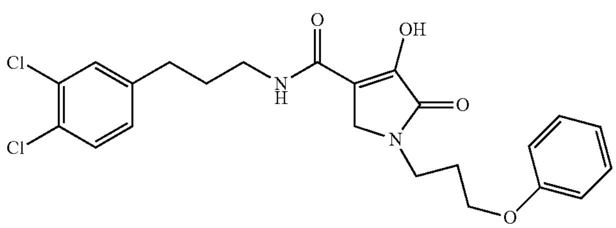 [SMILES: O=C(NCCCc1ccc(Cl)c(Cl)c1)C1=C(O)C(=O)N(CCCOc2ccccc2)C1] | N-(3-(3,4-dichlorophenyl) propyl)-4-hydroxy-5-oxo-1-(3-phenoxypropyl)-2,5-dihydro-1H-pyrrole-3-carboxamide | 1.91 | 463.0 | E |
| 107 | 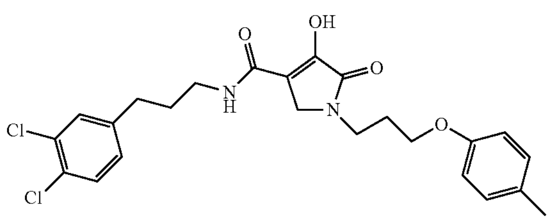 [SMILES: Cc1ccc(OCCCN2CC(C(=O)NCCCc3ccc(Cl)c(Cl)c3)=C(O)C2=O)cc1] | N-(3-(3,4-dichlorophenyl) propyl)-4-hydroxy-5-oxo-1-(3-(p-tolyloxy)propyl)-2,5-dihydro-1H-pyrrole-3-carboxamide | 2.05 | 477.0 | E |
| 108 | 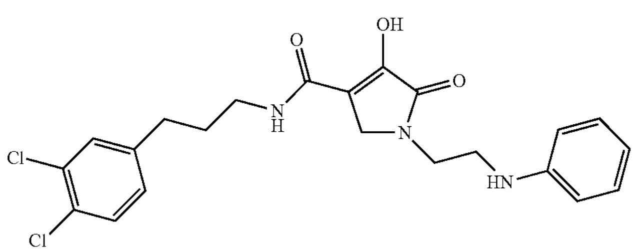 [SMILES: O=C(NCCCc1ccc(Cl)c(Cl)c1)C1=C(O)C(=O)N(CCNc2ccccc2)C1] | N-(3-(3,4-dichlorophenyl) propyl)-4-hydroxy-5-oxo-1-(2-(phenylamino) ethyl)-2,5-dihydro-1H-pyrrole-3-carboxamide | 1.79 | 448.0 | E |
| 111 | 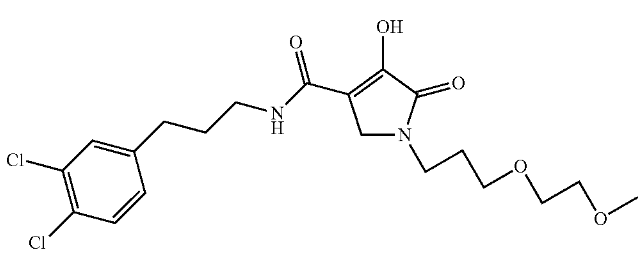 [SMILES: COCCOCCCN1CC(C(=O)NCCCc2ccc(Cl)c(Cl)c2)=C(O)C1=O] | N-(3-(3,4-dichlorophenyl) propyl)-4-hydroxy-1-(3-(2-methoxyethoxy)propyl)-5-oxo-2,5-dihydro-1H-pyrrole-3-carboxamide | 1.50 | 445.0 | E |

| Ex. # | Structure | Name | RT (min) | [M + 1]+ | LC/MS Methods |
|---|---|---|---|---|---|
| 115 | 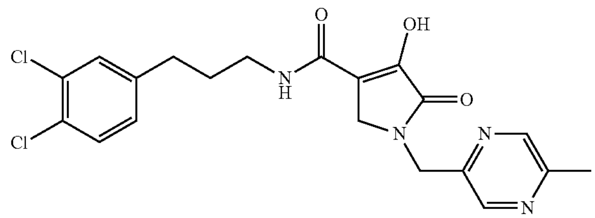 [SMILES: Cc1cnc(CN2CC(C(=O)NCCCc3ccc(Cl)c(Cl)c3)=C(O)C2=O)cn1] | N-(3-(3,4-dichlorophenyl)propyl)-4-hydroxy-1-((5-methylpyrazin-2-yl)methyl)-5-oxo-2,5-dihydro-1H-pyrrole-3-carboxamide | 1.43 | 435.0 | E |
| 118 | 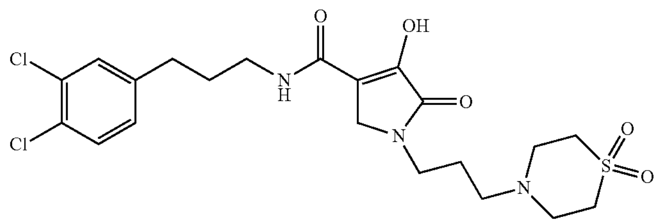 [SMILES: O=C(NCCCc1ccc(Cl)c(Cl)c1)C1=C(O)C(=O)N(CCCN2CCS(=O)(=O)CC2)C1] | N-(3-(3,4-dichlorophenyl)propyl)-1-(3-(1,1-dioxidothiomorpholin-4-yl)propyl)-4-hydroxy-5-oxo-2,5-dihydro-1H-pyrrole-3-carboxamide | 1.43 | 503.9 | E |
| 119 | 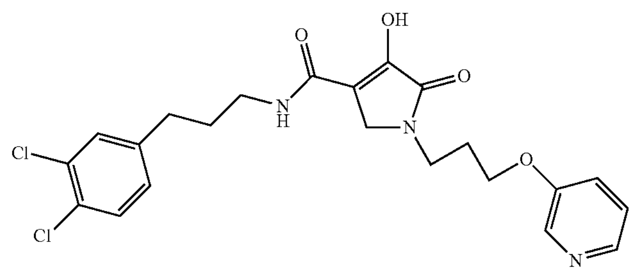 [SMILES: O=C(NCCCc1ccc(Cl)c(Cl)c1)C1=C(O)C(=O)N(CCCOc2cccnc2)C1] | N-(3-(3,4-dichlorophenyl)propyl)-4-hydroxy-5-oxo-1-(3-(pyridin-3-yloxy)propyl)-2,5-dihydro-1H-pyrrole-3-carboxamide | 1.56 | 464.0 | E |
| 123 | 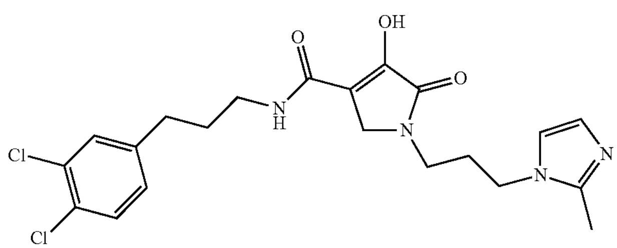 [SMILES: Cc1nccn1CCCN1CC(C(=O)NCCCc2ccc(Cl)c(Cl)c2)=C(O)C1=O] | N-(3-(3,4-dichlorophenyl)propyl)-4-hydroxy-1-(3-(2-methyl-1H-imidazol-1-yl)propyl)-5-oxo-2,5-dihydro-1H-pyrrole-3-carboxamide | 1.40 | 450.9 | E |
| 129 | 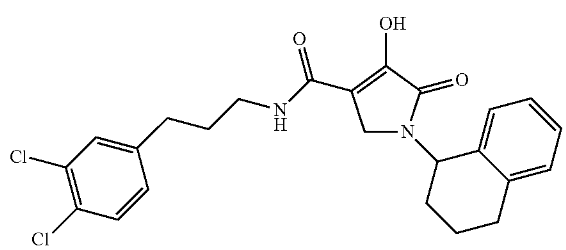 [SMILES: O=C(NCCCc1ccc(Cl)c(Cl)c1)C1=C(O)C(=O)N(C2CCCc3ccccc32)C1] | N-(3-(3,4-dichlorophenyl)propyl)-4-hydroxy-5-oxo-1-(1,2,3,4-tetrahydronaphthalen-1-yl)-2,5-dihydro-1H-pyrrole-3-carboxamide | 1.99 | 459.0 | E |
| 136 | Chiral | (S)-ethyl 2-(4-(3-(3,4-dichlorophenyl)propylcarbamoyl)-3-hydroxy-2-oxo-2,5-dihydro-1H-pyrrol-1-yl)-3-(4-fluorophenyl)propanoate | 2.58 | 522.7 | E |

TABLE 2-continued

| Ex. # | Structure | Name | RT (min) | [M + 1]+ | LC/MS Methods |
|---|---|---|---|---|---|
| 138 | Chiral | (S)-ethyl 2-(4-(3-(3,4-dichlorophenyl)propylcarbamoyl)-3-hydroxy-2-oxo-2,5-dihydro-1H-pyrrol-1-yl)-3-phenylpropanoate | 2.54 | 504.7 | E |
| 139 | 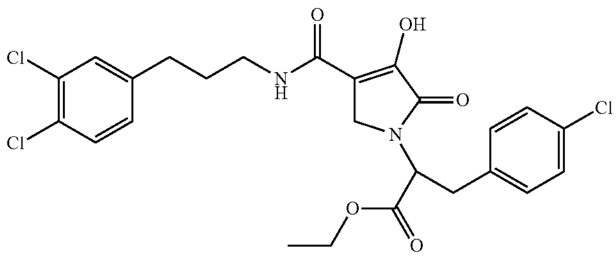 [SMILES: CCOC(=O)C(Cc1ccc(Cl)cc1)N1CC(C(=O)NCCCc2ccc(Cl)c(Cl)c2)=C(O)C1=O] | ethyl 3-(4-chlorophenyl)-2-(4-(3-(3,4-dichlorophenyl)propylcarbamoyl)-3-hydroxy-2-oxo-2,5-dihydro-1H-pyrrol-1-yl)propanoate | 2.73 | 538.7 | E |
| 140 | Chiral | (R)-ethyl 2-(4-(3-(3,4-dichlorophenyl)propylcarbamoyl)-3-hydroxy-2-oxo-2,5-dihydro-1H-pyrrol-1-yl)-2-phenylacetate | 2.48 | 490.7 | E |
| 151 | 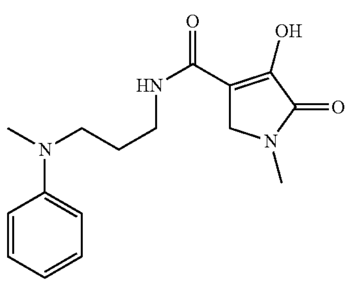 [SMILES: CN1CC(C(=O)NCCCN(C)c2ccccc2)=C(O)C1=O] | 4-hydroxy-1-methyl-N-(3-(methyl(phenyl)amino)propyl)-5-oxo-2,5-dihydro-1H-pyrrole-3-carboxamide | 0.74 | 304 | A |
| 169 | 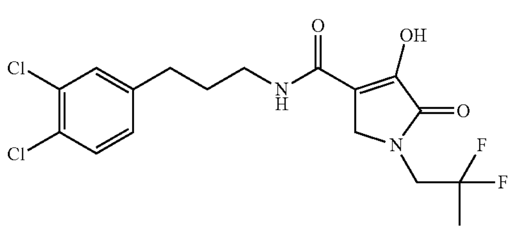 [SMILES: CC(F)(F)CN1CC(C(=O)NCCCc2ccc(Cl)c(Cl)c2)=C(O)C1=O] | N-(3-(3,4-dichlorophenyl)propyl)-1-(2,2-difluoropropyl)-4-hydroxy-5-oxo-2,5-dihydro-1H-pyrrole-3-carboxamide | 2.50 | 408.0 | A |
| 175 | 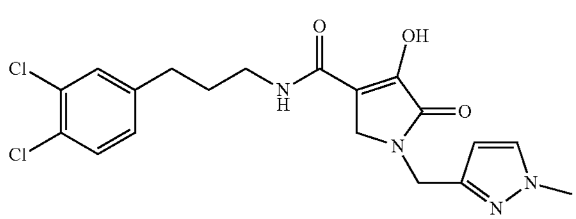 [SMILES: Cn1ccc(CN2CC(C(=O)NCCCc3ccc(Cl)c(Cl)c3)=C(O)C2=O)n1] | N-(3-(3,4-dichlorophenyl)propyl)-4-hydroxy-1-((1-methyl-1H-pyrazol-3-yl)methyl)-5-oxo-2,5-dihydro-1H-pyrrole-3-carboxamide | 0.92 | 423.1 | D |

TABLE 2-continued

| Ex. # | Structure | Name | RT (min) | [M + 1]+ | LC/MS Methods |
|---|---|---|---|---|---|
| 190 | 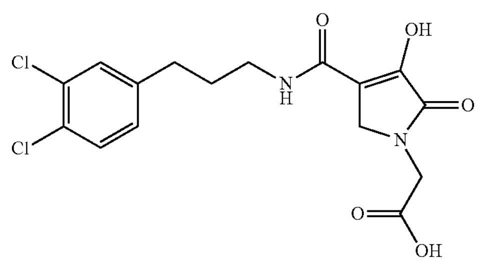 [SMILES: O=C(O)CN1CC(C(=O)NCCCc2ccc(Cl)c(Cl)c2)=C(O)C1=O] | 2-(4-(3-(3,4-dichlorophenyl) propylcarbamoyl)-3-hydroxy-2-oxo-2,5-dihydro-1H-pyrrol-1-yl)acetic acid | 2.1 | 388.0 | C |
| 200 | 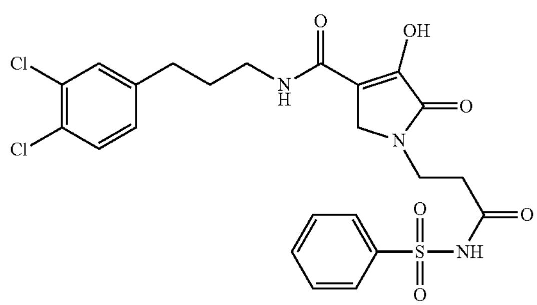 [SMILES: O=C(CCN1CC(C(=O)NCCCc2ccc(Cl)c(Cl)c2)=C(O)C1=O)NS(=O)(=O)c1ccccc1] | N-(3-(3,4-dichlorophenyl) propyl)-4-hydroxy-5-oxo-1-(3-oxo-3-(phenylsulfonamido)propyl)-2,5-dihydro-1H-pyrrole-3-carboxamide | 2.50 | 541.0 | C |
| 201 | 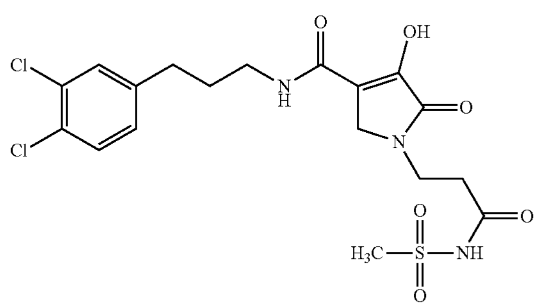 [SMILES: CS(=O)(=O)NC(=O)CCN1CC(C(=O)NCCCc2ccc(Cl)c(Cl)c2)=C(O)C1=O] | N-(3-(3,4-dichlorophenyl) propyl)-4-hydroxy-1-(3-(methylsulfonamido)-3-oxopropyl)-5-oxo-2,5-dihydro-1H-pyrrole-3-carboxamide | 2.30 | 479.0 | C |
| 203 | 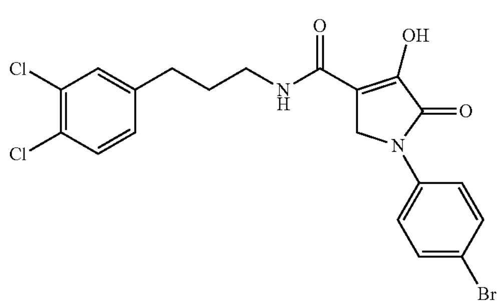 [SMILES: O=C(NCCCc1ccc(Cl)c(Cl)c1)C1=C(O)C(=O)N(c2ccc(Br)cc2)C1] | 1-(4-bromophenyl)-N-(3-(3,4-dichlorophenyl) propyl)-4-hydroxy-5-oxo-2,5-dihydro-1H-pyrrole-3-carboxamide | 2.34 | 484.8 | L |
| 212 | 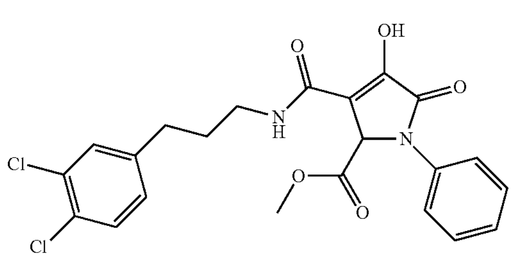 [SMILES: COC(=O)C1C(C(=O)NCCCc2ccc(Cl)c(Cl)c2)=C(O)C(=O)N1c1ccccc1] | methyl 3-(3-(3,4-dichlorophenyl) propylcarbamoyl)-4-hydroxy-5-oxo-1-phenyl-2,5-dihydro-1H-pyrrole-2-carboxylate | 1.81 | 463.1 | M |

TABLE 2-continued

| Ex. # | Structure | Name | RT (min) | [M + 1]+ | LC/MS Methods |
|---|---|---|---|---|---|
| 217 | 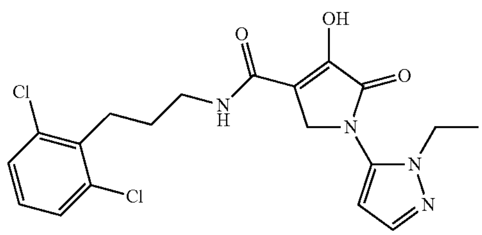 [SMILES: CCn1nccc1N1CC(C(=O)NCCCc2c(Cl)cccc2Cl)=C(O)C1=O] | N-(3-(2,6-dichlorophenyl) propyl)-1-(1-ethyl-1H-pyrazol-5-yl)-4-hydroxy-5-oxo-2,5-dihydro-1H-pyrrole-3-carboxamide | 2.02 | 423.1 | L |
| 219 | 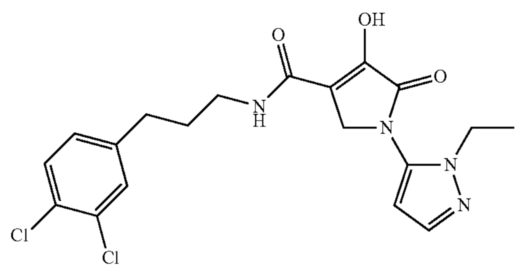 [SMILES: CCn1nccc1N1CC(C(=O)NCCCc2ccc(Cl)c(Cl)c2)=C(O)C1=O] | N-(3-(3,4-dichlorophenyl) propyl)-1-(1-ethyl-1H-pyrazol-5-yl)-4-hydroxy-5-oxo-2,5-dihydro-1H-pyrrole-3-carboxamide | 2.04 | 423.3 | L |
| 220 | 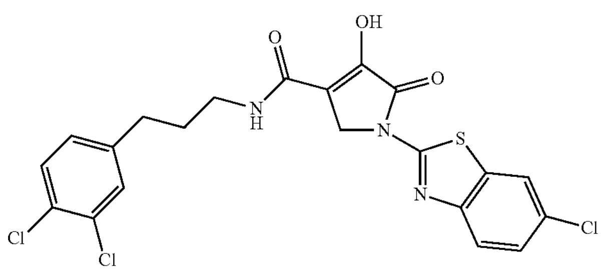 [SMILES: O=C(NCCCc1ccc(Cl)c(Cl)c1)C1=C(O)C(=O)N(c2nc3ccc(Cl)cc3s2)C1] | 1-(6-chlorobenzo[d]thiazol-2-yl)-N-(3-(3,4-dichlorophenyl)propyl)-4-hydroxy-5-oxo-2,5-dihydro-1H-pyrrole-3-carboxamide | 2.10 | 496.1 | M |
| 222 | 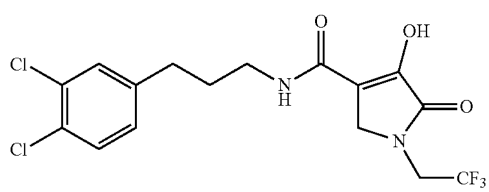 [SMILES: O=C(NCCCc1ccc(Cl)c(Cl)c1)C1=C(O)C(=O)N(CC(F)(F)F)C1] | N-(4-(3,4-dichlorophenyl) butan-2-yl)-4-hydroxy-5-oxo-1-(2,2,2-trifluoroethyl)-2,5-dihydro-1H-pyrrole-3-carboxamide | 2.21 | 424.9 | O |
| 232 | from (R)-2-methylpropane-2-sulfinamide | N-(1-cyclopropyl-3-(3,4-dichlorophenyl)propyl)-4-hydroxy-1-methyl-5-oxo-2,5-dihydro-1H-pyrrole-3-carboxamide | 1.00 | 383.1 | D |
| 233 | from (S)-2-methylpropane-2-sulfinamide | N-(1-cyclopropyl-3-(3,4-dichlorophenyl)propyl)-4-hydroxy-1-methyl-5-oxo-2,5-dihydro-1H-pyrrole-3-carboxamide | 1.00 | 383.1 | D |

TABLE 2-continued

| Ex. # | Structure | Name | RT (min) | [M + 1]+ | LC/ MS Methods |
|---|---|---|---|---|---|
| 236 | from (S)-2-methylpropane-2-sulfinamide | N-(5-(3,4-dichlorophenyl)pent-1-en-3-yl)-4-hydroxy-1-methyl-5-oxo-2,5-dihydro-1H-pyrrole-3-carboxamide | 0.96 | 369.1 | D |
| 237 | from (R)-2-methylpropane-2-sulfinamide | N-(5-(3,4-dichlorophenyl)pent-1-en-3-yl)-4-hydroxy-1-methyl-5-oxo-2,5-dihydro-1H-pyrrole-3-carboxamide | 0.94 | 369.1 | D |
| 243 | 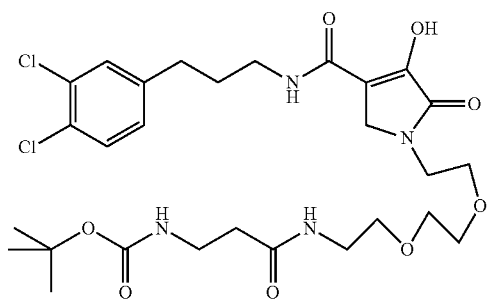 [SMILES: CC(C)(C)OC(=O)NCCC(=O)NCCOCCOCCN1CC(C(=O)NCCCc2ccc(Cl)c(Cl)c2)=C(O)C1=O] | tert-butyl 3-(2-(2-(2-(4-(3-(3,4-dichlorophenyl)propylcarbamoyl)-3-hydroxy-2-oxo-2,5-dihydro-1H-pyrrol-1-yl)ethoxy)ethoxy)ethylamino)-3-oxopropylcarbamate | 2.14 | 631.1 | L |
| 253 | 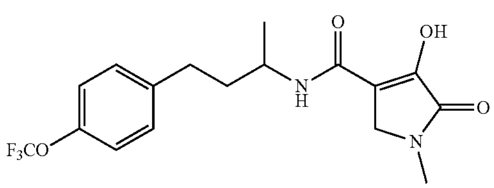 [SMILES: CC(CCc1ccc(OC(F)(F)F)cc1)NC(=O)C1=C(O)C(=O)N(C)C1] | 4-hydroxy-1-methyl-5-oxo-N-(4-(4-(trifluoromethoxy)phenyl)butan-2-yl)-2,5-dihydro-1H-pyrrole-3-carboxamide | 1.96 | 373.2 | L |
| 259 | 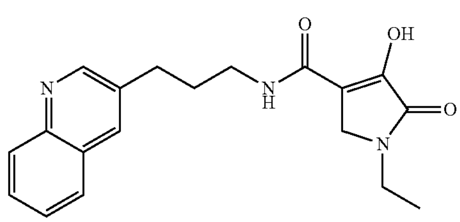 [SMILES: CCN1CC(C(=O)NCCCc2cnc3ccccc3c2)=C(O)C1=O] | 1-ethyl-4-hydroxy-5-oxo-N-(3-(quinolin-3-yl)propyl)-2,5-dihydro-1H-pyrrole-3-carboxamide | 1.13 | 340.1 | L |
| 263 | 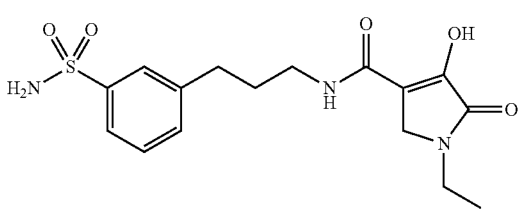 [SMILES: CCN1CC(C(=O)NCCCc2cccc(S(N)(=O)=O)c2)=C(O)C1=O] | 1-ethyl-4-hydroxy-5-oxo-N-(3-(3-sulfamoylphenyl)propyl)-2,5-dihydro-1H-pyrrole-3-carboxamide | 1.38 | 368.1 | L |

TABLE 2-continued

| Ex. # | Structure | Name | RT (min) | [M + 1]+ | LC/MS Methods |
|---|---|---|---|---|---|
| 274 | 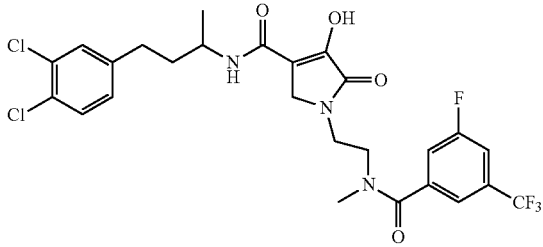 [SMILES: CC(CCc1ccc(Cl)c(Cl)c1)NC(=O)C1=C(O)C(=O)N(CCN(C)C(=O)c2cc(F)cc(C(F)(F)F)c2)C1] | N-(4-(3,4-dichlorophenyl) butan-2-yl)-1-(2-(3-fluoro-N-methyl-5-(trifluoromethyl)benzamido) ethyl)-4-hydroxy-5-oxo-2,5-dihydro-1H-pyrrole-3-carboxamide | 2.2 | 590.0 | L |
| 275 | 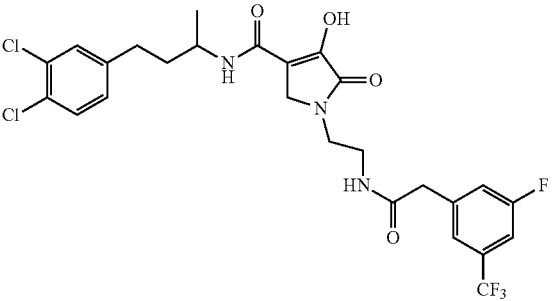 [SMILES: CC(CCc1ccc(Cl)c(Cl)c1)NC(=O)C1=C(O)C(=O)N(CCNC(=O)Cc2cc(F)cc(C(F)(F)F)c2)C1] | N-(4-(3,4-dichlorophenyl) butan-2-yl)-1-(2-(2-(3-fluoro-5-(trifluoromethyl)phenyl) acetamido)ethyl)-4-hydroxy-5-oxo-2,5-dihydro-1H-pyrrole-3-carboxamide | 2.2 | 590.0 | L |
| 276 | 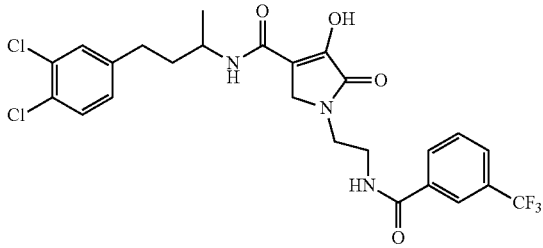 [SMILES: CC(CCc1ccc(Cl)c(Cl)c1)NC(=O)C1=C(O)C(=O)N(CCNC(=O)c2cccc(C(F)(F)F)c2)C1] | N-(4-(3,4-dichlorophenyl) butan-2-yl)-4-hydroxy-5-oxo-1-(2-(3-(trifluoromethyl)benzamido) ethyl)-2,5-dihydro-1H-pyrrole-3-carboxamide | 2.202 | 557.9 | L |
| 277 | 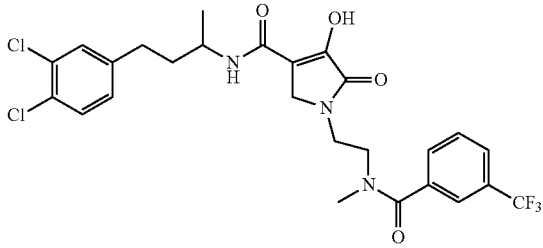 [SMILES: CC(CCc1ccc(Cl)c(Cl)c1)NC(=O)C1=C(O)C(=O)N(CCN(C)C(=O)c2cccc(C(F)(F)F)c2)C1] | N-(4-(3,4-dichlorophenyl) butan-2-yl)-4-hydroxy-1-(2-(N-methyl-3-(trifluoromethyl)benzamido) ethyl)-5-oxo-2,5-dihydro-1H-pyrrole-3-carboxamide | 2.75 | 572.0 | L |
| 279 | 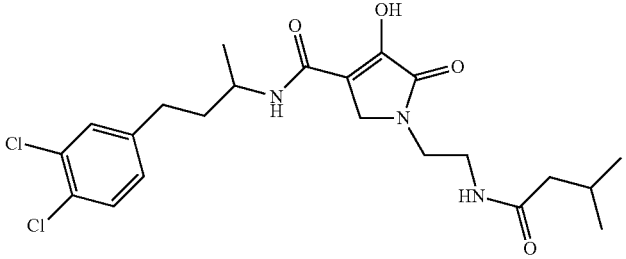 [SMILES: CC(C)CC(=O)NCCN1CC(C(=O)NC(C)CCc2ccc(Cl)c(Cl)c2)=C(O)C1=O] | N-(4-(3,4-dichlorophenyl) butan-2-yl)-4-hydroxy-1-(2-(3-methylbutanamido) ethyl)-5-oxo-2,5-dihydro-1H-pyrrole-3-carboxamide | 2.1 | 470.0 | L |

TABLE 2-continued

| Ex. # | Name | RT (min) | [M + 1]+ | LC/MS Methods |
|---|---|---|---|---|
| 280 | N-(4-(3,4-dichlorophenyl) butan-2-yl)-4-hydroxy-1-(2-(N-methylacetamido) ethyl)-5-oxo-2,5-dihydro-1H-pyrrole-3-carboxamide | 1.93 | 442.0 | L |
| 282 | N-(4-(3,4-dichlorophenyl) butan-2-yl)-4-hydroxy-1-(2-(1-methyl-3-(3-(trifluoromethyl)phenyl)ureido) ethyl)-5-oxo-2,5-dihydro-1H-pyrrole-3-carboxamide | 276.70 | 587.0 | L |
| 283 | N-(3-(3,4-dichlorophenyl) propyl)-4-(2-ethoxyethylamino)-1-ethyl-5-oxo-2,5-dihydro-1H-pyrrole-3-carboxamide | 1.05 | 428.2 | D |
| 284 | N-(3-(3,4-dichlorophenyl) propyl)-1-ethyl-5-oxo-4-(3-(piperidin-1-yl) propylamino)-2,5-dihydro-1H-pyrrole-3-carboxamide | 0.88 | 481.1 | D |
| 285 | N-(3-(3,4-dichlorophenyl) propyl)-1-ethyl-4-(2-(1-methylpyrrolidin-2-yl) ethylamino)-5-oxo-2,5-dihydro-1H-pyrrole-3-carboxamide | 0.86 | 466.6 | D |

TABLE 2-continued

| Ex. # | Structure | Name | RT (min) | [M + 1]+ | LC/MS Methods |
|---|---|---|---|---|---|
| 286 | 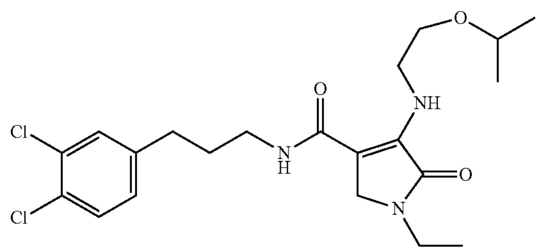 [SMILES: CCN1CC(C(=O)NCCCc2ccc(Cl)c(Cl)c2)=C(NCCOC(C)C)C1=O] | N-(3-(3,4-dichlorophenyl)propyl)-1-ethyl-4-(2-isopropoxyethylamino)-5-oxo-2,5-dihydro-1H-pyrrole-3-carboxamide | 1.09 | 442.2 | D |
| 287 | 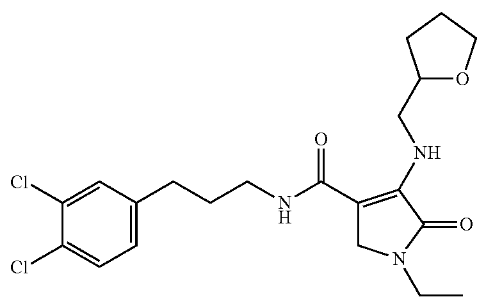 [SMILES: CCN1CC(C(=O)NCCCc2ccc(Cl)c(Cl)c2)=C(NCC2CCCO2)C1=O] | N-(3-(3,4-dichlorophenyl)propyl)-1-ethyl-5-oxo-4-((tetrahydrofuran-2-yl)methylamino)-2,5-dihydro-1H-pyrrole-3-carboxamide | 1.04 | 440.2 | D |
| 288 | 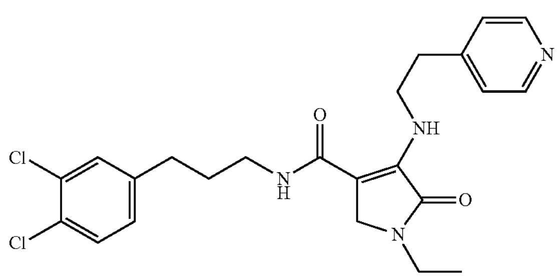 [SMILES: CCN1CC(C(=O)NCCCc2ccc(Cl)c(Cl)c2)=C(NCCc2ccncc2)C1=O] | N-(3-(3,4-dichlorophenyl)propyl)-1-ethyl-5-oxo-4-(2-(pyridin-4-yl)ethylamino)-2,5-dihydro-1H-pyrrole-3-carboxamide | 0.84 | 462.0 | D |
| 289 | 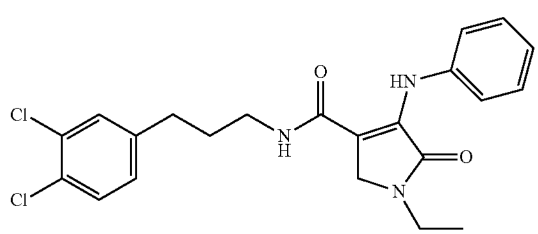 [SMILES: CCN1CC(C(=O)NCCCc2ccc(Cl)c(Cl)c2)=C(Nc2ccccc2)C1=O] | N-(3-(3,4-dichlorophenyl)propyl)-1-ethyl-5-oxo-4-(phenylamino)-2,5-dihydro-1H-pyrrole-3-carboxamide | 1.07 | 432.1 | D |
| 290 | 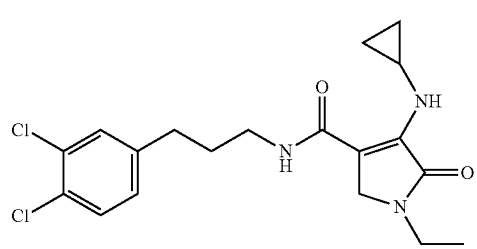 [SMILES: CCN1CC(C(=O)NCCCc2ccc(Cl)c(Cl)c2)=C(NC2CC2)C1=O] | 4-(cyclopropylamino)-N-(3-(3,4-dichlorophenyl)propyl)-1-ethyl-5-oxo-2,5-dihydro-1H-pyrrole-3-carboxamide | 1.03 | 396.2 | D |
| 291 | 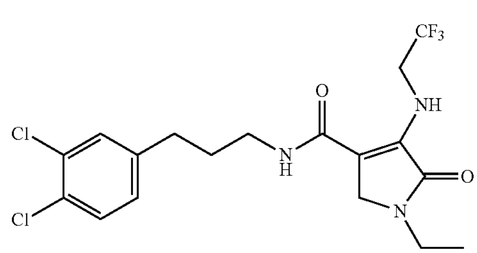 [SMILES: CCN1CC(C(=O)NCCCc2ccc(Cl)c(Cl)c2)=C(NCC(F)(F)F)C1=O] | N-(3-(3,4-dichlorophenyl)propyl)-1-ethyl-5-oxo-4-(2,2,2-trifluoroethylamino)-2,5-dihydro-1H-pyrrole-3-carboxamide | 1.08 | 438.0 | D |

TABLE 2-continued

| Ex. # | Structure | Name | RT (min) | [M + 1]+ | LC/MS Methods |
|---|---|---|---|---|---|
| 297 | 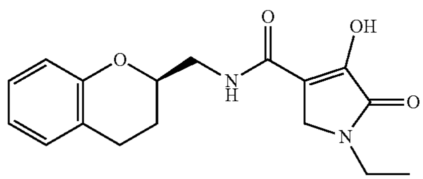 | (R)-N-(chroman-2-ylmethyl)-1-ethyl-4-hydroxy-5-oxo-2,5-dihydro-1H-pyrrole-3-carboxamide | 1.772 | 317.0 | L |
| 298 | 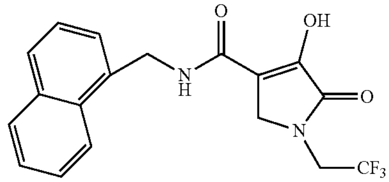 [SMILES: O=C(NCc1cccc2ccccc12)C1=C(O)C(=O)N(CC(F)(F)F)C1] | 4-hydroxy-N-(naphthalen-1-ylmethyl)-5-oxo-1-(2,2,2-trifluoroethyl)-2,5-dihydro-1H-pyrrole-3-carboxamide | 1.47 | 364.99 | E |
| 299 | 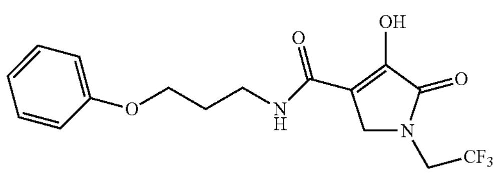 [SMILES: O=C(NCCCOc1ccccc1)C1=C(O)C(=O)N(CC(F)(F)F)C1] | 4-hydroxy-5-oxo-N-(3-phenoxypropyl)-1-(2,2,2-trifluoroethyl)-2,5-dihydro-1H-pyrrole-3-carboxamide | 1.38 | 359.03 | E |
| 300 | 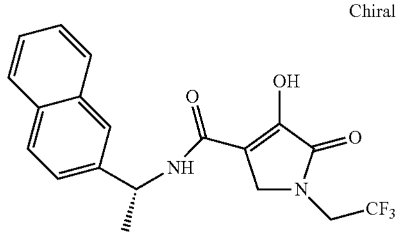 [SMILES: C[C@@H](NC(=O)C1=C(O)C(=O)N(CC(F)(F)F)C1)c1ccc2ccccc2c1] | (R)-4-hydroxy-N-(1-(naphthalen-2-yl)ethyl)-5-oxo-1-(2,2,2-trifluoroethyl)-2,5-dihydro-1H-pyrrole-3-carboxamide | 1.56 | 379.01 | E |
| 301 | 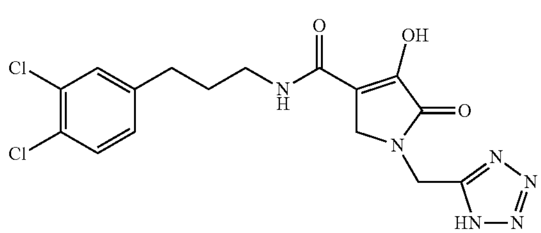 [SMILES: O=C(NCCCc1ccc(Cl)c(Cl)c1)C1=C(O)C(=O)N(Cc2nnn[nH]2)C1] | 1-((1H-tetrazol-5-yl)methyl)-N-(3-(3,4-dichlorophenyl)propyl)-4-hydroxy-5-oxo-2,5-dihydro-1H-pyrrole-3-carboxamide | 0.87 | 411.1 | |
| 302 | 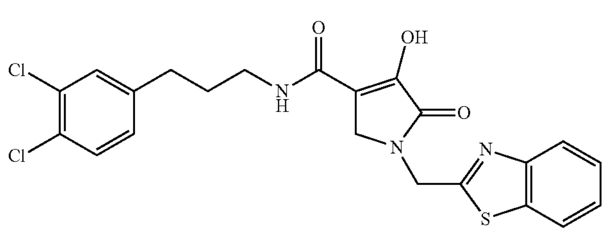 [SMILES: O=C(NCCCc1ccc(Cl)c(Cl)c1)C1=C(O)C(=O)N(Cc2nc3ccccc3s2)C1] | 1-(benzo[d]thiazol-2-ylmethyl)-N-(3-(3,4-dichlorophenyl)propyl)-4-hydroxy-5-oxo-2,5-dihydro-1H-pyrrole-3-carboxamide | 1.04 | 476.1 | D |

TABLE 2-continued

| Ex. # | Structure | Name | RT (min) | [M + 1]+ | LC/MS Methods |
|---|---|---|---|---|---|
| 303 | 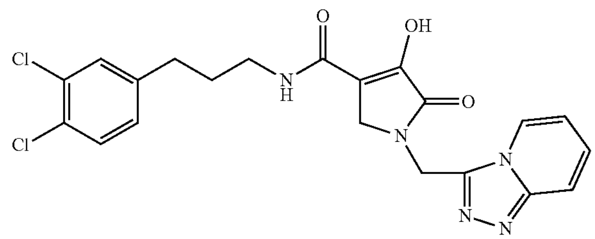 [SMILES: O=C(NCCCc1ccc(Cl)c(Cl)c1)C1=C(O)C(=O)N(Cc2nnc3ccccn23)C1] | 1-([1,2,4]triazolo[4,3-a]pyridin-3-ylmethyl)-N-(3-(3,4-dichlorophenyl)propyl)-4-hydroxy-5-oxo-2,5-dihydro-1H-pyrrole-3-carboxamide | 0.84 | 460.1 | D |
| 304 | 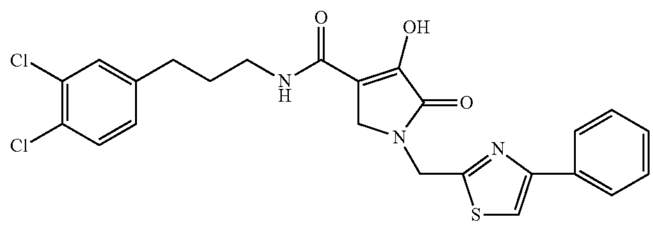 [SMILES: O=C(NCCCc1ccc(Cl)c(Cl)c1)C1=C(O)C(=O)N(Cc2nc(-c3ccccc3)cs2)C1] | N-(3-(3,4-dichlorophenyl)propyl)-4-hydroxy-5-oxo-1-((4-phenylthiazol-2-yl)methyl)-2,5-dihydro-1H-pyrrole-3-carboxamide | 1.08 | 502.1 | D |
| 305 | Chiral | (R)-N-(3-(3,4-dichlorophenyl)propyl)-4-hydroxy-1-(2-hydroxy-2-phenylethyl)-5-oxo-2,5-dihydro-1H-pyrrole-3-carboxamide | 0.97 | 449.1 | D |
| 306 | 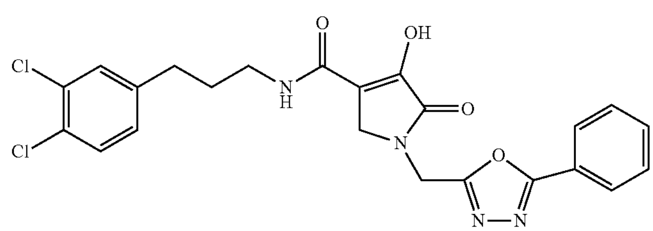 [SMILES: O=C(NCCCc1ccc(Cl)c(Cl)c1)C1=C(O)C(=O)N(Cc2nnc(-c3ccccc3)o2)C1] | N-(3-(3,4-dichlorophenyl)propyl)-4-hydroxy-5-oxo-1-((5-phenyl-1,3,4-oxadiazol-2-yl)methyl)-2,5-dihydro-1H-pyrrole-3-carboxamide | 1.00 | 487.2 | D |
| 307 | Chiral | (S)-N-(3-(3,4-dichlorophenyl)propyl)-4-hydroxy-1-(2-hydroxy-2-phenylethyl)-5-oxo-2,5-dihydro-1H-pyrrole-3-carboxamide | 0.97 | 449.2 | D |

TABLE 2-continued

| Ex. # | Structure | Name | RT (min) | [M + 1]+ | LC/MS Methods |
|---|---|---|---|---|---|
| 314 | 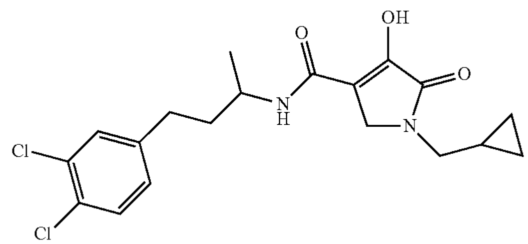 [SMILES: CC(CCc1ccc(Cl)c(Cl)c1)NC(=O)C1=C(O)C(=O)N(CC2CC2)C1] | 1-(cyclopropylmethyl)-N-(4-(3,4-dichlorophenyl)butan-2-yl)-4-hydroxy-5-oxo-2,5-dihydro-1H-pyrrole-3-carboxamide | 1.03 | 397.1 | D |
| 312 | 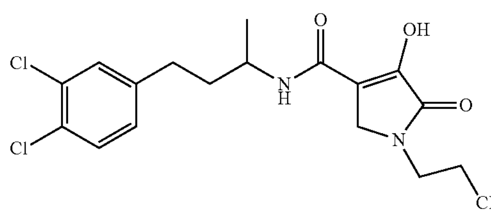 | N-(4-(3,4-dichlorophenyl)butan-2-yl)-4-hydroxy-5-oxo-1-(3,3,3-trifluoropropyl)-2,5-dihydro-1H-pyrrole-3-carboxamide | 1.03 | 439.0 | D |
| 315 | 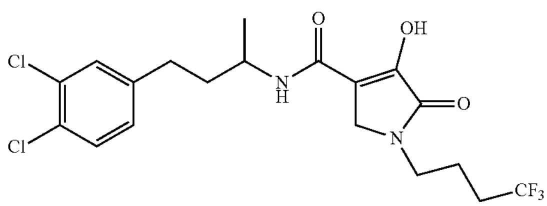 [SMILES: CC(CCc1ccc(Cl)c(Cl)c1)NC(=O)C1=C(O)C(=O)N(CCCC(F)(F)F)C1] | N-(4-(3,4-dichlorophenyl)butan-2-yl)-4-hydroxy-5-oxo-1-(4,4,4-trifluorobutyl)-2,5-dihydro-1H-pyrrole-3-carboxamide | 1.04 | 453.1 | D |
| 316 | 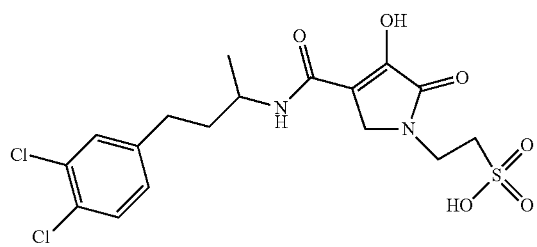 [SMILES: CC(CCc1ccc(Cl)c(Cl)c1)NC(=O)C1=C(O)C(=O)N(CCS(=O)(=O)O)C1] | 2-(4-(4-(3,4-dichlorophenyl)butan-2-ylcarbamoyl)-3-hydroxy-2-oxo-2,5-dihydro-1H-pyrrol-1-yl)ethanesulfonic acid | 0.83 | 450.9 | D |
| 317 | 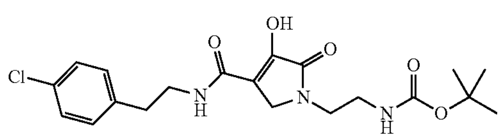 [SMILES: CC(C)(C)OC(=O)NCCN1CC(C(=O)NCCc2ccc(Cl)cc2)=C(O)C1=O] | tert-butyl 2-(4-(4-chlorophenethylcarbamoyl)-3-hydroxy-2-oxo-2,5-dihydro-1H-pyrrol-1-yl)ethylcarbamate | 1.99 | 424.1 | L |
| 322 | 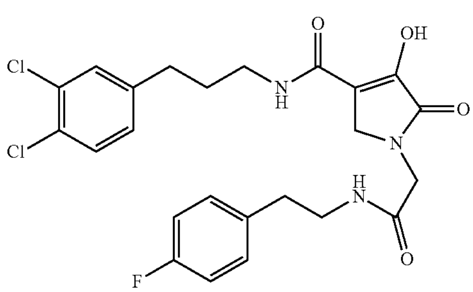 [SMILES: O=C(CN1CC(C(=O)NCCCc2ccc(Cl)c(Cl)c2)=C(O)C1=O)NCCc1ccc(F)cc1] | N-(3-(3,4-dichlorophenyl)propyl)-1-(2-(4-fluorophenethylamino)-2-oxoethyl)-4-hydroxy-5-oxo-2,5-dihydro-1H-pyrrole-3-carboxamide | 3.2 | 509 | C |

| Ex. # | Structure | Name | RT (min) | [M + 1]+ | LC/MS Methods |
|---|---|---|---|---|---|
| 323 | 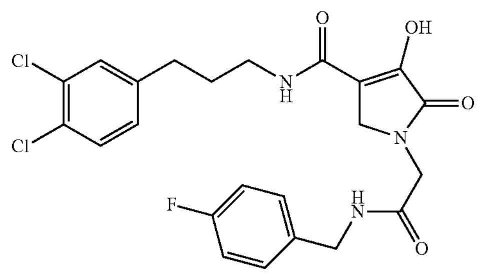 [SMILES: O=C(CN1CC(C(=O)NCCCc2ccc(Cl)c(Cl)c2)=C(O)C1=O)NCc1ccc(F)cc1] | N-(3-(3,4-dichlorophenyl) propyl)-1-(2-(4-fluorobenzylamino)-2-oxoethyl)-4-hydroxy-5-oxo-2,5-dihydro-1H-pyrrole-3-carboxamide | 2.55 | 495 | A |
| 331 | 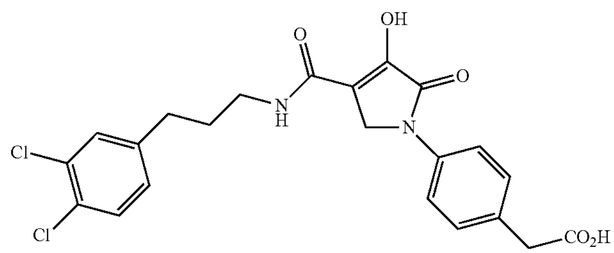 [SMILES: O=C(O)Cc1ccc(N2CC(C(=O)NCCCc3ccc(Cl)c(Cl)c3)=C(O)C2=O)cc1] | 2-(4-(4-(3-(3,4-dichlorophenyl) propylcarbamoyl)-3-hydroxy-2-oxo-2,5-dihydro-1H-pyrrol-1-yl)phenyl)acetic acid | 2.0 | 462.9 | L |
| 332 | 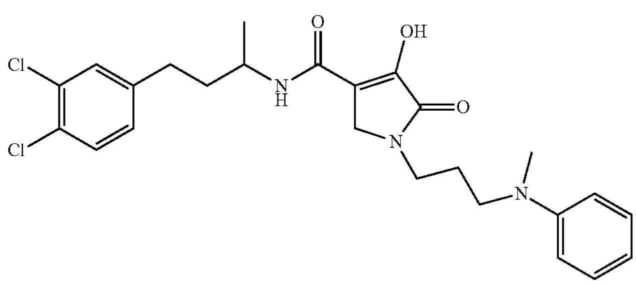 [SMILES: CC(CCc1ccc(Cl)c(Cl)c1)NC(=O)C1=C(O)C(=O)N(CCCN(C)c2ccccc2)C1] | N-(4-(3,4-dichlorophenyl) butan-2-yl)-4-hydroxy-1-(3-(methyl(phenyl)amino) propyl)-5-oxo-2,5-dihydro-1H-pyrrole-3-carboxamide | 1.90 | 490.1 | L |
| 337 | 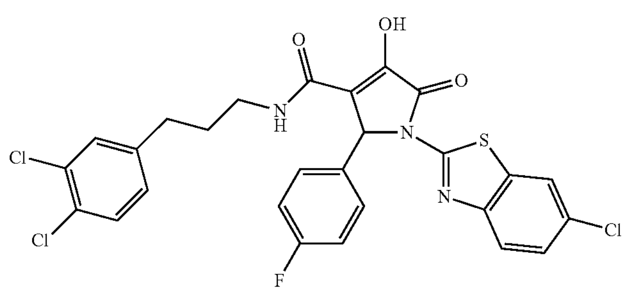 [SMILES: O=C(NCCCc1ccc(Cl)c(Cl)c1)C1=C(O)C(=O)N(c2nc3ccc(Cl)cc3s2)C1c1ccc(F)cc1] | 1-(6-chlorobenzo[d]thiazol-2-yl)-N-(3-(3,4-dichlorophenyl)propyl)-2-(4-fluorophenyl)-4-hydroxy-5-oxo-2,5-dihydro-1H-pyrrole-3-carboxamide | 4.24 | 592.1 | A |
| 339 | 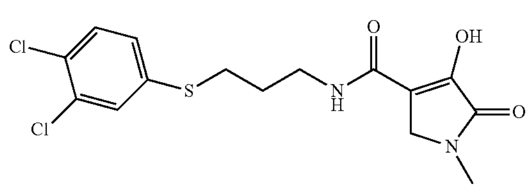 [SMILES: CN1CC(C(=O)NCCCSc2ccc(Cl)c(Cl)c2)=C(O)C1=O] | N-(3-(3,4-dichlorophenylthio) propyl)-4-hydroxy-1-methyl-5-oxo-2,5-dihydro-1H-pyrrole-3-carboxamide | 338 | 375.1 | N |
| 341 | 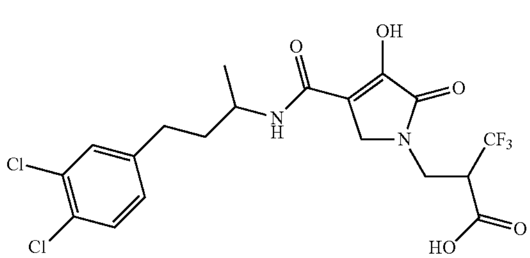 [SMILES: CC(CCc1ccc(Cl)c(Cl)c1)NC(=O)C1=C(O)C(=O)N(CC(C(=O)O)C(F)(F)F)C1] | 2-((4-(4-(3,4-dichlorophenyl) butan-2-ylcarbamoyl)-3-hydroxy-2-oxo-2,5-dihydro-1H-pyrrol-1-yl)methyl)-3,3,3-trifluoropropanoic acid | 2.1 | 482.9 | L |

TABLE 2-continued

| Ex. # | Structure | Name | RT (min) | [M + 1]+ | LC/MS Methods |
|---|---|---|---|---|---|
| 344 | 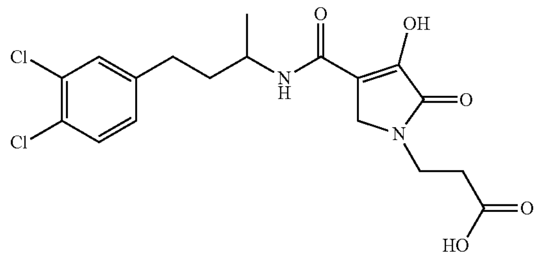 [SMILES: CC(CCc1ccc(Cl)c(Cl)c1)NC(=O)C1=C(O)C(=O)N(CCC(=O)O)C1] | 3-(4-(4-(3,4-dichlorophenyl) butan-2-ylcarbamoyl)-3-hydroxy-2-oxo-2,5-dihydro-1H-pyrrol-1-yl) propanoic acid | 1.927 | 415.0 | L |
| 345 | 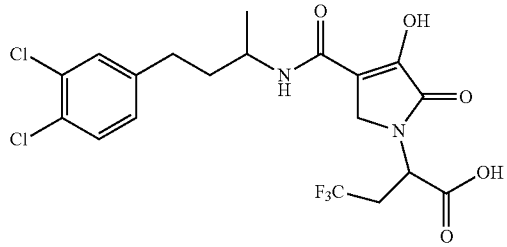 [SMILES: CC(CCc1ccc(Cl)c(Cl)c1)NC(=O)C1=C(O)C(=O)N(C(CC(F)(F)F)C(=O)O)C1] | 2-(4-(4-(3,4-dichlorophenyl) butan-2-ylcarbamoyl)-3-hydroxy-2-oxo-2,5-dihydro-1H-pyrrol-1-yl)-4,4,4-trifluorobutanoic acid | 2.0 | 482.9 | L |
| 346 | Chiral | N-(4-(3,4-dichlorophenyl) butan-2-yl)-4-hydroxy-5-oxo-1-((R)-6-(trifluoromethyl)-2,3-dihydro-1H-inden-1-yl)-2,5-dihydro-1H-pyrrole-3-carboxamide | 2.332 | 527.0 | L |
| 347 | Chiral | N-(4-(3,4-dichlorophenyl) butan-2-yl)-4-hydroxy-5-oxo-1-((S)-6-(trifluoromethyl)-2,3-dihydro-1H-inden-1-yl)-2,5-dihydro-1H-pyrrole-3-carboxamide | 2.3 | 527.1 | L |

What is claimed is:

1. A compound of Formula (I):

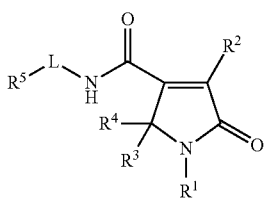

(I)

or a stereoisomer, a tautomer, or a pharmaceutically acceptable salt thereof, wherein:

$R^1$ is independently selected from the group consisting of: H, —$((CH_2)_sO)_r(C_{1-4}$ alkyl substituted with 0-1 $R^a$), $C_{1-6}$ alkyl substituted with 0-3 $R^a$, $C_{2-6}$ alkenyl substituted with 0-3 $R^a$, —$SO_2$(phenyl), —$(CH_2)_n$—$(C_{3-6}$ cycloalkyl substituted with 0-3 $R^c$), —$(CH_2)_n$(CHR$^f$)(CH$_2)_m$-phenyl, —$(CH_2)_n$-(phenyl substituted with 0-3 $R^b$), and —$(CH_2)_n$-(5- to 6-membered heterocycle comprising: carbon atoms and 1-4 heteroatoms selected from N, NR$^e$, O, and S(O)$_p$); and wherein said heterocycle is substituted with 0-3 $R^c$;

$R^2$ is independently selected from the group consisting of: OR$^6$, CN, and NR$^7$R$^8$;

R³ is independently selected from the group consisting of: H, halogen, CF₃, OCF₃, $C_{1-6}$ alkyl substituted with 0-3 $R^a$, $C_{2-6}$ alkenyl substituted with 0-3 $R^a$, —CO₂($C_{1-4}$ alkyl), —SO₂(phenyl), —(CH₂)ₙ—($C_{3-6}$ cycloalkyl substituted with 0-3 $R^c$), —(CH₂)ₙ-(phenyl substituted with 0-3 $R^b$), —(CH₂)ₙ-(naphthyl substituted with 0-3 $R^b$), and —(CH₂)ₙ-(5- to 10 membered heterocycle comprising: carbon atoms and 1-4 heteroatoms selected from N, $NR^e$, O, and $S(O)_p$), wherein said heterocycle is substituted with 0-3 $R^c$;

R⁴ is independently selected from the group consisting of: H and $C_{1-4}$ alkyl;

R⁵ is independently selected from the group consisting of: $C_{3-6}$ cycloalkyl, phenyl, naphthyl, and a 5- to 10-membered heterocycle comprising: carbon atoms and 1-4 heteroatoms selected from N, $NR^e$, O, and $S(O)_p$; and wherein each moiety is substituted with 0-3 $R^d$;

R⁶ is $C_{1-6}$ alkyl substituted with 0-1 CO₂H;

R⁷ is independently selected from the group consisting of: H, $C_{1-6}$ alkyl substituted with 0-1 $R^a$, —(CH₂)ₙ-(phenyl substituted with 0-3 $R^b$), and —(CH₂)ₙ-(5- to 6-membered heterocycle comprising: carbon atoms and 1-4 heteroatoms selected from N, $NR^e$, O, and $S(O)_p$); and wherein said heterocycle is substituted with 0-3 $R^c$;

R⁸ is independently selected from the group consisting of: H and $C_{1-6}$ alkyl;

alternatively, NR⁷R⁸ is a 5- to 6-membered heterocycle comprising: carbon atoms and 1-4 heteroatoms selected from N, $NR^e$, O, and $S(O)_p$;

L is independently a hydrocarbon or hydrocarbon-heteroatom linker optionally substituted with 0-2 $R^g$; wherein said hydrocarbon linker has one to eight carbon atoms and may be straight or branched, saturated or unsaturated; and said hydrocarbon-heteroatom linker may be saturated or unsaturated and has one to seven carbon atoms and one group selected from O, —CO—, S, —SO—, —SO₂—, NH, and N($C_{1-4}$ alkyl);

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF₃, OCF₃, CN, NH₂, NO₂, NH($C_{1-4}$ alkyl), N($C_{1-4}$ alkyl)₂, CO₂H, CO₂($C_{1-4}$ alkyl), NHCO($C_{1-4}$ alkyl substituted with 0-1 NH₂), N($C_{1-4}$ alkyl)CO($C_{1-4}$ alkyl), NHCO₂($C_{1-4}$ alkyl), CONHSO₂($C_{1-4}$ alkyl), SO₂($C_{1-4}$ alkyl), CONH₂, CONH($C_{1-4}$ alkyl), NHSO₂($C_{1-4}$ alkyl), N($C_{1-4}$ alkyl)SO₂($C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF₃, OCF₃, OCF₂CHF₂, OCH₂CF₃, CN, NH₂, NO₂, NH($C_{1-4}$ alkyl), N($C_{1-4}$ alkyl)₂, CO₂H, CO₂($C_{1-4}$ alkyl), CONH₂, CONH($C_{1-4}$ alkyl), CON($C_{1-4}$ alkyl)₂, NHCO₂($C_{1-4}$ alkyl), NHSO₂($C_{1-4}$ alkyl), N($C_{1-4}$ alkyl)SO₂($C_{1-4}$ alkyl), SO₂($C_{1-4}$ alkyl), SO₂NH₂, phenyl, benzyl, and phenoxy;

$R^c$ is, independently at each occurrence, selected from the group consisting of: =O and $R^b$;

$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, CF₃, OCF₃, CN, NH₂, NO₂, NH($C_{1-4}$ alkyl), N($C_{1-4}$ alkyl)₂, CO₂H, CO₂($C_{1-4}$ alkyl), CONH₂, CONH($C_{1-4}$ alkyl), CON($C_{1-4}$ alkyl)₂, NHCO₂($C_{1-4}$ alkyl), NHSO₂($C_{1-4}$ alkyl), SO₂($C_{1-4}$ alkyl), and SO₂NH₂;

$R^e$ is, independently at each occurrence, selected from the group consisting of: H, $C_{1-4}$ alkyl, CO($C_{1-4}$ alkyl), CO₂($C_{1-4}$ alkyl), CO₂(benzyl), and —(CH₂)ₙ-(phenyl optionally substituted with 0-2 halogens);

$R^f$ is, independently at each occurrence, selected from the group consisting of: $C_{1-4}$ alkyl, $C_{2-4}$ alkenyl, CO₂($C_{1-4}$ alkyl), CONH₂, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, CO₂($C_{1-4}$ alkyl), $C_{3-6}$ cycloalkyl, and phenyl;

m, at each occurrence, is selected from 0, 1, and 2;

n, at each occurrence, is selected from 0, 1, 2, 3, and 4;

p, at each occurrence, is selected from 0, 1, and 2; and s and r are, independently at each occurrence, selected from 1, 2, 3, and 4.

2. A compound according to claim 1, wherein the compound is of Formula (Ia):

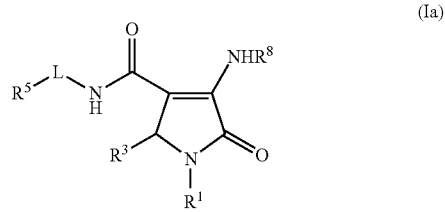

(Ia)

or a stereoisomer, a tautomer, or a pharmaceutically acceptable salt thereof, wherein:

R¹ is $C_{1-4}$ alkyl substituted with 0-2 $R^a$;

R³ is independently H or $C_{1-4}$ alkyl;

R⁵ is phenyl substituted with 0-3 $R^d$;

R⁸ is independently selected from the group consisting of: H, $C_{1-4}$ alkyl substituted with 0-2 $R^a$, $C_{3-6}$ cycloalkyl, —(CH₂)ₙ-(phenyl substituted with 0-2 $R^a$), and —(CH₂)ₙ-(heterocycle substituted with 0-2 $R^c$); wherein said heterocycle is selected from tetrahydrofuranyl, pyrrolidinyl, piperidinyl and pyridyl; and L is $C_{1-5}$ alkylene, wherein said alkylene may be straight or branched chain.

3. A compound according to claim 2, wherein:

R¹ is $C_{1-4}$ alkyl;

R³ is H;

R⁵ is phenyl optionally substituted with one, two, or three halogen atoms;

R⁸ is selected from the group consisting of: H, $C_{1-4}$ alkyl substituted with 0-1 $R^a$, cyclopropyl, phenyl, benzyl, (3,4-diCl-phenyl)-(CH₂)₃—, (tetrahydrofuran-2-yl)-CH₂—, (1-Me-pyrrolidin-2-yl)-(CH₂)—, (piperidin-1-yl)-(CH₂)₃—, and (pyrid-4-yl)-(CH₂)₂—; and L is —(CH₂)₃— or —(CH₂)₄—.

4. A compound according to claim 2, wherein:

R¹ is ethyl;

R³ is H;

R⁵ is 3,4-diCl-phenyl;

R⁸ is H, methyl, —CH₂CF₃, —(CH₂)₂OCH₂CH₃, —(CH₂)₂OCH(CH₃)₂, cyclopropyl, phenyl, benzyl, (3,4-diCl-phenyl)-(CH₂)₃—, (tetrahydrofuran-2-yl)-CH₂—, (1-Me-pyrrolidin-2-yl)-(CH₂)—, (piperidin-1-yl)-(CH₂)₃—, and (pyrid-4-yl)-(CH₂)₂—; and L is —(CH₂)₃—.

5. A compound of Formula (II):

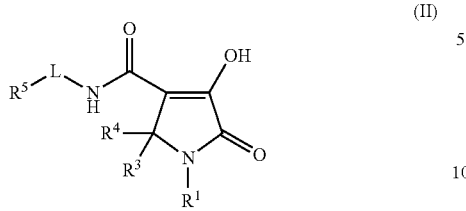

or a stereoisomer, a tautomer, or a pharmaceutically acceptable salt thereof, wherein:
- $R^1$ is independently selected from the group consisting of: H, $C_{1-6}$ alkyl substituted with 0-3 $R^a$, $C_{2-6}$ alkenyl substituted with 0-3 $R^a$, —$SO_2$(phenyl), —$(CH_2)_n$—($C_{3-6}$ cycloalkyl substituted with 0-3 $R^c$), —$(CH_2)_n$(CHR$^f$)(CH$_2$)$_m$-phenyl, —$(CH_2)_n$-(phenyl substituted with 0-3 $R^b$), and —$(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;
- $R^3$ is independently selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, —$CO_2$($C_{1-4}$ alkyl), —$SO_2$(phenyl), —$(CH_2)_n$—($C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;
- $R^4$ is independently selected from the group consisting of: H and $C_{1-4}$ alkyl;
- $R^5$ is independently selected from the group consisting of: $C_{3-6}$ cycloalkyl, benzothiazolyl, indazolyl, chromanyl, and quinolinyl; and wherein each moiety is substituted with 0-3 $R^d$;
- alternatively, $R^5$ is phenyl substituted with $OCF_3$ or $SO_2NH_2$;
- L is independently a hydrocarbon or hydrocarbon-heteroatom linker; wherein said hydrocarbon linker is saturated and has one to eight carbon atoms; and said hydrocarbon-heteroatom linker is saturated and has one to seven carbon atoms and one O;
- $R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)$CO(C_{1-4}$ alkyl), $NHCO_2$($C_{1-4}$ alkyl), $CONHSO_2$($C_{1-4}$ alkyl), $SO_2$($C_{1-4}$ alkyl), $CONH_2$, $CONH(C_{1-4}$ alkyl), $NHSO_2$($C_{1-4}$ alkyl), $N(C_{1-4}$ alkyl)$SO_2$($C_{1-4}$ alkyl), and phenoxy;
- $R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, $OCH_2CF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2$($C_{1-4}$ alkyl), $NHSO_2$($C_{1-4}$ alkyl), $N(C_{1-4}$ alkyl)$SO_2$($C_{1-4}$ alkyl), $SO_2$($C_{1-4}$ alkyl), $SO_2NH_2$, phenyl, benzyl, and phenoxy;
- $R^c$ is, independently at each occurrence, selected from the group consisting of: =O and $R^b$;
- $R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $CONH_2$, $CONH(C_{1-4}$ alkyl), $CON(C_{1-4}$ alkyl)$_2$, $NHCO_2$($C_{1-4}$ alkyl), $NHSO_2$($C_{1-4}$ alkyl), $SO_2$($C_{1-4}$ alkyl), and $SO_2NH_2$;
- $R^e$ is, independently at each occurrence, selected from the group consisting of: H, $C_{1-4}$ alkyl, $CO(C_{1-4}$ alkyl), $CO_2(C_{1-4}$ alkyl), $CO_2$(benzyl), and —$(CH_2)_n$-(phenyl optionally substituted with 0-2 halogens);
- $R^f$ is, independently at each occurrence, selected from the group consisting of: $C_{1-4}$ alkyl, $C_{2-4}$ alkenyl, $CO_2$($C_{1-4}$ alkyl), $C_{3-6}$ cycloalkyl, phenyl, and benzyl;
- m, at each occurrence, is selected from 0, 1, and 2;
- n, at each occurrence, is selected from 0, 1, 2, 3, and 4;
- p, at each occurrence, is selected from 0, 1, and 2; and
- s, at each occurrence, is selected from 1, 2, 3, and 4.

6. A compound according to claim 5, wherein:
- $R^1$ is $C_{1-4}$ alkyl;
- $R^5$ is independently selected from the group consisting of: cyclohexyl, indazolyl, chromanyl, and quinolinyl; and wherein each moiety is substituted with 0-2 $R^d$;
- alternatively, $R^5$ is phenyl substituted with $OCF_3$ or $SO_2NH_2$; and
- L is independently —$(CH_2)_3$—, or —$(CH_2)_4$—.

7. A compound according to claim 5, wherein:
- $R^1$ is independently selected from the group consisting of: H, $C_{1-6}$ alkyl substituted with 0-3 $R^a$, $C_{2-6}$ alkenyl substituted with 0-3 $R^a$, —$SO_2$(phenyl), —$(CH_2)_n$—($C_{3-6}$ cycloalkyl substituted with 0-3 $R^c$), —$(CH_2)_n$(CHR$^f$)(CH$_2$)$_m$-phenyl, —$(CH_2)_n$-(phenyl substituted with 0-3 $R^b$), and —$(CH_2)_n$-(5- to 6-membered heterocycle comprising: carbon atoms and 1-4 heteroatoms selected from N, $NR^e$, O, and $S(O)_p$); and wherein said heterocycle is substituted with 0-3 $R^c$;
- $R^3$ is independently selected from the group consisting of: H, halogen, $CF_3$, $OCF_3$, $C_{1-6}$ alkyl substituted with 0-3 $R^a$, $C_{2-6}$ alkenyl substituted with 0-3 $R^a$, —$CO_2(C_{1-4}$ alkyl), —$SO_2$(phenyl), —$(CH_2)_n$—($C_{3-6}$ cycloalkyl substituted with 0-3 $R^c$), —$(CH_2)_n$-(phenyl substituted with 0-3 $R^b$), —$(CH_2)_n$-(naphthyl substituted with 0-3 $R^b$), and —$(CH_2)_n$-(5- to 10 membered heterocycle comprising: carbon atoms and 1-4 heteroatoms selected from N, $NR^e$, O, and $S(O)_p$), wherein said heterocycle is substituted with 0-3 $R^c$;
- $R^4$ is independently selected from the group consisting of: H and $C_{1-4}$ alkyl;
- $R^5$ is independently selected from the group consisting of: $C_{3-6}$ cycloalkyl, phenyl, naphthyl, and a 5- to 10-membered heterocycle comprising: carbon atoms and 1-4 heteroatoms selected from N, $NR^e$, O, and $S(O)_p$; and wherein each moiety is substituted with 0-3 $R^d$;
- L is independently a hydrocarbon or hydrocarbon-heteroatom linker optionally substituted with 0-2 $R^g$; wherein said hydrocarbon linker is unsaturated and has one to eight carbon atoms; and said hydrocarbon-heteroatom linker may be saturated or unsaturated and has one to seven carbon atoms and one group selected from —CO—, S, —SO—, —$SO_2$—, NH, and $N(C_{1-4}$ alkyl);
- $R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl)$_2$, $CO_2H$, $CO_2(C_{1-4}$ alkyl), $NHCO(C_{1-4}$ alkyl substituted with 0-1 $NH_2$), $N(C_{1-4}$ alkyl)$CO(C_{1-4}$ alkyl), $NHCO_2(C_{1-4}$ alkyl), $CONHSO_2(C_{1-4}$ alkyl), $SO_2(C_{1-4}$ alkyl), $CONH_2$, CONH($C_{1-4}$ alkyl), NHSO$_2$($C_{1-4}$ alkyl), N($C_{1-4}$ alkyl) SO$_2$($C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF$_3$, OCF$_3$, OCF$_2$CHF$_2$, OCH$_2$CF$_3$, CN, NH$_2$, NO$_2$, NH($C_{1-4}$ alkyl), N($C_{1-4}$ alkyl)$_2$, CO$_2$H, CO$_2$($C_{1-4}$ alkyl), CONH$_2$, CONH ($C_{1-4}$ alkyl), CON($C_{1-4}$ alkyl)$_2$, NHCO$_2$($C_{1-4}$ alkyl), NHSO$_2$($C_{1-4}$ alkyl), N($C_{1-4}$ alkyl)SO$_2$($C_{1-4}$ alkyl), SO$_2$ ($C_{1-4}$ alkyl), SO$_2$NH$_2$, phenyl, benzyl, and phenoxy;

$R^c$ is, independently at each occurrence, selected from the group consisting of: =O and $R^b$;

$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, CF$_3$, OCF$_3$, CN, NH$_2$, NO$_2$, NH($C_{1-4}$ alkyl), N($C_{1-4}$ alkyl)$_2$, CO$_2$H, CO$_2$ ($C_{1-4}$ alkyl), CONH$_2$, CONH($C_{1-4}$ alkyl), CON($C_{1-4}$ alkyl)$_2$, NHCO$_2$($C_{1-4}$ alkyl), NHSO$_2$($C_{1-4}$ alkyl), SO$_2$ ($C_{1-4}$ alkyl), and SO$_2$NH$_2$;

$R^e$ is, independently at each occurrence, selected from the group consisting of: H, $C_{1-4}$ alkyl, CO($C_{1-4}$ alkyl), CO$_2$ ($C_{1-4}$ alkyl), CO$_2$(benzyl), and —(CH$_2$)$_n$-(phenyl optionally substituted with 0-2 halogens);

$R^f$ is, independently at each occurrence, selected from the group consisting of: $C_{1-4}$ alkyl, $C_{2-4}$ alkenyl, CO$_2$($C_{1-4}$ alkyl), CONH$_2$, $C_{3-6}$ cycloalkyl, phenyl, and benzyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, CO$_2$($C_{1-4}$ alkyl), $C_{3-6}$ cycloalkyl, and phenyl;

m is, independently at each occurrence, selected from 0, 1, and 2;

n is, independently at each occurrence, selected from 0, 1, 2, 3, and 4;

p is, independently at each occurrence, selected from 0, 1, and 2; and s is, independently at each occurrence, selected from 1, 2, 3, and 4.

8. A compound according to claim 5, wherein:

$R^1$ is $C_{1-4}$ alkyl;

$R^5$ is independently selected from the group consisting of: phenyl, indazolyl, and quinolinyl; and wherein each moiety is substituted with 0-2 $R^d$; and L is independently —C≡CCH$_2$—, —(CH$_2$), —CH(CH=CH$_2$)—, —(CH$_2$), —CH(cyclopropyl)-, —(CH$_2$)$_3$—CH(CO$_2$Me)-, —S—(CH$_2$)$_2$— or —N(Me)(CH$_2$)$_3$—.

9. A compound according to claim 5, wherein:

$R^1$ is independently selected from the group consisting of: ((CH$_2$)$_s$O)$_n$($C_{1-4}$ alkyl), —((CH$_2$)$_s$O)$_n$(CH$_2$)$_s$NH$_2$, —((CH$_2$)$_s$O)$_n$(CH$_2$)$_s$CH($C_{1-4}$ alkyl)(CH$_2$)$_s$($C_{1-4}$ alkyl), —((CH$_2$)$_s$O)$_n$(CH$_2$)$_s$NHCO(CH$_2$)$_s$NH$_2$, ((CH$_2$)$_s$O)$_n$ (CH$_2$)$_s$NHCO$_2$(t-Bu), —((CH$_2$)$_s$O)$_n$(CH$_2$)$_s$NHCO (CH$_2$)$_s$NHCO$_2$($C_{1-4}$ alkyl), —(CH$_2$)$_s$CONHSO$_2$($C_{1-4}$ alkyl), $C_{1-6}$ alkyl substituted with 1-3 $R^a$, $C_{1-6}$ alkyl substituted with N$_3$ or SO$_2$OH, —(CH$_2$)$_s$—$C_{3-6}$ cycloalkyl, —(CH$_2$)$_n$—$C_{3-6}$ cycloalkyl substituted with 1-3 $R^c$), —(CH$_2$)$_n$-(phenyl substituted with SO$_2$NH$_2$ or OCF$_3$), —W-(phenyl substituted with 0-3 $R^b$), —W-(pyridyl substituted with 0-3 $R^b$),

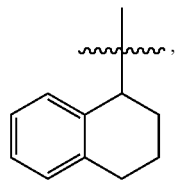 [SMILES: *C1CCCc2ccccc21]

and —(CH$_2$)$_n$-(heterocycle substituted with 0-3 $R^c$); wherein said heterocycle is selected from a group consisting of: tetrahydrofuranyl, pyrazolyl, tetrazolyl, oxadiazolyl, pyrazinyl, benzothiazolyl,

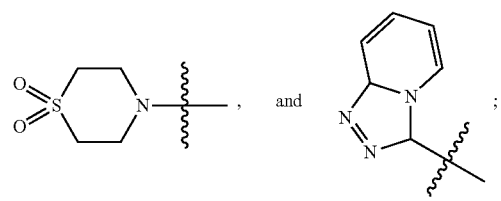 [SMILES: *N1CCS(=O)(=O)CC1 ; *C1N=NC2C=CC=CN12]

alternatively, $R^1$ is —(CH$_2$)$_n$-heterocycle; and wherein said heterocycle is substituted with 1-3 $R^c$ and is selected from a group consisting of: pyrrolidinyl, imidazolyl, and thiazolyl;

W is independently selected from the group consisting of: —(CH$_2$)$_n$(CHR$^f$)(CH$_2$)$_m$—, —(CH$_2$)$_n$CH=CH(CH$_2$)$_m$—, —(CH$_2$)$_s$O(CH$_2$)$_m$—, —(CH$_2$)$_s$NH(CH$_2$)$_m$—, —(CH$_2$)$_s$N($C_{1-4}$ alkyl)(CH$_2$)$_m$—, —(CH$_2$)$_s$CONH(CH$_2$)$_m$—, —(CH$_2$)$_s$NHCO(CH$_2$)$_m$—, —(CH$_2$)$_s$N($C_{1-4}$ alkyl)CO(CH$_2$)$_m$—, —(CH$_2$)$_s$NHCONH(CH$_2$)$_m$—, —(CH$_2$)$_s$N($C_{1-4}$ alkyl)CONH(CH$_2$)$_m$—, and —(CH$_2$)$_s$CONHSO$_2$(CH$_2$)$_m$—;

$R^3$ is independently selected from the group consisting of: H, halogen, $C_{1-6}$ alkyl, and —(CH$_2$)$_n$-phenyl substituted with 0-3 $R^b$;

$R^4$ is H;

$R^5$ is independently selected from the group consisting of: phenyl and naphthyl; wherein each moiety is substituted with 0-3 $R^d$;

L is independently a hydrocarbon or hydrocarbon-heteroatom linker; wherein said hydrocarbon linker is saturated, has one to eight carbon atoms and may be straight or branched; and said hydrocarbon-heteroatom linker is saturated and has one to seven carbon atoms and one O;

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF$_3$, OCF$_3$, CN, NH$_2$, NO$_2$, NH($C_{1-4}$ alkyl), N($C_{1-4}$ alkyl)$_2$, CO$_2$H, CO$_2$ ($C_{1-4}$ alkyl), NHCO($C_{1-4}$ alkyl substituted with 0-1 NH$_2$), N($C_{1-4}$ alkyl)CO($C_{1-4}$ alkyl), NHCO$_2$($C_{1-4}$ alkyl), CONHSO$_2$($C_{1-4}$ alkyl), SO$_2$($C_{1-4}$ alkyl), CONH$_2$, CONH($C_{1-4}$ alkyl), NHSO$_2$($C_{1-4}$ alkyl), N($C_{1-4}$ alkyl) SO$_2$($C_{1-4}$ alkyl), and phenoxy;

$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CF$_3$, OCF$_3$, OCF$_2$CHF$_2$, OCH$_2$CF$_3$, CN, NH$_2$, NO$_2$, NH($C_{1-4}$ alkyl), N($C_{1-4}$ alkyl)$_2$, CO$_2$H, CO$_2$($C_{1-4}$ alkyl), CONH$_2$, CONH ($C_{1-4}$ alkyl), CON($C_{1-4}$ alkyl)$_2$, NHCO$_2$($C_{1-4}$ alkyl), NHSO$_2$($C_{1-4}$ alkyl), N($C_{1-4}$ alkyl)SO$_2$($C_{1-4}$ alkyl), SO$_2$ ($C_{1-4}$ alkyl), SO$_2$NH$_2$, phenyl, benzyl, and phenoxy;

$R^c$ is, independently at each occurrence, selected from the group consisting of: =O and $R^b$;

$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl$)_2$, $CO_2H$, $CO_2(C_{1-4}$ alkyl), $CONH_2$, $CONH(C_{1-4}$ alkyl), $CON(C_{1-4}$ alkyl$)_2$, $NHCO_2(C_{1-4}$ alkyl), $NHSO_2(C_{1-4}$ alkyl), $SO_2(C_{1-4}$ alkyl), and $SO_2NH_2$;

$R^f$ is, independently at each occurrence, selected from the group consisting of: $C_{1-4}$ alkyl, $C_{2-4}$ alkenyl, $CO_2(C_{1-4}$ alkyl), $CONH_2$, $C_{3-6}$ cycloalkyl, phenyl, and benzyl;

m is, independently at each occurrence, selected from 0, 1, and 2;

n is, independently at each occurrence, selected from 1, 2, 3, and 4; and s is, independently at each occurrence, selected from 1, 2, 3, and 4.

10. A compound according to claim 5, wherein:

$R^1$ is independently selected from the group consisting of: —$CH_2CF_3$, —$(CH_2)_2CF_3$, —$(CH_2)_3CF_3$, —$(CH_2)_2CO_2H$, —$CH_2CH(CF_3)CO_2H$, —$CH_2CH(CO_2H)CF_3$, —$CH_2C(Me)F_2$, —$(CH_2)_2N_3$, —$(CH_2)_3O(CH_2)_2OMe$, —$(CH_2)_2O(CH_2)_2O(CH_2)_2NH_2$, —$(CH_2)_3OCH_2CH(Et)(CH_2)_3)Me$, —$(CH_2)_2O(CH_2)_2O(CH_2)_2NHCO(CH_2)_2NH_2$, —$CH_2CONHSO_2Me$, —$(CH_2)_2SO_2OH$, —$(CH_2)_2NHCO(i-Bu)$, —$(CH_2)_2NHCOMe$, —$(CH_2)_2NMeCOMe$, —$(CH_2)_2NHCO_2(t-Bu)$, —$((CH_2)_2O)_2(CH_2)_2NHCO_2(t-Bu)$, —$((CH_2)_2O)_3(CH_2)_2NHCO_2(t-Bu)$, —$((CH_2)_2O)_2(CH_2)_2NHCO(CH_2)_2NHCO_2(t-Bu)$, —$(CH_2)_2OPh$, —$(CH_2)_3OPh$, —$(CH_2)_2NHPh$, —$(CH_2)_3N(Me)Ph$, cyclopropylmethyl, cyclohexylmethyl, 4-(t-Bu)-cyclohexyl, 4-$N(Me)_2$-cyclohexyl, (tetrahydrofurran-2-yl)methyl, 2-(1-Me-pyrrolidin-2-yl)ethyl, (1-Bn-pyrrolidin-3-yl), (1-Me-pyrazol-3-yl)methyl, 1-Et-pyrazol-5-yl, 1-Me-imidazol-4-yl, (2-Me-imidazol-1-yl)methyl, (4-Ph-thiazol-2-yl)methyl, (5-Ph-1,3,4-oxadiazol-2-yl)methyl, (1H-1,2,3-triazol-4-yl)methyl, (1H-tetrazol-5-yl)methyl-,

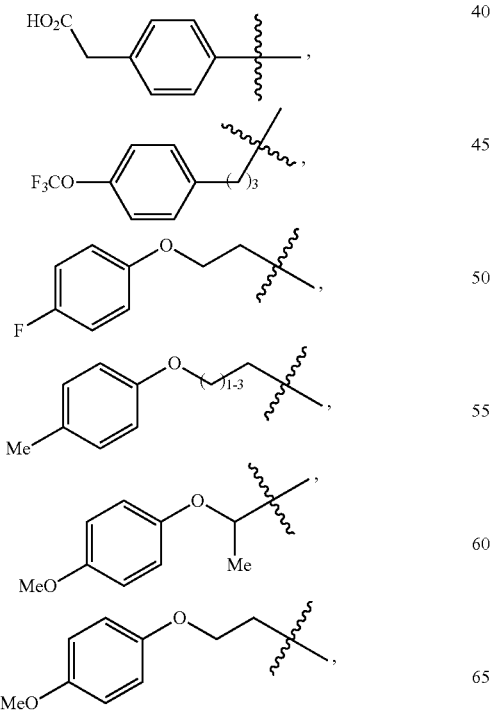

-continued

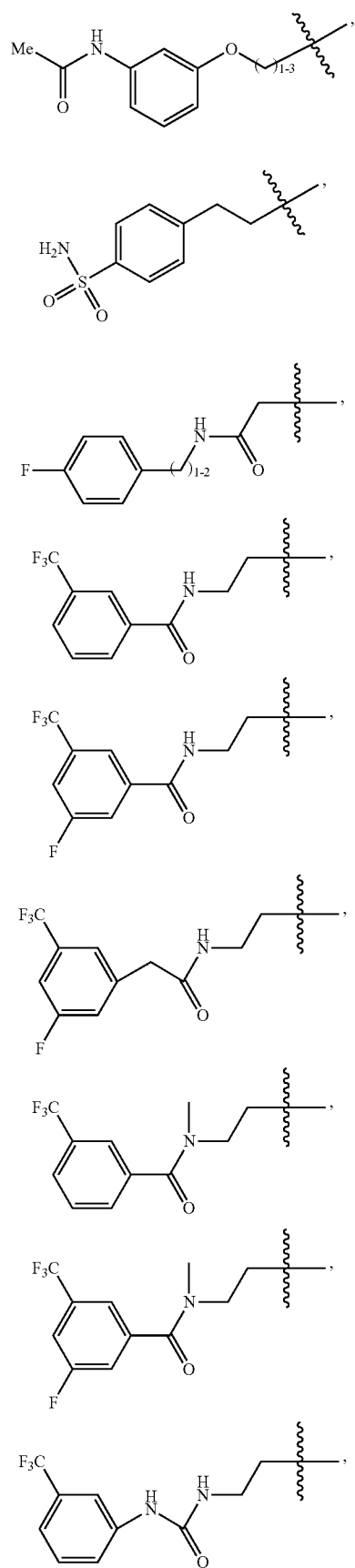

-continued

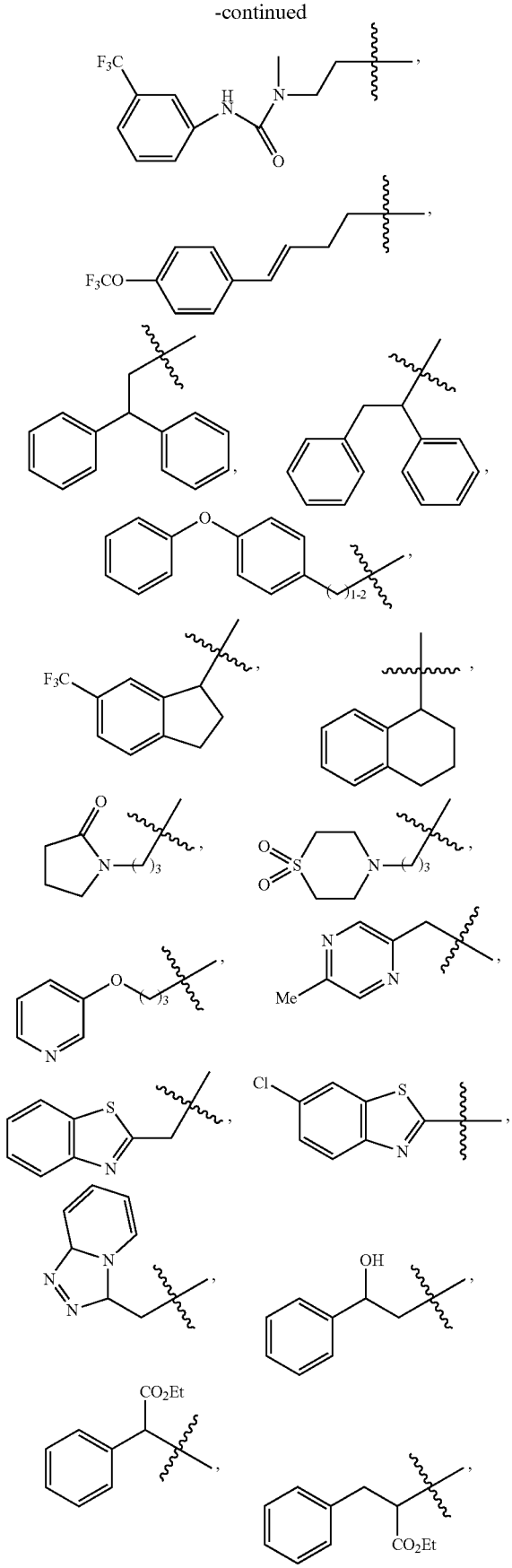

$R^3$ is independently H, methyl or 4-F-phenyl;
$R^4$ is H;
$R^5$ is independently 2,6-diCl-phenyl or 3,4-diCl-phenyl; and
L is independently —$(CH_2)_2$—, —$(CH_2)_3$— or —$(CH_2)_2$CHMe-.

11. A compound according to claim 5, wherein:
$R^1$ is independently selected from the group consisting of: H, $C_{1-6}$ alkyl substituted with 0-3 $R^a$, and —$(CH_2)_n$-(phenyl substituted with 0-3 $R^b$);
$R^3$ is independently selected from the group consisting of: —$CO_2(C_{1-4}$ alkyl), —$(CH_2)_n$-(thiadiazolyl substituted with 0-1 $R^b$), and —$(CH_2)_n$—(N—$C_{1-4}$ alkyl-imidazolyl);
$R^4$ is H;
$R^5$ is independently selected from the group consisting of: phenyl and naphthyl; wherein each moiety is substituted with 0-3 $R^d$;
L is independently a hydrocarbon or hydrocarbon-heteroatom linker; wherein said hydrocarbon linker is saturated, has one to eight carbon atoms and may be straight or branched; and said hydrocarbon-heteroatom linker is saturated and has one to seven carbon atoms and one O;
$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl$)_2$, $CO_2H$, $CO_2(C_{1-4}$ alkyl), $SO_2(C_{1-4}$ alkyl), phenyl, benzyl, and phenoxy;
$R^b$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, $CF_3$, $OCF_3$, $OCF_2CHF_2$, CN, $NH_2$, $NO_2$, $NH(C_{1-4}$ alkyl), $N(C_{1-4}$ alkyl$)_2$, $CO_2H$, $CO_2(C_{1-4}$ alkyl), $CONH_2$, $CONH(C_{1-4}$ alkyl), $CON(C_{1-4}$ alkyl$)_2$, $NHCO(C_{1-4}$ alkyl), $NHSO_2(C_{1-4}$ alkyl), $SO_2(C_{1-4}$ alkyl), $SO_2NH_2$, phenyl, benzyl, and phenoxy;
$R^d$ is, independently at each occurrence, selected from the group consisting of: halogen, OH, $C_{1-6}$ alkyl, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl$)_2$, $CO_2H$, and $CO_2(C_{1-4}$ alkyl); and
n, at each occurrence, is selected from 1, 2, 3, and 4.

12. A compound according to claim 5, wherein:
$R^1$ is independently selected from the group consisting of: methyl and phenyl;
$R^3$ is independently selected from the group consisting of: —$CO_2Me$, 1,2,3-thiadiazol-4-yl, and N-methyl-imidazol-4-yl;

$R^4$ is H;
$R^5$ is 3,4-diCl-phenyl; and
L is —$(CH_2)_3$—.

13. A compound of Formula (III):

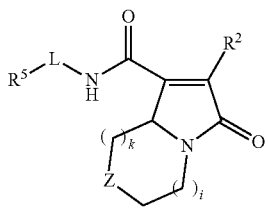

(III)

or a stereoisomer, a tautomer, or a pharmaceutically acceptable salt thereof, wherein:

$R^2$ is OH;
$R^5$ is 3,4-diCl-phenyl;
L is —$(CH_2)_3$— or —$(CH_2)_2CH(Me)$-;
Z is $CH_2$ or NHCO;
k is 1; and
i is 1 or 2.

14. A compound according to claim 1, wherein the compound is selected from the exemplified examples or a stereoisomer, a tautomer, or a pharmaceutically acceptable salt.

15. A pharmaceutical composition, comprising: a pharmaceutically acceptable carrier and a compound of claim 1.

16. A pharmaceutical composition, comprising: a pharmaceutically acceptable carrier and a compound of claim 2.

17. A pharmaceutical composition, comprising: a pharmaceutically acceptable carrier and a compound of claim 5.

18. A pharmaceutical composition, comprising: a pharmaceutically acceptable carrier and a compound of claim 13.

* * * * *